United States Patent
Panknin et al.

(10) Patent No.: US 10,179,123 B2
(45) Date of Patent: Jan. 15, 2019

(54) 2-ARYL- AND 2-ARYLALKYL-BENZIMIDAZOLES AS MIDH1 INHIBITORS

(71) Applicant: BAYER PHARMA AKTIENGESELLSCHAFT, Berlin (DE)

(72) Inventors: Olaf Panknin, Berlin (DE); Katja Zimmermann, Düsseldorf (DE); Roland Neuhaus, Berlin (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

(21) Appl. No.: 15/742,363

(22) PCT Filed: Jul. 4, 2016

(86) PCT No.: PCT/EP2016/065656
§ 371 (c)(1),
(2) Date: Jan. 5, 2018

(87) PCT Pub. No.: WO2017/005674
PCT Pub. Date: Jan. 12, 2017

(65) Prior Publication Data
US 2018/0207137 A1    Jul. 26, 2018

(30) Foreign Application Priority Data
Jul. 7, 2015  (EP) .................................. 15175723

(51) Int. Cl.
| | |
|---|---|
| *A61K 31/4184* | (2006.01) |
| *A61K 31/427* | (2006.01) |
| *C07D 235/08* | (2006.01) |
| *C07D 235/18* | (2006.01) |
| *C07D 403/06* | (2006.01) |
| *C07D 417/06* | (2006.01) |
| *A61K 45/06* | (2006.01) |

(52) U.S. Cl.
CPC ........ *A61K 31/4184* (2013.01); *A61K 31/427* (2013.01); *A61K 45/06* (2013.01); *C07D 235/08* (2013.01); *C07D 235/18* (2013.01); *C07D 403/06* (2013.01); *C07D 417/06* (2013.01)

(58) Field of Classification Search
CPC .. A61K 31/4184; A61K 31/427; A61K 45/06; C07D 235/08; C07D 235/18; C07D 403/06; C07D 417/06
USPC ......................................................... 514/394
See application file for complete search history.

(56) References Cited

U.S. PATENT DOCUMENTS

| | | |
|---|---|---|
| 9,951,027 B2 | 4/2018 | Rehwinkel et al. |
| 9,957,235 B2 | 5/2018 | Rehwinkel et al. |
| 2015/0031627 A1 | 1/2015 | Lemieux et al. |
| 2017/0319549 A1 | 11/2017 | Rehwinkel et al. |
| 2017/0320861 A1 | 11/2017 | Rehwinkel et al. |
| 2018/0170882 A1 | 6/2018 | Jena et al. |
| 2018/0201585 A1 | 7/2018 | Panknin et al. |
| 2018/0215717 A1 | 8/2018 | Panknin et al. |
| 2018/0222870 A1 | 8/2018 | Schirmer et al. |
| 2018/0222871 A1 | 8/2018 | Schirmer et al. |

FOREIGN PATENT DOCUMENTS

| | | | |
|---|---|---|---|
| WO | WO-2008153701 | 12/2008 | |
| WO | WO-2008153701 A1 * | 12/2008 | ........... C07D 235/12 |
| WO | WO-2013046136 | 4/2013 | |
| WO | WO-2015121209 | 8/2015 | |

(Continued)

OTHER PUBLICATIONS

International Search Report and Written Opinion dated Aug. 16, 2016 for International Application No. PCT/EP2016/065656, filed Jul. 4, 2016, 10 pages.
Beaulieu, P., (2004) "Non-nucleoside inhibitors of the hepatitis C virus NS5B polymerase: discovery and preliminary SAR of benzimidazole derivatives," *Bioorganic & Medicinal Chemistry Letters*, 14:119-124.
Rohle, D., (May 3, 2013) "An Inhibitor of Mutant IDH1 Delays Growth and Promotes Differentiation of Glioma Cells," *Science*, 340:626-630.
U.S. Appl. No. 15/520,384, filed Oct. 21, 2015, for Rehwinkel et al. (Also published as US-20170319549).

(Continued)

*Primary Examiner* — Kahsay Habte
(74) *Attorney, Agent, or Firm* — Morrison & Foerster LLP

(57) ABSTRACT

The present invention relates to 2-Aryl- and 2-Arylalkyl-benzimidazoles of general formula (I): in which A, $R^1$, $R^4$, $R^5$, $R^6$, $R^7$, $R^8$, $R^9$, $R^{10}$ and $R^{11}$ are as defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

(I)

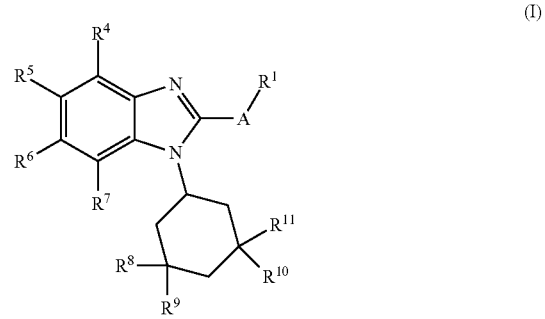

15 Claims, No Drawings

(56) References Cited

FOREIGN PATENT DOCUMENTS

| WO | WO-2016062677 | 4/2016 |
|----|---------------|--------|
| WO | WO-2016062770 | 4/2016 |
| WO | WO-2016198322 | 12/2016 |
| WO | WO-2017009325 | 1/2017 |
| WO | WO-2017012967 | 1/2017 |
| WO | WO-2017016992 | 2/2017 |
| WO | WO-2017017046 | 2/2017 |

OTHER PUBLICATIONS

U.S. Appl. No. 15/520,385, filed Oct. 21, 2015, for Rehwinkel et al. (Also published as US-20170320861).
U.S. Appl. No. 15/580,372, filed Jun. 3, 2016, for Ring et al. (Also published as US-20180170882).
U.S. Appl. No. 15/744,641, filed Jul. 12, 2016, for Panknin et al. (Also published as US-20180201585).
U.S. Appl. No. 15/746,352, filed Jul. 14, 2016, for Panknin et al. (Also published as US-20180215717).
U.S. Appl. No. 15/748,014, filed Jul. 22, 2016, for Schirmer. (Also published as US-20180222870).
U.S. Appl. No. 15/748,027, filed Mar. 16, 2018, for Schirmer. (Also published as US-20180222871).
U.S. Appl. No. 15/923,895, filed Jul. 25, 2016, for Schirmer. (Also published as US-20180222871).

\* cited by examiner

2-ARYL- AND 2-ARYLALKYL-BENZIMIDAZOLES AS MIDH1 INHIBITORS

CROSS REFERENCE TO RELATED APPLICATIONS

This application is a National Phase application under 35 U.S.C. § 371 of International Application No. PCT/EP2016/065656 filed Jul. 4, 2016, which claims priority benefit of European Application No. 1517723.4, filed Jul. 7, 2015.

The present invention relates to 2-aryl- and 2-arylalkyl-benzimidazole compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

BACKGROUND OF THE INVENTION

The present invention relates to chemical compounds that inhibit mutated isocitrate dehydrogenase 1 (mIDH1 R132H), to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

Isocitrate dehydrogenases (IDH) are key enzymes in cellular metabolism, converting isocitrate to alpha-ketoglutarate and belong to 2 subgroups, defined by the utilization of different electron receptors. Two of them, isocitrate dehydrogenase 1 and 2 use NADP(+) as electron receptor. IDH1 is located in the cytoplasm and peroxisomes and IDH2 in the mitochondria as an integral part of the TCA cycle, e.g in the following reaction:

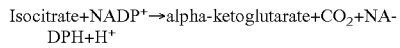

Both enzymes act as homodimers.

In a variety of tumor entities, including glioma, acute myeloid leukemia (AML), chondrosarcoma, cholangiocarcinoma, melanoma, prostate cancer, angioimmunoblastic T-cell lymphoma and others, IDH1 or IDH2 are mutated at a distinct amino acid position (Balss J. Acta Neuropathol. 2008 December; 116(6):597-602, Mardis E R, N Engl J Med. 2009 Sep. 10; 361(11):1058-66, Amary M F, J Pathol. 2011 July; 224(3):334-43, Borger D R, Oncologist. 2012; 17(1):72-9, Shibata T, Am J Pathol. 2011 March; 178(3): 1395-402, Ghiam A F, Oncogene. 2012 Aug. 16; 31(33): 3826, Cairns R A, Blood. 2012 Feb. 23; 119(8):1901-3). This mutation is always heterozygous and mutual exclusive. Most of these point mutations have been found at key positions in the catalytic domain of the enzyme (responsible for 2-oxoglutarate coordination), e.g. IDH1R100, IDH1R132, IDH1G97 and IDH2R140, IDH2R172 (Dang L., Nature, 2009 Dec. 10; 462(7274):739-44). In glioma, more than 70% of all non-primary glioblastoma are IDH1 mutated and in 92.7% of the IDH1 mutated tumors the arginine was replaced by a histidine (IDH1R132H) (Hartmann C, Acta Neuropathol. 2009 October; 118(4):469-74).

The replacement of the wildtype amino acid at those catalytic residues leads to a neomorphic activity of the enzyme, converting alpha-ketoglutarate to R-2-hydroxyglutarate (2-HG). 2-HG is metabolic waste, but also an oncometabolite and it is believed to contribute to tumor genesis (Dang L., Nature, 2009 Dec. 10; 462(7274):739-44). 2-HG is only produced in very low levels in normal cells, but cells harboring the IDH mutations produce high levels of 2-HG. High amounts of 2-HG have also been found in tumors with the IDH mutation. IDH mutations have also been described in patients with other disorders with high 2-HG levels, e.g. in a rare neurometabolic disorder characterized by supraphysiological levels of 2-HG (2-HG aciduria) (Kranendijk M, Science. 2010 Oct. 15; 330(6002):336).

Hence, the inhibition of IDH mutations and its neomorphic activity is a potential therapeutic treatment option for tumors and other IDH mutation related disorders.

WO02/04425A2 among others relates to benzimidazole derivatives as inhibitors of RNA dependent RNA polymerases.

WO05/014543A1 relates to condensed ring compounds and use thereof as HCV polymerase inhibitors.

WO03/007945A1 inter alia relates to benzimidazole carboxamides as inhibitors of RNA dependent RNA polymerases.

WO01/47883A1 relates to benzimidazole compounds useful as a therapeutic agent for hepatitis C.

EP0531883A1 inter alia relates to amidino-substituted benzimidazole compounds having aggregation-inhibiting effects.

WO2004064925 inter alia relates to acylsulfonamide compounds as inhibitors of RNA dependent RNA polymerases.

WO2007043653 disclosed benzimidazole-5-carboxamide derivatives which can inhibit the sEH activity to increase EETs.

However, the state of the art described above does not describe the specific substituted benzimidazole compounds of general formula (I) of the present invention as defined herein, or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have been found to effectively inhibit mutated isocitrate dehydrogenase 1 (mIDH1 R132H) and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, for example, haematological tumours, solid tumours, and/or metastases thereof, e.g. leukaemias and myelodysplastic syndrome, malignant lymphomas including angioimmunoblastic T-cell lymphomas, head and neck tumours including brain tumours and brain metastases (e.g. anaplastic astrocytoma, diffuse astrocytoma, glioblastoma, oligodendroglioma, secondary glioblastoma multiforme), tumours of the thorax including non-small cell and small cell lung tumours, gastrointestinal tumours including cholangiocarcinoma, endocrine tumours, mammary and other gynaecological tumours, urological tumours including renal, bladder and prostate tumours, skin tumours, and sarcomas including chondrosarcomas, and/or metastases thereof.

DESCRIPTION of the INVENTION

In accordance with a first aspect, the present invention covers compounds of general formula (I):

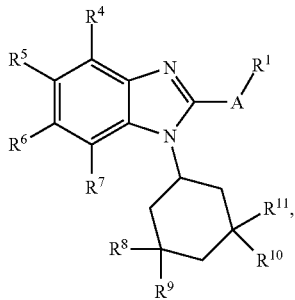

(I)

in which:
A represents a bond or a —CH$_2$— or a —(CH$_2$)$_2$— group, and
R$^5$ represents a group selected from:
—C(O)OH, —C(=O)OR$^{12}$, HOC(=O)—(C$_1$-C$_6$-alkyl)-, R$^{12}$OC(=O)—(C$_1$-C$_6$-alkyl)-, HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)-, —C(=O)N(R$^{13}$)R$^{14}$, R$^{13}$(R$^{14}$)NC(=O)—(C$_1$-C$_6$-alkyl)-, R$^{13}$(R$^{14}$)NC(=O)—(C$_2$-C$_6$-alkenyl)-, R$^{13}$(R$^{14}$)NC(=O)—(C$_1$-C$_6$-alkoxy)- and cyano;
or
A represents a —CH(CH$_3$)— or a —C(CH$_3$)$_2$— group, and
R$^5$ represents a group selected from:
—C(=O)OH, HOC(=O)—(C$_1$-C$_6$-alkyl)-, R$^{12}$OC(=O)—(C$_1$-C$_6$-alkyl)-, HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)-, —C(=O)N(R$^{13}$)R$^{14}$, R$^{13}$(R$^{14}$)NC(=O)—(C$_1$-C$_6$-alkyl)-, R$^{13}$(R$^{14}$)NC(=O)—(C$_2$-C$_6$-alkenyl)-, R$^{13}$(R$^{14}$)NC(=O)—(C$_1$-C$_6$-alkoxy)- and cyano;
R$^1$ represents a phenyl group or a 5-, 6- or 9-membered heteroaryl group,
which phenyl group is optionally substituted with one, two or three substituents, which are, independently of each other, a halogen atom or a group selected from: C$_1$-C$_6$-alkyl, C$_3$-C$_6$-cycloalkyl, C$_1$-C$_6$-alkoxy, C$_3$-C$_6$-cycloalkyloxy, C$_1$-C$_6$-haloalkyl, C$_1$-C$_6$-haloalkoxy and cyano;
and which heteroaryl group is optionally substituted with one, two or three substituents, which are, independently of each other, a halogen atom or a group selected from: C$_1$-C$_3$-alkyl and phenyl;
R$^4$ represents a hydrogen atom or a halogen atom;
R$^6$ represents a hydrogen atom or a halogen atom or a group selected from:
C$_1$-C$_6$-alkyl, C$_1$-C$_6$-alkoxy, C$_3$-C$_6$-cycloalkyl, C$_3$-C$_6$-cycloalkyloxy, C$_1$-C$_6$-haloalkyl, C$_1$-C$_6$-haloalkoxy and cyano;
R$^7$ represents a hydrogen atom;
R$^8$ represents a C$_1$-C$_3$-alkyl group;
R$^9$, R$^{10}$, and R$^{11}$
are independently of each other selected from: hydrogen and C$_1$-C$_3$-alkyl;
R$_{12}$ represents a group selected from:
C$_1$-C$_6$-alkyl and C$_3$-C$_6$-cycloalkyl;
R$^{13}$ and R$^{14}$
are independently of each other selected from: hydrogen and C$_1$-C$_6$-alkyl;
or
R$^{13}$ and R$^{14}$
together with the nitrogen atom to which they are attached form a 4- to 6-membered heterocycloalkyl group;
said 4- to 6-membered heterocycloalkyl group being optionally substituted with one substituent selected from: C$_1$-C$_3$-alkyl, C$_1$-C$_3$-haloalkyl, C$_1$-C$_3$-alkoxy, C$_1$-C$_3$-haloalkoxy, amino, hydroxy, halogen and cyano;
or said 4- to 6-membered heterocycloalkyl group being optionally substituted with two halogen atoms;
or a stereoisomer, a tautomer, an N-oxide, a hydrate, a solvate, a salt thereof, or a mixture of same.

The term "substituted" means that one or more hydrogens on the designated atom or group are replaced with a selection from the indicated group, provided that the designated atom's normal valency under the existing circumstances is not exceeded. Combinations of substituents and/or variables are permissible.

The term "comprising" when used in the specification includes "consisting of".

If it is referred to "as mentioned herein" within the description it is referred to any of the disclosures made within the specification in any of the preceding pages.

The terms as mentioned in the present text have preferably the following meanings:

The term "halogen atom" means a fluorine, chlorine, bromine or iodine atom, preferably a fluorine, chlorine or bromine atom.

The term "C$_1$-C$_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("C$_1$-C$_4$-alkyl"), e.g. a methyl, ethyl, propyl, isopropyl, butyl, sec-butyl isobutyl, or tert-butyl group, more particularly 1, 2 or 3 carbon atoms ("C$_1$-C$_3$-alkyl"), e.g. a methyl, ethyl, n-propyl or isopropyl group.

The term "C$_1$-C$_6$-haloalkyl" means a linear or branched, saturated, monovalent hydrocarbon group in which the term "C$_1$-C$_6$-alkyl" is as defined supra, and in which one or more of the hydrogen atoms are replaced, identically or differently, with a halogen atom. Particularly, said halogen atom is fluorine. Particularly, said group has 1, 2 or 3 carbon atoms ("C$_1$-C$_3$-haloalkyl"), e.g. a fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl group.

The term "C$_1$-C$_6$-alkoxy" means a linear or branched, saturated, monovalent group of formula (C$_1$-C$_6$-alkyl)-O—, in which the term "C$_1$-C$_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof. Particularly, said group has 1, 2 or 3 carbon atoms ("$C_1$-$C_3$-alkoxy"), e.g. a methoxy, ethoxy, n-propoxy, or isopropoxy group.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is fluorine. Particularly, said group has 1, 2 or 3 carbon atoms ("$C_1$-$C_3$-haloalkoxy"), e.g. fluoromethoxy, difluoromethoxy, trifluoromethoxy, 2,2,2-trifluoroethoxy, pentafluoroethoxy or 3,3,3-trifluoropropoxy group.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or a cyclohexyl group.

The term "$C_3$-$C_6$-cycloalkoxy" means a saturated, monovalent, monocyclic group of formula ($C_3$-$C_6$-cycloalkyl)-O—, which contains 3, 4, 5 or 6 carbon atoms ("$C_3$-$C_6$-cycloalkyloxy"), in which the term "$C_3$-$C_6$-cycloalkyl" is defined supra, e.g. a cyclopropyloxy, cyclobutyloxy, cyclopentyloxy or a cyclohexyloxy group.

The term "$C_2$-$C_6$-alkenyl" means a linear or branched, monovalent hydrocarbon group, which contains one double bond, and which has 2, 3, 4, 5 or 6 carbon atoms, particularly 2 or 3 carbon atoms ("$C_2$-$C_3$-alkenyl"). Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl or 1-(1,1-dimethylethypethenyl. Particularly, said group has 2 or 3 carbon atoms ("$C_2$-$C_3$-alkenyl"), e.g. a vinyl or allyl group.

The term "4- to 6-membered heterocycloalkyl" means a monocyclic, saturated heterocycle with 4 to 6 ring atoms in total, which contains one ring nitrogen atom and optionally one further ring heteroatom from the series N, O or S.

Said heterocycloalkyl group, without being limited thereto, can be a 4-membered ring, such as azetidinyl; or a 5-membered ring, such as pyrrolidinyl, imidazolidinyl, pyrazolidinyl, 1,2-oxazolidinyl, 1,3-oxazolidinyl or 1,3-thiazolidinyl; or a 6-membered ring, such as piperidinyl, morpholinyl, thiomorpholinyl, piperazinyl, or 1,2-oxazinanyl for example.

The term "heteroaryl" is understood as meaning a monovalent, monocyclic or bicyclic aromatic ring system having 5, 6 or 9 ring atoms ("a 5-, 6- or 9-membered heteroaryl" group), which contains at least one ring heteroatom and optionally one, two or three further ring heteroatoms from the series N, O and/or S, and which is bound via a ring carbon atom or optionally via a ring nitrogen atom (when allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl.

In general, and unless otherwise mentioned, the heteroarylic or heteroarylenic radicals include all possible isomeric forms thereof, e.g.: tautomers and positional isomers with respect to the point of linkage to the rest of the molecule. Thus, for some illustrative non restricting example, the term pyridinyl includes pyridin-2-yl, pyridin-3-yl and pyridin-4-yl; or the term thienyl includes thien-2-yl and thien-3-yl.

The term "$C_1$-$C_6$", as used throughout this text, e.g. in the context of the definition of "$C_1$-$C_6$-alkyl", "$C_1$-$C_6$-haloalkyl", $C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_6$", as used throughout this text, e.g. in the context of the definition of "$C_3$-$C_6$-cycloalkyl", means a cycloalkyl group having a finite number of carbon atoms of 3 to 8, i.e. 3, 4, 5 or 6 carbon atoms.

When a range of values is listed, it is intended to encompass each value and sub-range within the range.

For example, "$C_1$-$C_6$" is intended to encompass $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$.

For example, "$C_1$-$C_3$" is intended to encompass $C_1$, $C_2$, $C_3$, $C_1$-$C_3$, $C_1$-$C_2$ and $C_2$-$C_3$.

For example, "$C_3$-$C_6$" is intended to encompass $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$.

The compounds of general formula (I) may exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" is to be understood as meaning a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865) is a rapid route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966, 781). A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1993; J. Atzrodt et al., Angew. Chem., Int. Ed. 2007, 46, 7744; K. Matoishi et al., J. Chem. Soc, Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [A. Streitwieser et al., J. Am. Chem. Soc., 1963, 85, 2759; C. L. Perrin, et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res.Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, Calif., Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome P$_{450}$.

In another embodiment the present invention concerns a deuterium-containing compound of general formula (I) having 1, 2, 3 or 4 deuterium atoms, particularly with 1, 2 or 3 deuterium atoms.

In another embodiment the present invention concerns a deuterium-containing compound of general formula (I), comprising one or more groups selected from $CD_3$, $OCD_3$ and benzylic $CD_2$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention optionally contain one or more asymmetric centre, depending upon the location and nature of the various substituents desired. Asymmetric carbon atoms can be present in the (R) or (S) configuration, which can result in racemic mixtures in the case of a single asymmetric centre, and in diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, namely:

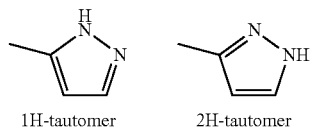

1H-tautomer     2H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides ; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

In a preferred embodiment, the present invention relates to compounds of general formula (I), supra, in which:

A represents a bond or a —CH$_2$— or a —(CH$_2$)$_2$— group, and $R^5$ represents a group selected from:
—C(O)OH, —C(=O)OR$^{12}$, HOC(=O)—($C_1$-$C_6$-alkyl)-, R$^{12}$OC(=O)—($C_1$-$C_6$-alkyl)-, HOC(=O)—($C_2$-$C_6$-alkenyl)-, R$^{12}$OC(=O)—($C_2$-$C_6$-alkenyl)-, HOC(=O)—($C_1$-$C_6$-alkoxy)-, R$^{12}$OC(=O)—($C_1$-$C_6$-alkoxy)- and cyano;

or

A represents a —CH(CH$_3$)—or a —C(CH$_3$)$_2$— group, and $R^5$ represents a group selected from:
—C(=O)OH, HOC(=O)—($C_1$-$C_6$-alkyl), R$^{12}$OC(=O)—($C_1$-$C_6$-alkyl), HOC(=O)—($C_2$-$C_6$-alkenyl)-, R$^{12}$OC(=O)—($C_2$-$C_6$-alkenyl)-, HOC(=O)—($C_1$-$C_6$-alkoxy)-, R$^{12}$OC(=O)—($C_1$-$C_6$-alkoxy)- and cyano;

$R^1$ represents a phenyl group or a 5-, 6- or 9-membered heteroaryl group,
which phenyl group is optionally substituted with one, two or three substituents, which are, independently of each other, a halogen atom or a group selected from: $C_1$-$C_6$-alkyl, $C_3$-$C_6$-cycloalkyl, $C_1$-$C_6$-alkoxy, $C_3$-$C_6$-cycloalkyloxy, $C_1$-$C_6$-haloalkyl, $C_1$-$C_6$-haloalkoxy and cyano;
and which heteroaryl group is optionally substituted with one, two or three substituents, which are, independently of each other, a halogen atom or a group selected from: $C_1$-$C_3$-alkyl and phenyl;

$R^4$ represents a hydrogen atom or a halogen atom;

$R^6$ represents a hydrogen atom or a halogen atom or a group selected from:
$C_1$-$C_6$-alkyl, $C_1$-$C_6$-alkoxy, $C_3$-$C_6$-cycloalkyl, $C_3$-$C_6$-cycloalkyloxy, $C_1$-$C_6$-haloalkyl, $C_1$-$C_6$-haloalkoxy and cyano;

$R^7$ represents a hydrogen atom;

$R^8$ represents a $C_1$-$C_3$-alkyl group;

$R^9$, $R^{10}$, and $R^{11}$
are independently of each other selected from: hydrogen and $C_1$-$C_3$-alkyl;

$R^{12}$ represents a group selected from:
$C_1$-$C_6$-alkyl and $C_3$-$C_6$-cycloalkyl;

or a stereoisomer, a tautomer, an N-oxide, a hydrate, a solvate, a salt thereof, or a mixture of same.

In another preferred embodiment, the present invention relates to compounds of general formula (I), supra, in which:

A represents a bond or a —$CH_2$— or a —$(CH_2)_2$— group, and $R^5$ represents a group selected from:
—C(O)OH, —C(=O)$OR^{12}$, HOC(=O)—($C_1$-$C_3$-alkyl)-, $R^{12}$OC(=O)—($C_1$-$C_3$-alkyl)-, HOC(=O)—($C_2$-$C_3$-alkenyl)-, $R^{12}$OC(=O)—($C_2$-$C_3$-alkenyl)-, HOC(=O)—($C_1$-$C_3$-alkoxy)-, $R^{12}$OC(=O)—($C_1$-$C_3$-alkoxy)- and cyano;

or

A represents a —$CH(CH_3)$— or a —$C(CH_3)_2$— group, and $R^5$ represents a group selected from:
—C(=O)OH, HOC(=O)—($C_1$-$C_3$-alkyl), $R^{12}$OC(=O)—($C_1$-$C_3$-alkyl)-, HOC(=O)—($C_2$-$C_3$-alkenyl)-, $R^{12}$OC(=O)—($C_2$-$C_3$-alkenyl)-, HOC(=O)—($C_1$-$C_3$-alkoxy)-, $R^{12}$OC(=O)—($C_1$-$C_3$-alkoxy)- and cyano;

$R^1$ represents a phenyl group or a 5-, 6- or 9-membered heteroaryl group,
which phenyl group is optionally substituted with one, two or three substituents, which are, independently of each other, a halogen atom or a group selected from: $C_1$-$C_6$-alkyl, $C_3$-$C_6$-cycloalkyl, $C_1$-$C_6$-alkoxy, $C_3$-$C_6$-cycloalkyloxy, $C_1$-$C_3$-haloalkyl, $C_1$-$C_3$-haloalkoxy and cyano;
and which heteroaryl group is optionally substituted with one, two or three substituents, which are, independently of each other, a halogen atom or a group selected from: $C_1$-$C_3$-alkyl and phenyl;

$R^4$ represents a hydrogen atom or a halogen atom;
$R^6$ represents a hydrogen atom or a halogen atom or a group selected from:
$C_1$-$C_3$-alkyl, $C_1$-$C_6$-alkoxy, $C_3$-$C_6$-cycloalkyl, $C_3$-$C_6$-cycloalkyloxy, $C_1$-$C_3$-haloalkyl, $C_1$-$C_3$-haloalkoxy and cyano;
$R^7$ represents a hydrogen atom;
$R^8$ represents a $C_1$-$C_3$-alkyl group;
$R^9$, $R^{10}$, and $R^{11}$
are independently of each other selected from: hydrogen and $C_1$-$C_3$-alkyl;
$R^{12}$ represents a $C_1$-$C_3$-alkyl group;
or a stereoisomer, a tautomer, an N-oxide, a hydrate, a solvate, a salt thereof, or a mixture of same.

In another preferred embodiment, the present invention relates to compounds of general formula (I), supra, in which:

A represents a bond or a —$CH_2$— group, and $R^5$ represents a group selected from:
—C(O)OH, —C(=O)$OR^{12}$, HOC(=O)—($C_1$-$C_2$-alkyl), $R^{12}$OC(=O)—($C_1$-$C_2$-alkyl)- and cyano;

or

A represents a —$CH(CH_3)$— or a —$C(CH_3)_2$— group, and $R^5$ represents a —C(=O)OH group;

$R^1$ represents a phenyl group or a 5- or 9-membered heteroaryl group,
which phenyl group is optionally substituted with one or two substituents, which are, independently of each other, a halogen atom or a group selected from: $C_1$-$C_6$-alkyl, $C_1$-$C_6$-alkoxy, $C_1$-$C_3$-haloalkyl and $C_1$-$C_3$-haloalkoxy;
and which heteroaryl group is optionally substituted with one or two substituents, which are, independently of each other, a halogen atom or a group selected from: $C_1$-$C_3$-alkyl and phenyl;

$R^4$ represents a hydrogen atom or a halogen atom;
$R^6$ represents a hydrogen atom or a group selected from:
$C_1$-$C_3$-alkyl, $C_1$-$C_6$-alkoxy and $C_1$-$C_3$-haloalkoxy;
$R^7$ represents a hydrogen atom;
$R^8$ represents a methyl group;
$R^9$, $R^{10}$, and $R^{11}$
are independently of each other selected from: hydrogen and methyl;
$R^{12}$ represents a $C_1$-$C_3$-alkyl group;
or a stereoisomer, a tautomer, an N-oxide, a hydrate, a solvate, a salt thereof, or a mixture of same.

In another preferred embodiment, the present invention relates to compounds of general formula (I), supra, in which:

A represents a bond or a —$CH_2$— group, and $R^5$ represents a group selected from:
—C(O)OH, —C(=O)$OR^{12}$, HOC(=O)—$(CH_2)_2$—, $R^{12}$OC(=O)—$(CH_2)_2$— and cyano;

or

A represents a —$CH(CH_3)$— or a —$C(CH_3)_2$— group, and $R^5$ represents a —C(=O)OH group;

$R^1$ represents a phenyl group or a 5- or 9-membered heteroaryl group,
which phenyl group is optionally substituted with a fluorine atom or a group selected from: methyl, isopropyl, tert-butyl, isopropoxy, trifluoromethyl and trifluoromethoxy;
and which heteroaryl group is optionally substituted with one or two substituents, which are, independently of each other, a fluorine atom or a group selected from: methyl and phenyl;

$R^4$ represents a hydrogen atom or a fluorine atom;
$R^6$ represents a hydrogen atom or a group selected from:
methyl, methoxy, isopropoxy and 2,2,2-trifluoroethoxy;
$R^7$ represents a hydrogen atom;
$R^8$ represents a methyl group;
$R^9$ is selected from: hydrogen and methyl;
$R^{10}$ and $R^{11}$ both represent methyl groups;
$R^{12}$ represents a methylgroup;
or a stereoisomer, a tautomer, an N-oxide, a hydrate, a solvate, a salt thereof, or a mixture of same.

It is to be understood that the present invention relates to any sub-combination within any embodiment or aspect of the present invention of compounds of general formula (I), supra.

In another preferred embodiment, the present invention relates to compounds of general formula (I), supra, in which:

A represents a bond or a —$CH_2$— or a —$(CH_2)_2$— group, and $R^5$ represents a group selected from —C(O)OH, —C(=O)$OR^{12}$, HOC(=O)—($C_1$-$C_6$-alkyl)-, $R^{12}$OC(=O)—($C_1$-$C_6$-alkyl)-, HOC(=O)—($C_2$-$C_6$-alkenyl)-, $R^{12}$OC(=O)—($C_2$-$C_6$-alkenyl)-, HOC(=O)—($C_1$-$C_6$-alkoxy)-, $R^{12}$OC(=O)—($C_1$-$C_6$-alkoxy)-, —C(=O)N($R^{13}$)$R^{14}$, $R^{13}$($R^{14}$)NC(=O)—($C_1$-$C_6$-alkyl)-, $R^{13}$($R^{14}$)NC(=O)—($C_2$-$C_6$-alkenyl)-, $R^{13}$($R^{14}$)NC(=O)—($C_1$-$C_6$-alkoxy)- and cyano.

In another preferred embodiment, the present invention relates to compounds of general formula (I), supra, in which:

A represents a bond or a —$CH_2$— or a —$(CH_2)_2$— group, and $R^5$ represents a group selected from —C(O)OH, —C(=O)OR$^{12}$, HOC(=O)—(C$_1$-C$_6$-alkyl)-, R$^{12}$OC(=O)—(C$_1$-C$_6$-alkyl), HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)- and cyano.

In another preferred embodiment, the present invention relates to compounds of general formula (I), supra, in which:
A represents a bond or a —CH$_2$— or a —(CH$_2$)$_2$— group, and
$R^5$ represents a group selected from —C(O)OH, —C(=O)OR$^{12}$, HOC(=O)—(C$_1$-C$_3$-alkyl)-, R$^{12}$OC(=O)—(C$_1$-C$_3$-alkyl), HOC(=O)—(C$_2$-C$_3$-alkenyl)-, R$^{12}$OC(=O)—(C$_2$-C$_3$-alkenyl)-, HOC(=O)—(C$_1$-C$_3$-alkoxy)-, R$^{12}$OC(=O)—(C$_1$-C$_3$-alkoxy)- and cyano.

In another preferred embodiment, the present invention relates to compounds of general formula (I), supra, in which:
A represents a bond or a —CH$_2$— group, and
$R^5$ represents a group selected from —C(O)OH, —C(=O)OR$^{12}$, HOC(=O)—(C$_1$-C$_2$-alkyl)-, R$^{12}$OC(=O)—(C$_1$-C$_2$-alkyl)- and cyano.

In another preferred embodiment, the present invention relates to compounds of general formula (I), supra, in which:
A represents a bond or a —CH$_2$— group, and
$R^5$ represents a group selected from —C(O)OH, —C(=O)OR$^{12}$, HOC(=O)—(CH$_2$)$_2$—, R$^{12}$OC(=O)—(CH$_2$)$_2$— and cyano.

In another preferred embodiment, the present invention relates to compounds of general formula (I), supra, in which:
A represents a —CH(CH$_3$)— or a —C(CH$_3$)$_2$— group, and
$R^5$ represents a group selected from —C(=O)OH, HOC(=O)—(C$_1$-C$_6$-alkyl)-, R$^{12}$OC(=O)—(C$_1$-C$_6$-alkyl), HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)-, —C(=O)N(R$^{13}$)R$^{14}$, R$^{13}$(R$^{14}$)NC(=O)—(C$_1$-C$_6$-alkyl)-, R$^{13}$(R$^{14}$)NC(=O)—(C$_2$-C$_6$-alkenyl)-, R$^{13}$(R$^{14}$)NC(=O)—(C$_1$-C$_6$-alkoxy)- and cyano.

In another preferred embodiment, the present invention relates to compounds of general formula (I), supra, in which:
A represents a —CH(CH$_3$)— or a —C(CH$_3$)$_2$— group, and
$R^5$ represents a group selected from —C(=O)OH, HOC(=O)—(C$_1$-C$_6$-alkyl)-, R$^{12}$OC(=O)—(C$_1$-C$_6$-alkyl), HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)- and cyano.

In another preferred embodiment, the present invention relates to compounds of general formula (I), supra, in which:
A represents a —CH(CH$_3$)— or a —C(CH$_3$)$_2$— group, and
$R^5$ represents a group selected from —C(=O)OH, HOC(=O)—(C$_1$-C$_3$-alkyl)-, R$^{12}$OC(=O)—(C$_1$-C$_3$-alkyl), HOC(=O)—(C$_2$-C$_3$-alkenyl)-, R$^{12}$OC(=O)—(C$_2$-C$_3$-alkenyl)-, HOC(=O)—(C$_1$-C$_3$-alkoxy)-, R$^{12}$OC(=O)—(C$_1$-C$_3$-alkoxy)- and cyano.

In another preferred embodiment, the present invention relates to compounds of general formula (I), supra, in which
A represents a —CH(CH$_3$)— or a —C(CH$_3$)$_2$— group, and
$R^5$ represents a —C(=O)OH group.

In another preferred embodiment, the present invention relates to compounds of general formula (I), supra, in which
A represents a bond or a —CH$_2$— or a —(CH$_2$)$_2$— group.

In another preferred embodiment, the present invention relates to compounds of general formula (I), supra, in which
A represents a bond or a —CH$_2$— group.

In another preferred embodiment, the present invention relates to compounds of general formula (I), supra, in which
A represents a bond.

In another preferred embodiment, the present invention relates to compounds of general formula (I), supra, in which
A represents a —CH$_2$— group.

In another preferred embodiment, the present invention relates to compounds of general formula (I), supra, in which
A represents a —CH(CH$_3$)— or a —C(CH$_3$)$_2$— group.

In another preferred embodiment, the present invention relates to compounds of general formula (I), supra, in which:
$R^1$ represents a phenyl group or a 5-, 6- or 9-membered heteroaryl group, which phenyl group is optionally substituted with one, two or three substituents, which are, independently of each other, a halogen atom or a group selected from C$_1$-C$_6$-alkyl, C$_3$-C$_6$-cycloalkyl, C$_1$-C$_6$-alkoxy, C$_3$-C$_6$-cycloalkyloxy, C$_1$-C$_6$-haloalkyl, C$_1$-C$_6$-haloalkoxy and cyano; and which heteroaryl group is optionally substituted with one, two or three substituents, which are, independently of each other, a halogen atom or a group selected from C$_1$-C$_3$-alkyl and phenyl.

In another preferred embodiment, the present invention relates to compounds of general formula (I), supra, in which:
$R^1$ represents a phenyl group or a 5-, 6- or 9-membered heteroaryl group, which phenyl group is optionally substituted with one, two or three substituents, which are, independently of each other, a halogen atom or a group selected from C$_1$-C$_6$-alkyl, C$_3$-C$_6$-cycloalkyl, C$_1$-C$_6$-alkoxy, C$_3$-C$_6$-cycloalkyloxy, C$_1$-C$_3$-haloalkyl, C$_1$-C$_3$-haloalkoxy and cyano; and which heteroaryl group is optionally substituted with one, two or three substituents, which are, independently of each other, a halogen atom or a group selected from C$_1$-C$_3$-alkyl and phenyl.

In another preferred embodiment, the present invention relates to compounds of general formula (I), supra, in which:
$R^1$ represents a phenyl group or a 5- or 9-membered heteroaryl group, which phenyl group is optionally substituted with one or two substituents, which are, independently of each other, a halogen atom or a group selected from C$_1$-C$_6$-alkyl, C$_1$-C$_6$-alkoxy, C$_1$-C$_3$-haloalkyl and C$_1$-C$_3$-haloalkoxy; and which heteroaryl group is optionally substituted with one or two substituents, which are, independently of each other, a halogen atom or a group selected from C$_1$-C$_3$-alkyl and phenyl.

In another preferred embodiment, the present invention relates to compounds of general formula (I), supra, in which:
$R^1$ represents a phenyl group or a 5- or 9-membered heteroaryl group, which phenyl group is optionally substituted with a fluorine atom or a group selected from methyl, isopropyl, tert-butyl, isopropoxy, trifluoromethyl and trifluoromethoxy; and which heteroaryl group is optionally substituted with one or two substituents, which are, independently of each other, a fluorine atom or a group selected from methyl and phenyl.

In another preferred embodiment, the present invention relates to compounds of general formula (I), supra, in which
$R^4$ represents a hydrogen atom or a halogen atom.

In another preferred embodiment, the present invention relates to compounds of general formula (I), supra, in which
$R^4$ represents a hydrogen atom or a fluorine atom.

In another preferred embodiment, the present invention relates to compounds of general formula (I), supra, in which:
$R^6$ represents a hydrogen atom or a halogen atom or a group selected from C$_1$-C$_6$-alkyl, C$_1$-C$_6$-alkoxy, C$_3$-C$_6$-cycloalkyl, C$_3$-C$_6$-cycloalkyloxy, C$_1$-C$_6$-haloalkyl, C$_1$-C$_6$-haloalkoxy and cyano.

In another preferred embodiment, the present invention relates to compounds of general formula (I), supra, in which:

$R^6$ represents a hydrogen atom or a halogen atom or a group selected from $C_1$-$C_3$-alkyl, $C_1$-$C_6$-alkoxy, $C_3$-$C_6$-cycloalkyl, $C_3$-$C_6$-cycloalkyloxy, $C_1$-$C_3$-haloalkyl, $C_1$-$C_3$-haloalkoxy and cyano.

In another preferred embodiment, the present invention relates to compounds of general formula (I), supra, in which:
$R^6$ represents a hydrogen atom or a group selected from $C_1$-$C_3$-alkyl, $C_1$-$C_6$-alkoxy and $C_1$-$C_3$-haloalkoxy.

In another preferred embodiment, the present invention relates to compounds of general formula (I), supra, in which:
$R^6$ represents a hydrogen atom or a group selected from methyl, methoxy, isopropoxy and 2,2,2-trifluoroethoxy.

In another preferred embodiment, the present invention relates to compounds of general formula (I), supra, in which $R^8$ represents a $C_1$-$C_3$-alkyl group.

In another preferred embodiment, the present invention relates to compounds of general formula (I), supra, in which $R^8$ represents a methyl group.

In another preferred embodiment, the present invention relates to compounds of general formula (I), supra, in which $R^9$, $R^{10}$, and $R^{11}$ are independently of each other selected from hydrogen and
$C_1$-$C_3$-alkyl.

In another preferred embodiment, the present invention relates to compounds of general formula (I), supra, in which $R^9$, $R^{10}$, and $R^{11}$ are independently of each other selected from: hydrogen and methyl.

In another preferred embodiment, the present invention relates to compounds of general formula (I), supra, in which $R^{12}$ represents a group selected from $C_1$-$C_6$-alkyl and $C_3$-$C_6$-cycloalkyl.

In another preferred embodiment, the present invention relates to compounds of general formula (I), supra, in which $R^{12}$ represents a group selected from $C_1$-$C_6$-alkyl.

In another preferred embodiment, the present invention relates to compounds of general formula (I), supra, in which $R^{12}$ represents a group selected from $C_1$-$C_3$-alkyl.

In another preferred embodiment, the present invention relates to compounds of general formula (I), supra, in which $R^{12}$ represents a methyl group.

In another preferred embodiment, the present invention relates to compounds of general formula (I), supra, in which:
$R^{13}$ and $R^{14}$ are independently of each other selected from hydrogen and $C_1$-$C_6$-alkyl; or
$R^{13}$ and $R^{14}$ together with the nitrogen atom to which they are attached form a 4- to 6-membered heterocycloalkyl group, said 4- to 6-membered heterocycloalkyl group being optionally substituted with one substituent selected from $C_1$-$C_3$-alkyl, $C_1$-$C_3$-haloalkyl, $C_1$-$C_3$-alkoxy, $C_1$-$C_3$-haloalkoxy, amino, hydroxy, halogen and cyano; or said 4- to 6-membered heterocycloalkyl group being optionally substituted with two halogen atoms.

In another preferred embodiment, the present invention relates to compounds of general formula (I), supra, in which $R^{13}$ and $R^{14}$ are independently of each other selected from hydrogen and $C_1$-$C_6$-alkyl.

In another preferred embodiment, the present invention relates to compounds of general formula (I), supra, in which:
$R^{13}$ and $R^{14}$ together with the nitrogen atom to which they are attached form a 4- to 6-membered heterocycloalkyl group, said 4- to 6-membered heterocycloalkyl group being optionally substituted with one substituent selected from $C_1$-$C_3$-alkyl, $C_1$-$C_3$-haloalkyl, $C_1$-$C_3$-alkoxy, $C_1$-$C_3$-haloalkoxy, amino, hydroxy, halogen and cyano; or said 4- to 6-membered heterocycloalkyl group being optionally substituted with two halogen atoms.

It is to be understood that the present invention relates also to any combination of the preferred embodiments described above.

More particularly still, the present invention covers example compounds of general formula (I) which are disclosed in the Example section of this text, infra.

In accordance with another aspect, the present invention covers methods of preparing compounds of the present invention, said methods comprising the steps as described in the Experimental Section herein.

In accordance with a further aspect, the present invention covers intermediate compounds which are useful for the preparation of the compounds of general formula (I), supra.

Particularly, the inventions covers intermediate compounds of general formula (II):

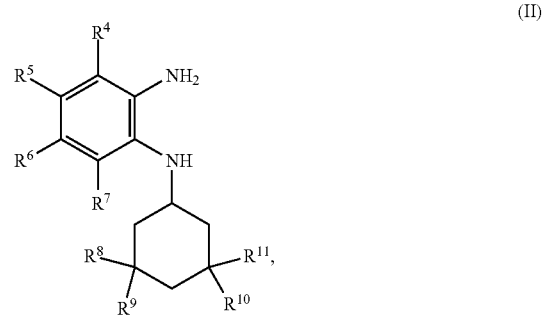

in which $R^4$, $R^5$, $R^6$, $R^7$, $R^8$, $R^9$, $R^{10}$ and $R^{11}$ are as defined for the compounds of general formula (I), supra.

More particularly still, the present invention covers the intermediate compounds which are disclosed in the Example section of this text, infra.

In accordance with a further aspect, the present invention covers the use of the intermediate compounds of general formula (II):

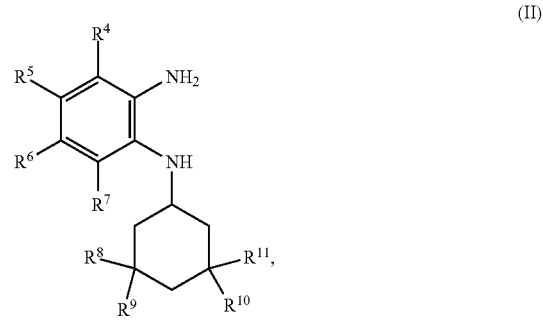

in which $R^4$, $R^5$, $R^6$, $R^7$, $R^8$, $R^9$, $R^{10}$ and $R^{11}$ are as defined for the compounds of general formula (I), supra, for the preparation of a compound of general formula (I) as defined supra.

In accordance with a further aspect, the present invention relates to compounds of general formula (I), as decribed supra, or a stereoisomer, a tautomer, an N-oxide, a hydrate, a solvate, or a salt thereof, particularly a pharmaceutically acceptable salt thereof, or a mixture of same, for use in the treatment or prophylaxis of a disease.

In accordance with a further aspect, the present invention relates to a pharmaceutical composition comprising a compound of general formula (I), as decribed supra, or a stereoisomer, a tautomer, an N-oxide, a hydrate, a solvate, or a salt thereof, particularly a pharmaceutically acceptable salt thereof, or a mixture of same, and a pharmaceutically acceptable diluent or carrier.

Particularly, the pharmaceutical combination comprises:
one or more first active ingredients selected from a compound of general formula (I), as decribed supra, and
one or more second active ingredients selected from chemotherapeutic anti-cancer agents (see below).

In accordance with a further aspect, the present invention relates to use of a compound of general formula (I), as described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

In accordance with a further aspect, the present invention relates to use of a compound of general formula (I), as described supra, or a stereoisomer, a tautomer, an N-oxide, a hydrate, a solvate, or a salt thereof, particularly a pharmaceutically acceptable salt thereof, or a mixture of same, for the preparation of a medicament for the prophylaxis or treatment of a disease.

The disease as mentioned before is in particular a disease of uncontrolled cell growth, proliferation and/or survival, an inappropriate cellular immune response, or an inappropriate cellular inflammatory response, particularly in which the disease of uncontrolled cell growth, proliferation and/or survival, inappropriate cellular immune response, or inappropriate cellular inflammatory response is a haematological tumour, a solid tumour and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

EXPERIMENTAL SECTION

The following table 1 lists the abbreviations used in this paragraph and in the Intermediate Examples and Examples section as far as they are not explained within the text body. NMR peak forms are stated as they appear in the spectra, possible higher order effects have not been considered. Chemical names were generated using the ICS naming tool of ACD labs. In some cases generally accepted names of commercially available reagents were used in place of ICS naming tool generated names.

TABLE 1

| Abbreviation | Meaning |
| --- | --- |
| br. | broad signal in NMR |
| br. s. | broad singlet |
| $CDCl_3$ | deuterated trichloromethane |
| DCM | dichloromethane |
| DMF | N,N-dimethylformamide |
| d | doublet |
| dd | doublet of doublets |
| DMSO | dimethyl sulfoxide |
| DMSO-$d_6$ | deuterated dimethyl sulfoxide |
| ESI | electrospray ionization |
| EtOH | ethanol |

TABLE 1-continued

| Abbreviation | Meaning |
| --- | --- |
| h | hour(s) |
| HCl | hydrochloric acid |
| $HClO_4$ | perchloric acid |
| HPLC, LC | high performance liquid chromatography |
| m | multiplet |
| min | minute(s) |
| MS | mass spectroscopy |
| MeOH | methanol |
| $NH_4Cl$ | ammonium chloride |
| NMR | nuclear magnetic resonance |
| $R_t$ | retention time |
| rt | room temperature |
| s | singlet |
| sept | septet |
| t | triplet |
| THF | tetrahydrofurane |
| UPLC | ultra performance liquid chromatography |

Other abbreviations have their meanings customary per se to the skilled person. The various aspects of the invention described in this application are illustrated by the following examples which are not meant to limit the invention in any way.

Syntheses of Compounds (Overview)

The following schemes and general procedures illustrate general synthetic routes to the compounds of general formula (I) of the invention and are not intended to be limiting. It is obvious to the person skilled in the art that the order of transformations as exemplified in Schemes 1 to 3 can be modified in various ways. The order of transformations exemplified in Schemes 1 to 3 is therefore not intended to be limiting. In addition, interconversion of substituents, for example of residues $R^1$, $R^4$, $R^5$, $R^6$, $R^7$ and A can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts, *Protective Groups in Organic Synthesis*, 3rd edition, Wiley 1999).

Scheme 1:

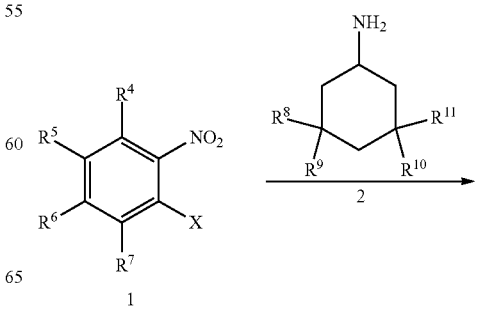

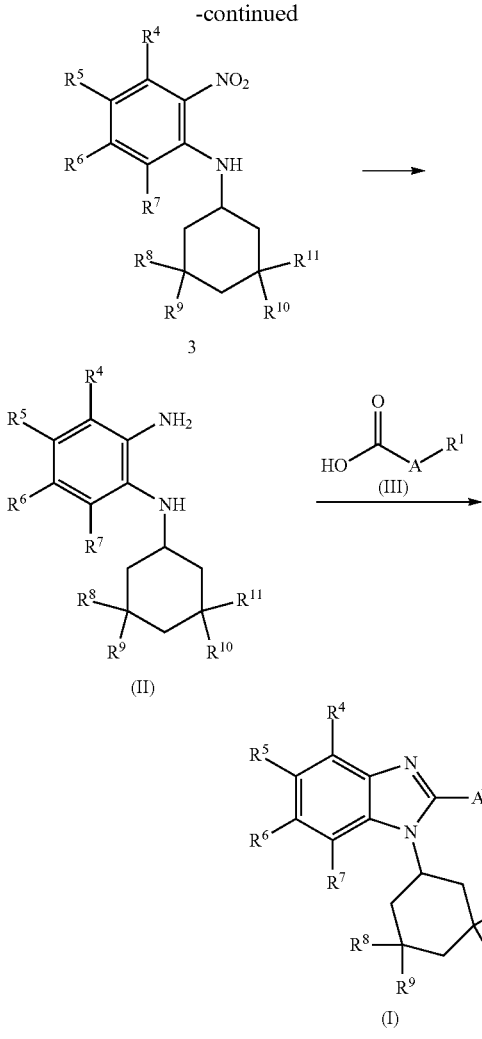

in which $R^1$, $R^4$, $R^5$, $R^6$, $R^7$, $R^8$, $R^9$, $R^{10}$, $R^{11}$ and A are as defined supra, and X represents a halogen atom.

Suitably functionalized diamines of general formula (II) may be reacted with carboxylic acids of general formula (III) in the presence of an amide coupling/dehydration agent. For amide coupling/dehydration, all processes that are known to the person skilled in the art may be applied. Diamines of general formula (II) may be reacted with carboxylic acids of general formula (III) in a suitable solvent such as for example ethyl acetate or DMF and in the presence of for example 2,4,6-tripropyl-1,3,5,2,4,6-trioxatriphosphinane 2,4,6-trioxide in a pressure vial at temperatures between 0° C. and 150° C., typically at 100° C. The coupling and following dehydration could also be run in two separate steps. Activation of carboxylic acids of general formula (III) with for example 1,1'-carbonyldiimidazole may be followed by reaction with diamines of general formula (II) to give the corresponding amide intermediates. These amide intermediates may be dehydrated (cyclized) with acids such as for example acetic acid at temperatures between rt and the boiling point of the solvent, typically at 110° C.

Diamines of general formula (II) in turn may be obtained from nitroanilines of general formula 3 by reduction. For reduction, all processes that are known to the person skilled in the art may be applied. Nitroanilines of general formula 3 may be hydrogenated under an atmosphere of hydrogen at pressures ranging from 1 bar to 100 bar in a suitable solvent such as for example ethyl acetate, tetrahydrofurane, methanol or ethanol and in the presence of a metal catalyst such as for example palladium on charcoal at temperatures between 0° C. and the boiling point of the solvent, typically at room temperature. The addition of a suitable acid such as for example hydrochloric acid or acetic acid may be necessary. Alternatively, nitroanilines of general formula 3 may be reduced with iron/ammonium chloride or with tin(II) chloride in a suitable solvent such as for example water, methanol or ethanol or mixtures thereof at temperatures between room temperature and the boiling point of the solvent, typically at 70° C.

Nitroanilines of general formula 3 can be obtained from nitroarenes of general formula 1 by nucleophilic substitution with amines of general formula 2 in a suitable solvent such as for example tetrahydrofurane and in the presence of a suitable base such as for example potassium carbonate or triethylamine at temperatures between room temperature and the boiling point of the solvent, typically at 50-70° C. Instead of using amines of general formula 2 their corresponding ammonium salts can be used as well. Nitroarenes of general formula 1 and amines of general formula 2 or their corresponding ammonium salts are either commercially available, known compounds or may be formed from known compounds by known methods by a person skilled in the art.

Scheme 2:

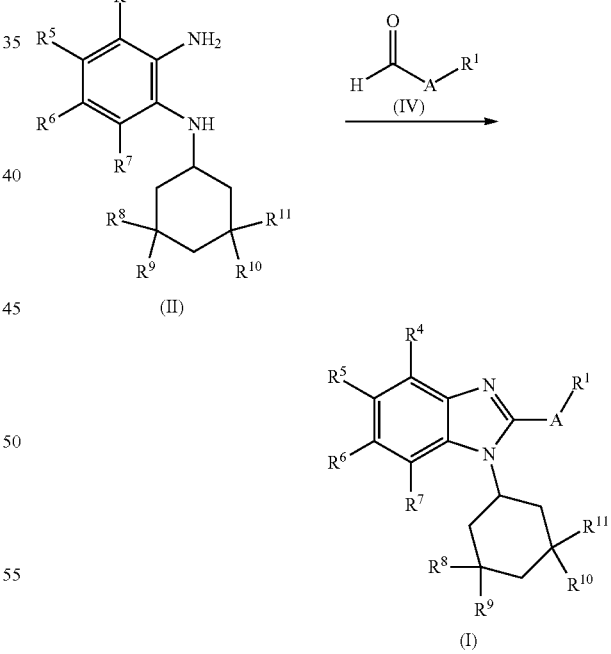

in which $R^1$, $R^4$, $R^5$, $R^6$, $R^7$, $R^8$, $R^9$, $R^{10}$, $R^{11}$ and A are as defined supra.

An alternative method for the synthesis of compounds of general formula (I) is depicted in scheme 2.

Suitably functionalized diamines of general formula (II) may be reacted with aldehydes of general formula (IV) in a suitable solvent such as for example tetrahydrofurane or water or a mixture thereof and in the presence of a sulfite source such as for example sodium sulfite at temperatures between 0° C. and the boiling point of the solvent, typically at 65° C.

Diamines of general formula (II) and aldehydes of general formula (IV) are either commercially available, known compounds or may be formed from known compounds by known methods by a person skilled in the art.

Scheme 3:

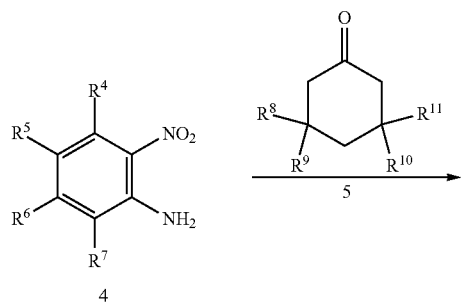

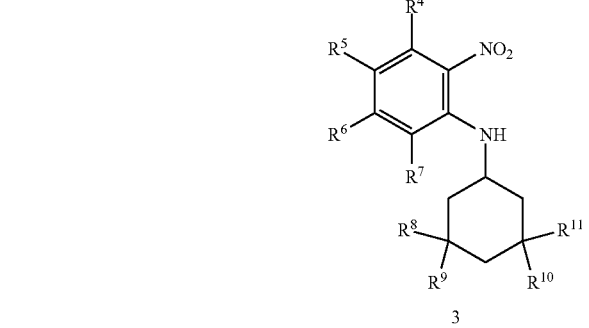

in which $R^4$, $R^5$, $R^6$, $R^7$, $R^8$, $R^9$, $R^{10}$ and $R^{11}$ are as defined supra.

An alternative route to nitroanilines of general formula 3 via reductive amination is outlined in Scheme 3. Nitroanilines of general formula 4 may be reacted with cyclohexanones of general formula 5 in a suitable solvent such as for example dichloromethane or dichloroethane and in the presence of a reducing agent such as for example sodium borohydride or sodium triacetoxyborohydride at temperatures between 0° C. and the boiling point of the solvent, typically at room temperature. It might be necessary to add an acid such as for example trifluoroacetic acid to the reaction mixture.

Nitroanilines of general formula 4 and cyclohexanones of general formula 5 are either commercially available, known compounds or may be formed from known compounds by known methods by a person skilled in the art.

In accordance with an embodiment, the present invention also relates to a method of preparing a compound of general formula (I) as defined supra, said method comprising the step of allowing an intermediate compound of general formula (II):

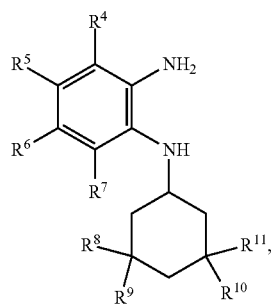

in which $R^4$, $R^5$, $R^6$, $R^7$, $R^8$, $R^9$, $R^{10}$ and $R^{11}$ are as defined for the compound of general formula (I), supra,
to react with a compound of general formula (III):

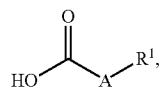

in which $R^1$ and A are as defined as for the compound of general formula (I), supra,
thereby giving a compound of general formula (I):

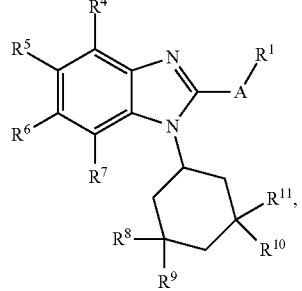

in which $R^1$, $R^4$, $R^5$, $R^6$, $R^7$, $R^8$, $R^9$, $R^{10}$, $R^{11}$ and A are as defined for the compound of general formula (I), supra.

In accordance with another embodiment, the present invention also relates to a method of preparing a compound of general formula (I) as defined supra, said method comprising the step of allowing an intermediate compound of general formula (II):

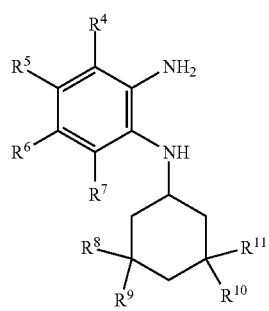

in which $R^4$, $R^5$, $R^6$, $R^7$, $R^8$, $R^9$, $R^{10}$ and $R^{11}$ are as defined for the compound of general formula (I), supra,
to react with a compound of general formula (IV):

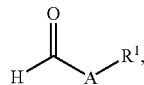
(IV)

in which $R^1$ and A are as defined as for the compound of general formula (I), supra,
thereby giving a compound of general formula (I):

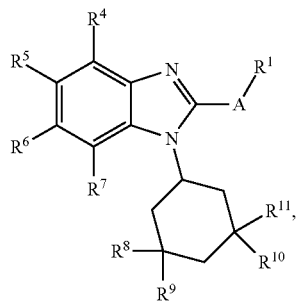
(I)

in which $R^1$, $R^4$, $R^5$, $R^6$, $R^7$, $R^8$, $R^9$, $R^{10}$, $R^{11}$ and A are as defined for the compound of general formula (I), supra.

General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ES−).

In most of the cases method A is used. If not, it is indicated.

UPLC-MS Method A

Instrument: Waters Acquity UPLC-MS SQD 3001; Column: Acquity UPLC BEH C18 1.7 50×2.1 mm; Eluent A: water+0.1% formic acid, Eluent B: acetonitrile; Gradient: 0-1.6 min 1-99% B, 1.6-2.0 min 99% B; Flow rate 0.8 mL/min; Temperature: 60° C.; Injection: 2 μL; DAD scan: 210-400 nm.

UPLC-MS Method B

Instrument: Waters Acquity UPLC-MS SQD 3001; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 mL/min; Temperature: 60° C.; Injection: 2 μL; DAD scan: 210-400 nm; ELSD.

UPLC-MS Method D

Instrument: Waters Acquity UPLC-MS ZQ4000; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 mL/min; Temperature: 60° C.; Injection: 2 μL; DAD scan: 210-400 nm; ELSD.

UPLC-MS Method E

Instrument: Waters Acquity UPLC-MS ZQ2000; Column: Acquity UPLC BEH C18 1.7 50×2.1 mm; Eluent A: water+0.1% formic acid , Eluent B: acetonitrile; Gradient: 0-1.6 min 1-99% B, 1.6-2.0 min 99% B; Flow rate 0.8 mL/min; Temperature: 60° C.; Injection: 1 μL; DAD scan: 210-400 nm; ELSD.

UPLC-MS Method F

Instrument: Waters Acquity UPLC-MS ZQ2000; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 mL/min; Temperature: 60° C.; Injection: 1 μL; DAD scan: 210-400 nm; ELSD.

UPLC-MS Method G

Instrument: Waters Acquity UPLC-MS; Column: XBridge BEH $C_{18}$ 2.5 μm 2.1×50 mm; Eluent A: 10 mM ammonium bicarbonate pH 10, Eluent B: acetonitrile; Gradient: 2-98% B in 0.80 min, hold at 98% B to 1.30 min; Flow rate 0.8 mL/min; Detection: Waters Acquity Autosampler (UPLC LG 500 nm).

UPLC-MS Method H

Instrument: Waters Acquity UPLC-MS; Column: XBridge BEH $C_{18}$ 2.5 μm 2.1×50 mm; Eluent A: 10 mM ammonium bicarbonate pH 10, Eluent B: acetonitrile; Gradient: 2-98% B in 4.00 min, hold at 98% B to 4.70 min; Flow rate 0.8 mL/min; Detection: Waters Acquity Autosampler (UPLC LG 500 nm).

NMR peak forms are stated as they appear in the spectra, possible higher order effects have not been considered.

The obtained benzimidazoles of general formula (I) may be chiral and may be separated into their diastereomers and/or enantiomers by chiral HPLC.

INTERMEDIATES

Intermediate 1-1

(±) methyl 3-amino-4-{[(trans)-3,3,5-trimethylcyclohexyl]amino}benzoate and (±) methyl 3-amino-4-{[(cis)-3,3,5-trimethylcyclohexyl]amino}benzoate

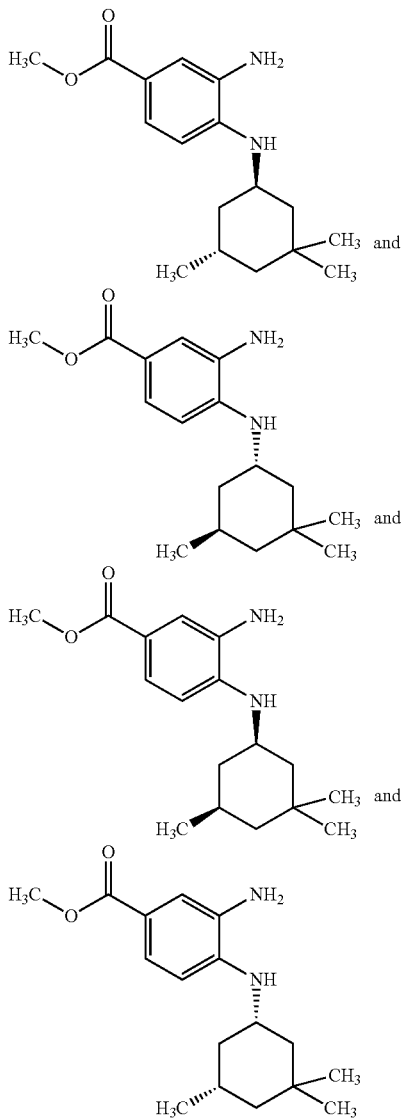

Step 1: methyl 3-nitro-4-[(3,3,5-trimethylcyclohexyl)amino]benzoate 22.7 g (114 mmol) Methyl-4-fluoro-3-nitrobenzoate (commercially available) and 16.1 g (114 mmol) 3,3,5-trimethylcyclohexanamine (mixture of stereoisomers, commercially available) were given in 460 mL tetrahydrofurane. After addition of 17.34 g (125 mmol) potassium carbonate the reaction mixture was heated at 50° C. for 45 hours. The solids were filtered off via a glass fibre filter, washed with ethyl acetate and discarded. The filtrate was diluted with water (200 mL) and ethyl acetate (450 mL). After vigorous stirring for 15 min the organic phase was separated. The aqueous phase was washed with ethyl acetate (250 mL). The combined organic extracts were washed with water (150 mL) and brine (150 mL). After drying (sodium sulfate) the solvent was evaporated yielding 35.9 g (93%) of an orang-eyellow solid (mixture of stereoisomers) which was used without further purification in the next step.

UPLC-MS: $R_t$=1.67 min; m/z=321 (ES+, M+1).

Step 2: methyl 3-amino-4-{[(trans)-3,3,5-trimethylcyclohexyl]amino}benzoate and methyl 3-amino-4-{[(cis)-3,3,5-trimethylcyclohexyl]amino}benzoate 15 g (46.8 mmol) Methyl 3-nitro-4-[(3,3,5-trimethylcyclohexyl)amino]benzoate were dissolved in ethyl acetate (706 mL). After addition of 0.98 g (9.2 mmol) palladium on carbon the reaction mixture was stirred under a hydrogen atmosphere for seven hours at room temperature. The catalyst was filtered off via a glass fibre filter and washed with ethyl acetate. After evaporation of the solvent the residue was purified by column chromatography (Biotage, eluents: hexane/ethyl acetate) yielding 0.6 g (4.2%) of the trans diastereomer (as racemate) and 9.99 g (70%) of the cis diastereomer (as racemate).

Trans compound: $^1$H-NMR (400 MHz, DMSO-$d_6$): δ [ppm]=0.81-0.97 (m, 10H), 1.21-1.33 (m, 2H), 1.38 (d, 1H), 1.62 (d, 1H), 1.72 (d, 1H), 1.99-2.13 (m, 1H), 3.68-3.78 (br., 4H), 4.74 (br., 3H), 6.42 (d, 1H), 7.14-7.24 (m, 2H).

Cis compound: $^1$H-NMR (400 MHz, DMSO-$d_6$): δ [ppm]= 0.68-1.06 (m, 12H), 1.35 (d, 1H), 1.62-1.79 (m, 2H), 1.91-2.03 (m, 1H), 3.42-3.57 (m, 1H), 3.70 (s, 3H), 4.72 (s, 2H), 4.82 (d, 1H), 6.45 (d, 1H), 7.11-7.22 (m, 2H).

Intermediate 1-2

(±) methyl 5-amino-2-methyl-4-{[(cis)-3,3,5-trimethylcyclohexyl]amino}benzoate

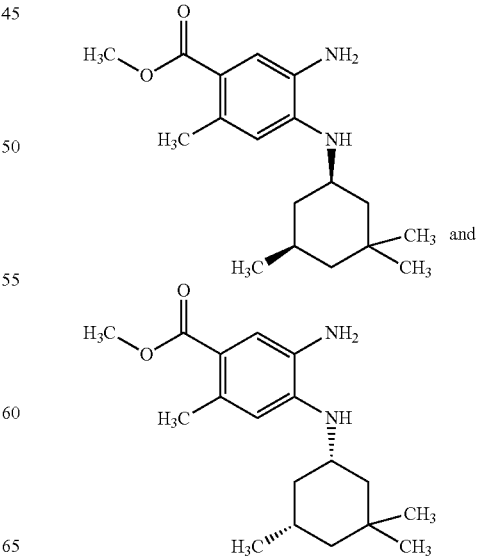

Step 1: (±) methyl 2-methyl-5-nitro-4-{[(cis)-3,3,5-trimethylcyclohexyl]amino}benzoate and (±) methyl 2-methyl-5-nitro-4-{[(trans)-3,3,5-trimethylcyclohexyl]amino}benzoate In analogy to step 1 of intermediate 1-1: Methyl 4-fluoro-2-methyl-5-nitrobenzoate (CAS No. [1163287-01-1]; 5.14 g, 24.1 mmol) was reacted with potassium carbonate (1.10 eq., 3.67 g, 26.5 mmol) and 3,3,5-trimethylcyclohexanamine (mixture of stereoisomers, commercially available; 1.00 eq., 3.41 g, 24.1 mmol) in THF (154 mL) at rt for 20 h to give the title compound (8.51 g, quant.) as a racemic mixture of cis diastereomer and trans diastereomer (ca 7:1) which was not further purified. UPLC-MS (ESI+): [M+H]$^+$=335; R$_t$=1.71/1.72 min.

Step 2: (±) methyl 5-amino-2-methyl-4-{[(cis)-3,3,5-trimethylcyclo-hexyl]amino}benzoate In analogy to step 2 of intermediate 1-1: A mixture of (±) methyl 2-methyl-5-nitro-4-{[(cis)-3,3,5-trimethylcyclohexyl]amino}benzoate and (±) methyl 2-methyl-5-nitro-4-{[(trans)-3,3,5-trimethylcyclohexyl]amino}benzoate (ca 7:1; 8.51 g, 24.2 mmol) from step 1 was hydrogenated with palladium on carbon (10 wt %; 0.25 eq., 643 mg, 6.04 mmol) and hydrogen gas in ethyl acetate (400 mL) at rt overnight to give after purification by flash chromatography (SiO$_2$-hexane/ethyl acetate) the title compound (3.7 g, 50%) as racemic cis diastereomer.

$^1$H-NMR (400 MHz, DMSO-d6): δ [ppm]=0.66-0.81 (m, 2H), 0.88 (d, 3H), 0.93 (s, 3H), 0.96-1.02 (m, 4H), 1.35-1.38 (m, 1H), 1.65-1.78 (m, 2H), 1.95-1.99 (m, 1H), 2.38 (s, 3H), 3.46-3.55 (m, 1H), 3.69 (s, 3H), 4.51 (br. s., 2H), 4.75 (d, 1H), 6.28 (s, 1H), 7.15 (s, 1H).

UPLC-MS (ESI+): [M+H]$^+$=305; R$_t$=1.49 min (Method D).

Intermediate 1-3 methyl 3-amino-2-fluoro-4-[(3,3,5,5-tetramethylcyclohexyl)amino]benzoate

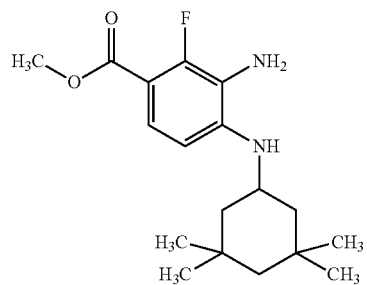

Step 1: 4-bromo-3-fluoro-2-nitro-N-(3,3,5,5-tetramethylcyclohexyl)aniline

A mixture of 4-bromo-3-fluoro-2-nitroaniline (CAS No. [886762-75-0]; 5.80 g, 24.7 mmol) and 3,3,5,5-tetramethylcyclohexanone (CAS No. [14376-79-5]; 1.00 eq., 3.81 g, 24.7 mmol) in dichloromethane (60 mL) was treated dropwise with trifluoroacetic acid (20 mL) and stirred at rt for 5 minutes upon which sodium triacetoxyborohydride ([56553-60-7]; 1.5 eq., 7.85 g, 37.0 mmol) was added in portions to the clear solution and stirring at rt was continued for 2 days. The ice-cooled reaction mixture was quenched with an aqueous ammonia solution (25%, 22 mL) and partitioned between water and dichloromethane. The phases were separated and the aqueous phase extracted twice with dichloromethane. The combined organic layers were dried with magnesium sulfate and concentrated in vacuo. The obtained material was purified by flash chromatography (SiO$_2$-hexane/ethyl acetate) to give the title compound (4.7 g, 48%) along with reisolated 4-bromo-3-fluoro-2-nitroaniline (2.7 g, 47%).

$^1$H-NMR (300 MHz, DMSO-d$_6$): δ [ppm]=0.90 (s, 6H), 1.06-1.15 (m, 9H), 1.23-1.27 (m, 1H), 1.66-1.70 (m, 2H), 3.71-3.84 (m, 1H), 5.98 (d, 1H), 6.81 (dd, 1H), 6.85 (d, 1H), 7.68 (dd, 1H).

UPLC-MS (ESI+): [M+H]$^+$=373/375; R$_t$=1.78 min (Br isotope pattern).

Step 2: methyl 3-amino-2-fluoro-4-[(3,3,5,5-tetramethylcyclohexyl)amino]benzoate A solution of 4-bromo-3-fluoro-2-nitro-N-(3,3,5,5-tetramethylcyclohexyl)aniline (2.08 g, 5.57 mmol) from step 1 in methanol (56 mL) was placed into a steel autoclave under argon atmosphere. 1,1'-Bis(diphenylphosphino)ferrocene-palladium(II) dichloride dichloromethane complex (CAS No. [95464-05-4]; 0.200 eq., 910 mg, 1.11 mmol) and potassium acetate (4.00 eq., 2.19 g, 22.3 mmol) were added and the mixture was purged 3 times with carbon monoxide. The mixture was stirred for 30 minutes at 20° C. under a carbon monoxide pressure of ca 12.6 bar. The autoclave was set under vacuum again, then a carbon monoxide pressure of ca 12 bar was applied and the mixture heated to 100° C. for 21 h, yielding a maximum pressure of ca 13.3 bar. The reaction was cooled to rt, the pressure released and the reaction mixture concentrated in vacuo. The obtained crude product was purified by flash chromatography (SiO$_2$-hexane/ethyl acetate) to give the desired ester (805 mg, 44%).

$^1$H-NMR (300 MHz, DMSO-d$_6$): δ [ppm]=0.91 (s, 6H), 0.97-1.10 (m, 9H), 1.25-1.29 (m, 1H), 1.70-1.74 (m, 2H), 3.58-3.68 (m, 1H), 3.73 (s, 3H), 4.64 (br. s., 2H), 5.22 (d, 1H), 6.32 (d, 1H), 7.11 (t, 1H).

UPLC-MS (ESI+): [M+H]$^+$=323; R$_t$=1.51 min.

Intermediate 1-4

(±) methyl 5-amino-2-methoxy-4-{[(cis)-3,3,5-trimethylcyclohexyl]amino}benzoate

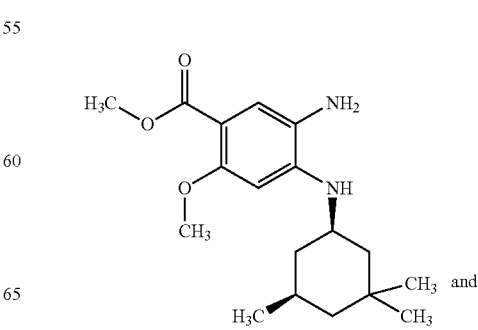

and

-continued

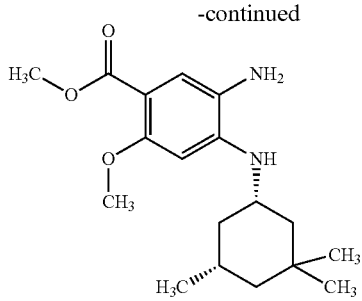

Step 1: (±) methyl 2-fluoro-5-nitro-4-{[(cis)-3,3,5-trimethylcyclohexyl]amino}benzoate and (±) methyl 4-fluoro-5-nitro-2-{[(cis)-3,3,5-trimethylcyclohexyl]amino}benzoate A solution of methyl 2,4-difluoro-5-nitrobenzoate (CAS No. [125568-71-0]; 15.7 g, 72.3 mmol) in acetonitrile (360 mL) was treated with triethylamine (1.30 eq., 13.1 mL, 94.0 mmol) and 3,3,5-trimethylcyclohexanamine (mixture of stereoisomers, commercially available; 1.40 eq., 14.3 g, 101 mmol) and stirred at room temperature overnight. The reaction mixture was diluted with water (300 mL) and the pH of the mixture was adjusted to pH 3 by addition of aqueous hydrochloric acid (2M). The reaction mixture was extracted with ethyl acetate and the combined organic layers were washed with water, brine, dried with sodium sulfate and concentrated in vacuo to give a mixture of (±) methyl 2-fluoro-5-nitro-4-{[(cis)-3,3,5-trimethylcyclohexyl]amino}benzoate and (±) methyl 4-fluoro-5-nitro-2-{[(cis)-3,3,5-trimethylcyclohexyl]amino}benzoate (ca 78:22, 33.5 g, quant.). The material (which contained small amounts of the corresponding trans-products) was used in the next step without further purification.

UPLC-MS (ESI+): [M+H]$^+$=339; $R_t$=1.72/1.76 min.

Step 2: (±) methyl 2-methoxy-5-nitro-4-{[(cis)-3,3,5-trimethylcyclohexyl]amino}benzoate An ice-cooled mixture of (±) methyl 2-fluoro-5-nitro-4-{[(cis)-3,3,5-trimethylcyclohexyl]amino}benzoate and (±) methyl 4-fluoro-5-nitro-2-{[(cis)-3,3,5-trimethylcyclohexyl]amino}benzoate (ca 78:22; 7.00 g, 16.5 mmol) from step 1 in methanol (15 mL) was slowly treated with a solution of sodium methanolate in methanol (CAS No. [124-41-4]; 10 eq., 38 mL of a 30wt % solution) and stirred at 0° C. for 1 hour. The suspension was taken up with ethyl acetate and washed with water. The phases were separated, the organic layer dried with sodium sulfate and concentrated in vacuo. The obtained material was purified by flash chromatography (SiO$_2$-hexane/ethyl acetate) to give the title compound (2.9 g, 50%) as racemic cis diastereomer.

UPLC-MS (ESI+): [M+H]$^+$=351; $R_t$=1.57 min.

Step 3: (±) methyl 5-amino-2-methoxy-4-{[(cis)-3,3,5-trimethylcyclohexyl]amino}benzoate In analogy to step 2 of intermediate 1-1: (±) Methyl 2-methoxy-5-nitro-4-{[(cis)-3,3,5-trimethylcyclohexyl]amino}benzoate (2.07 g, 5.26 mmol) from step 2 was hydrogenated with palladium on carbon (10 wt %; 0.250 eq., 140 mg, 1.31 mmol) and hydrogen gas in ethyl acetate (80 mL) at rt overnight to give the title compound (1.9 g, quant.) which was used in the next step without further purification.

$^1$H-NMR (400 MHz, DMSO-d$_6$): δ [ppm]=0.73-0.82 (m, 2H), 0.90 (d, 3H), 0.93-0.99 (m, 4H), 1.01 (s, 3H), 1.36-1.39 (m, 1H), 1.71-1.82 (m, 2H), 1.95-1.99 (m, 1H), 3.47-3.58 (m, 1H), 3.65 (s, 3H), 3.69 (s, 3H), 4.29 (br. s., 2H), 4.91 (d, 1H), 6.10 (s, 1H), 7.03 (s, 1H).

UPLC-MS (ESI+): [M+H]$^+$=321; $R_t$=1.26 min (Method E).

Intermediate 1-5

(±) methyl 3-(5-amino-2-methoxy-4-{[(cis)-3,3,5-trimethylcyclohexyl]amino}phenyl)propanoate

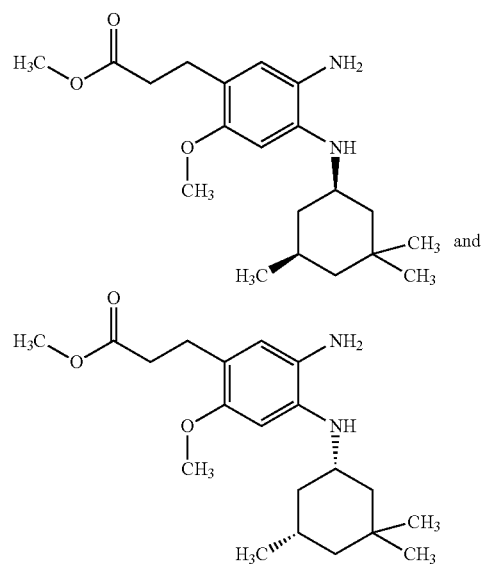

Step 1: 1-bromo-4-fluoro-2-methoxy-5-nitrobenzene

A mixture of 1-bromo-4-fluoro-2-methoxybenzene (CAS No. [450-88-4]; 10.0 g, 48.8 mmol) in concentrated sulfuric acid (50 mL) was cooled to 0° C. and treated dropwise with a freshly prepared mixture of fuming nitric acid (1.05 eq., 2.1 mL, 51 mmol) and concentrated sulfuric acid (1.85 eq., 4.8 mL, 90 mmol). The reaction mixture was stirred at 0° C. for 30 minutes and poured in small portions on ice water. The formed precipitate was filtered off, washed with cold water and kept. The filtrate was extracted with ethyl acetate and the organic layer combined with the isolated precipitation. The organic layer was dried with sodium sulfate and concentrated in vacuo. The obtained material was purified by flash chromatography (SiO$_2$-hexane/ethyl acetate) to give the title compound (5.88 g, 44%).

$^1$H-NMR (400 MHz, DMSO-d$_6$): δ [ppm]=4.00 (s, 3H), 7.44 (d, 1H), 8.40 (d, 1H). UPLC-UPLC-MS (ESI−): [M−H]$^-$=248/250; $R_t$=1.17 min (Br isotope pattern; Method E).

Step 2: (±) 4-bromo-5-methoxy-2-nitro-N-[(cis)-3,3,5-trimethylcyclohexyl]aniline A solution of 1-bromo-4-fluoro-2-methoxy-5-nitrobenzene (2.90 g, 11.6 mmol) from step 1 in THF (87 mL) was treated with potassium carbonate (1.10 eq., 1.76 g, 12.8 mmol) and 3,3,5-trimethylcyclohexanamine (mixture of stereoisomers, commercially available; 1.00 eq., 1.64 g, 11.6 mmol) and stirred at 70° C. overnight. The reaction mixture was filtered, the filtrate partitioned between water and ethyl acetate and extracted with ethyl acetate. The combined organic layers were washed with water, brine, dried with sodium sulfate and concentrated in vacuo to give the title compound (4.39 g, 97%) as a racemic mixture of cis diastereomer (ca 92-94%) and trans diastereomer (ca 6-8%) which was not further purified.

$^1$H-NMR (400 MHz, DMSO-d$_6$, cis isomer): δ [ppm] =0.81-0.94 (m, 8H), 1.04 (s, 3H), 1.08 (t, 1H), 1.35-1.38 (m, 1H), 1.76-1.79 (m, 2H), 2.02-2.05 (m, 1H), 3.83-3.93 (m, 1H), 3.98 (s, 3H), 6.44 (s, 1H), 8.14 (br. d., 1H), 8.22 (s, 1H).

UPLC-MS (ESI+): [M+H]$^+$=371/373; R$_t$=1.72 min (Br isotope pattern; Method E).

Step 3: (±) methyl (2E)-3-(2-methoxy-5-nitro-4-{[(cis)-3,3,5-trimethylcyclohexyl]amino}phenyl)prop-2-enoate To a solution of (±) 4-bromo-5-methoxy-2-nitro-N-[(cis)-3,3,5-trimethylcyclohexyl]aniline (6.79 g, 17.4 mmol) from step 2 in DMF (129 mL) were added methyl prop-2-enoate (CAS No. [96-33-3]; 3.00 eq., 4.69 mL, 52.1 mmol) and triethylamine (2.00 eq., 4.84 mL, 34.7 mmol). The mixture was purged with argon several times and stirred at rt for 10 minutes. Tetrakis(triphenylphosphine)palladium (0.150 eq., 3.01 g, 2.61 mmol) was added, the mixture purged with argon again and heated to 110° C. overnight. The reaction mixture was cooled to rt and diluted with water. It was extracted with ethyl acetate (3 times) and the combined organic layers were washed with brine, dried with sodium sulfate and concentrated in vacuo. The obtained material was purified by flash chromatography (SiO$_2$-hexane/ethyl acetate) to give the title compound (3.9 g, 55%) as racemic cis diastereomer.

$^1$H-NMR (300 MHz, DMSO-d$_6$): δ [ppm]=0.80-0.94 (m, 8H), 1.04 (s, 3H), 1.11 (t, 1H), 1.35-1.39 (m, 1H), 1.76-1.80 (m, 2H), 2.01-2.05 (m, 1H), 3.69 (s, 3H), 3.85-3.96 (m, 1H), 4.00 (s, 3H), 6.39 (s, 1H), 6.53 (d, 1H), 7.66 (d, 1H), 8.27 (br. d., 1H), 8.40 (s, 1H).

UPLC-MS (ESI+): [M+H]$^+$=377; R$_t$=1.68 min (Method E).

Step 4: (±) methyl 3-(5-amino-2-methoxy-4-{[(cis)-3,3,5-trimethylcyclohexyl]amino}phenyl)propanoate A solution of (±) methyl (2E)-3-(2-methoxy-5-nitro-4-{[(cis)-3,3,5-trimethylcyclohexyl]amino}phenyl)prop-2-enoate (2.70 g, 7.17 mmol) from step 3 in ethyl acetate (190 mL) was treated with palladium on carbon (10 wt %; 1.50 eq., 1.15 g, 10.8 mmol) and stirred under a hydrogen atmosphere at rt overnight. Due to incomplete conversion another amount of palladium on carbon (10 wt %; 0.50 eq., 382 mg, 3.59 mmol) was added and stirring under a hydrogen atmosphere at rt continued for one day. The reaction mixture was filtrated over Celite, washed with ethyl acetate and the filtrate concentrated in vacuo to give the title compound (2.34 g, 84%) as racemic cis diastereomer which was not further purified.

$^1$H-NMR (400 MHz, DMSO-d$_6$): δ [ppm]=0.66-0.74 (m, 1H), 0.77 (t, 1H), 0.85-0.91 (m, 7H), 0.99 (s, 3H), 1.34-1.37 (m, 1H), 1.70-1.73 (m, 1H), 1.94-1.97 (m, 1H), 2.40-2.44 (m, 2H), 2.58-2.62 (m, 2H), 3.33-3.41 (m, 1H), 3.57 (s, 3H), 3.65 (s, 3H), 3.94 (br. d., 1H), 4.00 (br. s., 2H), 6.13 (s, 1H), 6.33 (s, 1H).

UPLC-MS (ESI+): [M+H]$^+$=349; R$_t$=1.49 min (Method F).

Intermediate 1-6

(±) methyl 3-(5-amino-2-methyl-4-{[(cis)-3,3,5-trimethylcyclohexyl]amino}phenyl)propanoate

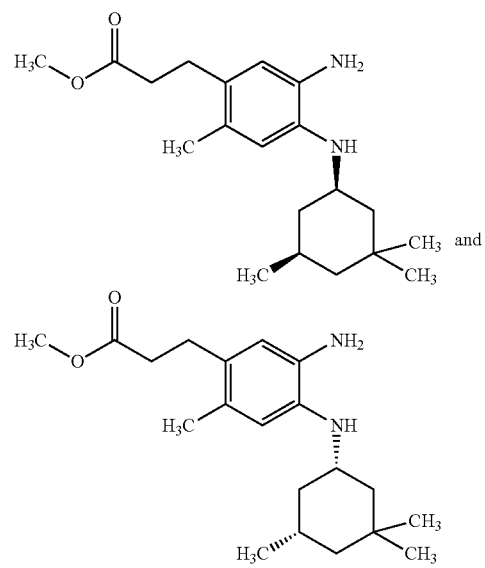

Step 1: (±) 4-bromo-5-methyl-2-nitro-N-[(cis)-3,3,5-trimethylcyclohexyl]aniline

In analogy to step 1 of intermediate 1-1: 1-Bromo-4-fluoro-2-methyl-5-nitrobenzene (CAS No. [170098-98-3]; 1.00 eq., 3.60 g, 15.4 mmol) was reacted with potassium carbonate (1.10 eq., 2.34 g, 16.9 mmol) and 3,3,5-trimethylcyclohexanamine (mixture of stereoisomers, commercially available; 1.00 eq., 2.17 g, 15.4 mmol) in THF (110 mL) at rt for 7 days and at 40° C. for 3 hours to give after purification by flash chromatography (SiO$_2$-hexane/ethyl acetate) the title compound (5.1 g, 84%) as a racemic mixture of cis diastereomer (ca 90%) and trans diastereomer (ca 7%).

$^1$H-NMR (300MHz, DMSO-d$_6$, cis isomer): δ [ppm] =0.72-0.89 (m, 5H), 0.94 (s, 3H), 1.01 (s, 3H), 1.13 (t, 1H), 1.33-1.37 (m, 1H), 1.65-1.87 (m, 2H), 1.98-2.02 (m, 1H), 2.37 (s, 3H), 3.75-3.88 (m, 1H), 7.16 (s, 1H), 7.82 (br. d., 1H), 8.16 (s, 1H).

UPLC-MS (ESI+): [M+H]$^+$=355/357; R$_t$=1.84 min (Br isotope pattern; Method E).

Step 2: (±) methyl (2E)-3-(2-methyl-5-nitro-4-{[(cis)-3,3,5-trimethylcyclohexyl]amino}phenyl)prop-2-enoate In analogy to step 3 of intermediate 1-5: (±) 4-Bromo-5-methyl-2-nitro-N-[(cis)-3,3,5-trimethylcyclohexyl]aniline (2.41 g, 6.78 mmol) from step 1 was reacted with methyl prop-2-enoate (CAS No. [96-33-3]; 3.00 eq., 1.83 mL, 20.4 mmol), triethylamine (2.00 eq., 1.89 mL, 13.6 mmol) and tetrakis(triphenylphosphine)palladium (0.150 eq., 1.18 g, 1.02 mmol) in DMF (48 mL) at 110° C. overnight to give after purification by flash chromatography (SiO$_2$-hexane/ethyl acetate) the title compound (1.81 g, 73%) as racemic cis diastereomer.

$^1$H-NMR (300 MHz, DMSO-d$_6$): δ [ppm]=0.75-0.94 (m, 8H), 1.02 (s, 3H), 1.15 (t, 1H), 1.34-1.38 (m, 1H), 1.67-1.86 (m, 2H), 1.99-2.02 (m, 1H), 2.42 (s, 3H), 3.71 (s, 3H), 3.81-3.91 (m, 1H), 6.43 (d, 1H), 7.02 (s, 1H), 7.69 (d, 1H), 7.98 (br. d., 1H), 8.38 (s, 1H).

UPLC-MS (ESI+): [M+H]$^+$=361; R$_t$=1.72 min (Method E).

Step 3: (±) methyl 3-(5-amino-2-methyl-4-{[(cis)-3,3,5-trimethylcyclohexyl]amino}phenyl)propanoate In analogy to step 4 of intermediate 1-5: A solution of (±) methyl (2E)-3-(2-methyl-5-nitro-4-{[(cis)-3,3,5-trimethylcyclohexyl]amino}phenyl)prop-2-enoate (1.81 g, 5.02 mmol) from step 2 in a mixture of ethanol (100 mL) and ethyl acetate (30 mL) was treated with palladium on carbon (10 wt %; 1.50 eq., 801 mg, 7.53 mmol) and stirred under a hydrogen atmosphere at rt overnight. The reaction mixture was filtrated over Celite, washed with ethyl acetate and the filtrate concentrated in vacuo to give the title compound (1.76 g, 79%) as racemic cis diastereomer which was not further purified.

UPLC-MS (ESI+): [M+H]$^+$=333; R$_t$=1.52 min (Method F).

Intermediate 1-7

(±) methyl 5-amino-2-(propan-2-yloxy)-4-{[(trans)-3,3,5-trimethylcyclohexyl]amino}benzoate and (±) methyl 5-amino-2-(propan-2-yloxy)-4-{[(cis)-3,3,5-trimethylcyclohexyl]amino}benzoate

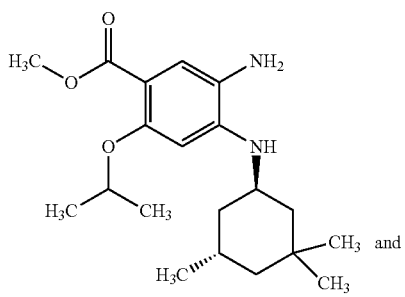

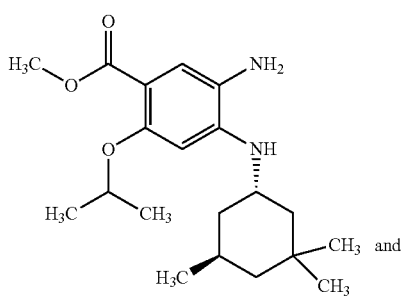

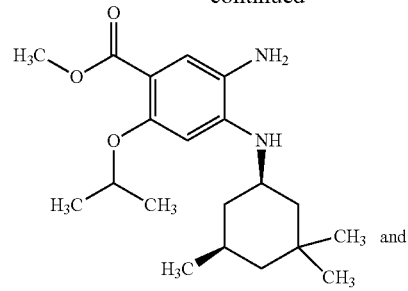

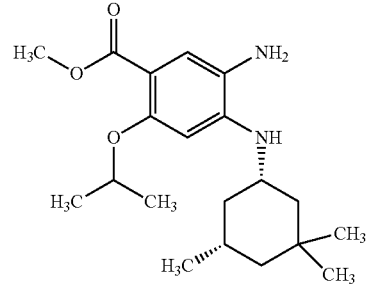

Step 1: (±) methyl 5-nitro-2-(propan-2-yloxy)-4-{[(trans)-3,3,5-trimethylcyclohexyl]amino}benzoate and (±) methyl 5-nitro-2-(propan-2-yloxy)-4-{[(cis)-3,3,5-trimethylcyclohexyl]amino}benzoate Sodium propan-2-olate (2.11 g, 25.7 mmol) in propan-2-ol (25 mL) was stirred at rt for 15 min and then cooled to −10° C. To this mixture was dropwise added a solution of (±) methyl 2-fluoro-5-nitro-4-{[(cis)-3,3,5-trimethylcyclohexyl]amino}benzoate and (±) methyl 4-fluoro-5-nitro-2-{[(cis)-3,3,5-trimethylcyclohexyl]amino}benzoate (ca 78:22; 8.70 g, 25.7 mmol) from step 1 of intermediate 1-4 (containing small amounts of the corresponding trans-products) in propan-2-ol (25 mL) and stirring at −10° C. continued for 30 min. The reaction mixtures was poured into water and extracted twice with ethyl acetate. The combined organic layers were dried with sodium sulfate and concentrated in vacuo. The obtained material was purified by flash chromatography (SiO$_2$-hexane/ethyl acetate) to give the title compound (1.22 g, 11%) as a racemic mixture of cis and trans (ca 87:13) diastereomer.

$^1$H-NMR (400 MHz, DMSO-d$_6$, cis isomer): δ [ppm] =0.78-0.94 (m, 8H), 1.03 (s, 3H), 1.12 (t, 1H), 1.34-1.39 (m, 7H), 1.73-1.84 (m, 2H), 1.98-2.01 (m, 1H), 3.75 (s, 3H), 3.84-3.93 (m, 1H), 4.88 (sept, 1H), 6.35 (s, 1H) [trans isomer 6.31 (s, 1H)], 8.17 (d, 1H) [trans isomer 8.30 (d, 1H)], 8.65 (s, 1H).

UPLC-MS (ESI+): [M+H]$^+$=379; R$_t$=1.64/1.70 min (Method E).

Step 2: (±) methyl 5-amino-2-(propan-2-yloxy)-4-{[(trans)-3,3,5-trimethylcyclohexyl]amino}benzoate and (±) methyl 5-amino-2-(propan-2-yloxy)-4-{[(cis)-3,3,5-trimethylcyclohexyl]amino}benzoate In analogy to step 4 of intermediate 1-5: A solution of (±) methyl 5-nitro-2-(propan-2-yloxy)-4-{[(trans)-3,3,5-trimethylcyclohexyl]amino}benzoate and (±) methyl 5-nitro-2-(propan-2-yloxy)-4-{[(cis)-3,3,5-trimethylcyclohexyl]amino}benzoate (1.22 g, 2.80 mmol) from step 1 in ethyl acetate (56 mL) was treated with palladium on carbon (10wt %; 1.50 eq., 448 mg, 4.21 mmol) and stirred under a hydrogen atmosphere at rt overnight. The reaction mixture was filtrated over Celite, washed with ethyl acetate and the filtrate concentrated in vacuo to give the title compound (1.08 g, 97%) as a racemic mixture of cis and trans (ca 88:12) diastereomer which was not further purified.

$^1$H-NMR (400 MHz, DMSO-$d_6$, cis isomer): δ [ppm]=0.73-0.82 (m, 2H), 0.88-1.01 (m, 10H), 1.21 (d, 6H), 1.35-1.39 (m, 1H), 1.69-1.79 (m, 2H), 1.93-1.97 (m, 1H), 3.42-3.50 (m, 1H), 3.66 (s, 3H), 4.26 (sept, 1H), 4.36 (br. s., 2H), 4.85 (d, 1H), 6.06 (s, 1H) [trans isomer 6.21 (s, 1H)], 7.01 (s, 1H) [trans isomer 7.11 (s, 1H)].

UPLC-MS (ESI+): [M+H]+=349; $R_t$=1.52/1.54 min (Method F).

Intermediate 1-8

(±) methyl 5-amino-2-(2,2,2-trifluoroethoxy)-4-{[(cis)-3,3,5-trimethylcyclohexyl]amino}benzoate

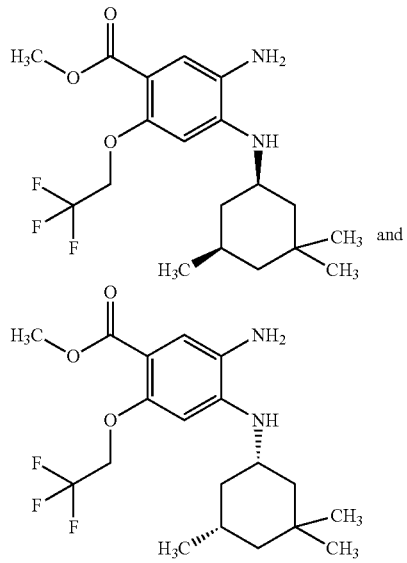

Step 1: (±) methyl 5-nitro-2-(2,2,2-trifluoroethoxy)-4-{[(cis)-3,3,5-trimethylcyclohexyl]amino}benzoate A solution of 2,2,2-trifluoroethanol (355 mg, 3.55 mmol) in THF (8 mL) was treated with potassium 2-methylpropan-2-olate, stirred at rt for 10 min and then cooled in an ice-bath. To this mixture was dropwise added a solution of (±) methyl 2-fluoro-5-nitro-4-{[(cis)-3,3,5-trimethylcyclohexyl]amino}benzoate and (±) methyl 4-fluoro-5-nitro-2-{[(cis)-3,3,5-trimethylcyclohexyl]amino}benzoate (ca 78:22; 1.00 g, 2.96 mmol) from step 1 of intermediate 1-4 (containing small amounts of the corresponding trans-products) in THF (8 mL) and stirring under ice-bath cooling continued for 1 h. The reaction mixtures was poured into water and extracted twice with ethyl acetate. The combined organic layers were dried with sodium sulfate and concentrated in vacuo. The obtained material was purified by flash chromatography (SiO$_2$-hexane/ethyl acetate) to give the title compound (515 mg, 41%) as racemic cis diastereomer.

$^1$H-NMR (400 MHz, DMSO-$d_6$): δ [ppm]=0.81-0.95 (m, 5H), 0.95 (s, 3H), 1.04 (s, 3H), 1.15 (t, 1H), 1.35-1.39 (m, 1H), 1.75-1.82 (m, 2H), 2.03-2.06 (m, 1H), 3.76 (s, 3H), 3.87-3.96 (m, 1H), 5.00-5.07 (m, 2H), 6.46 (s, 1H), 8.23 (d, 1H), 8.61 (s, 1H).

UPLC-MS (ESI+): [M+H]+=419; $R_t$=1.65 min (Method E).

Step 2: (±) methyl 5-amino-2-(2,2,2-trifluoroethoxy)-4-{[(cis)-3,3,5-trimethylcyclohexyl]amino}benzoate In analogy to step 4 of intermediate 1-5: A solution of (±) methyl 5-nitro-2-(2,2,2-trifluoroethoxy)-4-{[(cis)-3,3,5-trimethylcyclohexyl]amino}benzoate (510 mg, 1.22 mmol) from step 1 in ethyl acetate (36 mL) was treated with palladium on carbon (10 wt %; 1.50 eq., 195 mg, 1.83 mmol) and stirred under a hydrogen atmosphere at rt overnight. The reaction mixture was filtrated over Celite, washed with ethanol and the filtrate concentrated in vacuo to give the title compound (440 mg, 60%) as racemic cis diastereomer which was not further purified.

UPLC-MS (ESI+): [M+H]+=389; $R_t$=1.49 min (Method E).

Intermediate 1-9

(±) 3-amino-4-{[(trans)-3,3,5-trimethylcyclohexyl]amino}benzonitrile and (±) 3-amino-4-{[(cis)-3,3,5-trimethylcyclohexyl]amino}benzonitrile

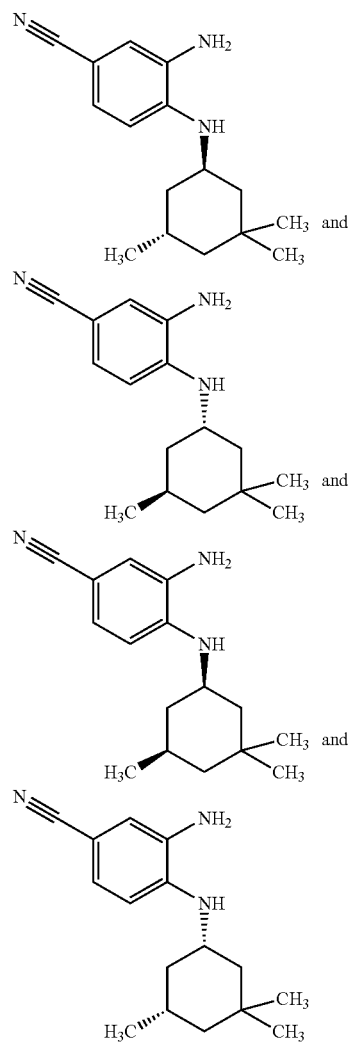

Step 1: (±) 3-nitro-4-{[(trans)-3,3,5-trimethylcyclohexyl]amino}benzonitrile and (±) 3-nitro-4-{[(cis)-3,3,5-trimethylcyclohexyl]amino}benzonitrile In analogy to step 1 of intermediate 1-1: 4-Fluoro-3-nitrobenzonitrile (1.00 eq., 5.00 g, 30.1 mmol) was reacted with potassium carbonate (2.00 eq., 8.32 g, 60.2 mmol) and 3,3,5-trimethylcyclohexanamine (mixture of stereoisomers, commercially available; 1.00 eq., 4.25 g, 30.1 mmol) in THF (195 mL) at 50° C. overnight to give the title compound (9.83 g, quant.) as a racemic mixture of cis diastereomer (ca 93%) and trans diastereomer (ca 7%).

$^1$H-NMR (400 MHz, DMSO-$d_6$, cis isomer): δ [ppm] =0.80-0.94 (m, 8H), 1.01 (s, 3H), 1.20 (t, 1H), 1.34-1.37 (m, 1H), 1.66-1.69 (m, 1H), 1.76-1.83 (m, 1H), 1.95-1.99 (m, 1H), 3.84-3.92 (m, 1H), 7.27 (d, 1H) [trans isomer 7.20 (d, 1H)], 7.83 (dd, 1H), 8.15 (br. d., 1H), 8.51 (d, 1H) [trans isomer 8.54 (d, 1H)].

UPLC-MS (ESI+): [M+H]$^+$=288; $R_t$=1.59 min (Method E).

Step 2: (±) 3-amino-4-{[(trans)-3,3,5-trimethylcyclohexyl]amino}benzonitrile and (±) 3-amino-4-{[(cis)-3,3,5-trimethylcyclohexyl]amino}benzonitrile In analogy to step 4 of intermediate 1-5: A solution of (±) 3-nitro-4-{[(trans)-3,3,5-trimethylcyclohexyl]amino}benzonitrile and (±) 3-nitro-4-{[(cis)-3,3,5-trimethylcyclohexyl]amino}benzonitrile (9.83 g, 32.5 mmol) from step 1 in ethyl acetate (200 mL) was treated with palladium on carbon (10 wt %; 0.20 eq., 692 mg, 6.50 mmol) and stirred under a hydrogen atmosphere at rt for 18 h. The reaction mixture was filtrated over Celite, washed with ethyl acetate and the filtrate concentrated in vacuo to give the title compound (7.78 g, 79%) as a racemic mixture of cis and trans (ca 90:10) diastereomer which was not further purified.

$^1$H-NMR (400 MHz, DMSO-$d_6$, cis isomer): δ [ppm] =0.66-0.81 (m, 2H), 0.87-1.03 (m, 10H), 1.35-1.37 (m, 1H), 1.60-1.77 (m, 2H), 1.95-1.98 (m, 1H), 3.46-3.54 (m, 1H), 4.96-5.00 (m, 3H), 6.49 (d, 1H) [trans isomer 6.44 (d, 1H)], 6.75 (d, 1H), 6.90 (dd, 1H).

UPLC-MS (ESI+): [M+H]$^+$=258; $R_t$=1.43/1.45 min (Method F).

Intermediate 1-10 methyl 3-{3-amino-2-fluoro-4-[(3,3,5-tetramethylcyclohexyl)amino]phenyl}propanoate

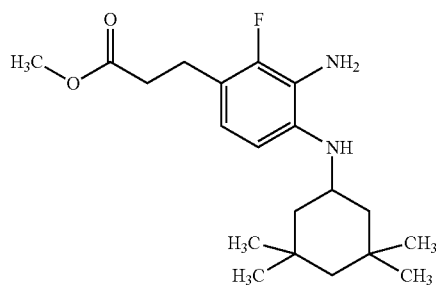

Step 1: methyl (2E)-3-{2-fluoro-3-nitro-4-[(3,3,5-tetramethylcyclohexyl)amino]phenyl}acrylate 4-Bromo-3-fluoro-2-nitro-N-(3,3,5-tetramethylcyclohexyl)aniline (prepared in step 1 of intermediate 1-3; 2.20 g, 5.89 mmol) was dissolved in N,N-dimethylformamide (73 mL) followed by addition of methyl acrylate (1.59 mL, 17.68 mmol) and triethylamine (1.64 mL, 11.79 mmol). The mixture was degassed with argon for 15 min then tetrakis(triphenylphosphine)palladium (681 mg, 0.59 mmol) was added and the reaction was heated at 120° C. for 18 h. The reaction was cooled and brine (50 mL) and ethyl acetate (50 mL) were added. The layers were separated and the aqueous layer was extracted with ethyl acetate (3×50 mL). The combined organic layers were dried over solid sodium sulfate and concentrated under vacuum. The crude material was purified by flash chromatography (SiO$_2$-heptane/ethyl acetate) to give the title compound (0.88 mg, 39%) as an orange solid.

$^1$H-NMR (300 MHz, CDCl$_3$): δ [ppm]=0.96 (s, 6H), 1.09 (s, 6H), 1.05-1.31 (m, 2H), 1.81 (d, 2H), 3.73 (m, 1H), 3.79 (s, 3H), 6.31 (d, 1H), 6.63 (d, 1H), 7.52 (dd, 1H), 7.73 (d, 1H).

UPLC-MS (ESI−): [M−H]$^-$=377; $R_t$=1.12 min (Method G).

Step 2: methyl 3-{3-amino-2-fluoro-4-[(3,3,5,5-tetramethylcyclohexyl)amino]phenyl}propanoate To a solution of methyl (2E)-3-{2-fluoro-3-nitro-4-[(3,3,5,5-tetramethylcyclohexyl)amino]phenyl}prop-2-enoate (880 mg, 2.32 mmol) from step 1 in tetrahydrofuran (44 mL) was added 5% palladium on carbon (494 mg, 0.23 mmol) and the reaction was stirred under a hydrogen atmosphere (1 atm) for 18 h. The reaction was filtered through celite using ethyl acetate and the filtrate concentrated. The residue was purified by flash chromatography (SiO$_2$-heptane/ethyl acetate) to give the title compound (858 mg, quantitative) as a brown oil.

$^1$H-NMR (300 MHz, CDCl$_3$): δ [ppm]=0.92 (s, 6H), 1.10 (s, 6H), 0.87-1.26 (m, 4H), 1.85 (d, 2H), 2.58 (t, 2H), 2.87 (t, 2H), 3.20 (br. s., 3H), 3.49-3.60 (m, 1H), 3.67 (s, 3H), 6.36 (d, 1H), 6.58 (dd, 1H).

UPLC-MS (ESI+): [M+H]$^+$=351; $R_t$=1.05 min (Method G).

EXAMPLES

Example 2-1

(±) methyl 2-[4-(trifluoromethoxy)phenyl]-1-[(cis)-3,3,5-trimethylcyclohexyl]-1H-benzimidazole-5-carboxylate

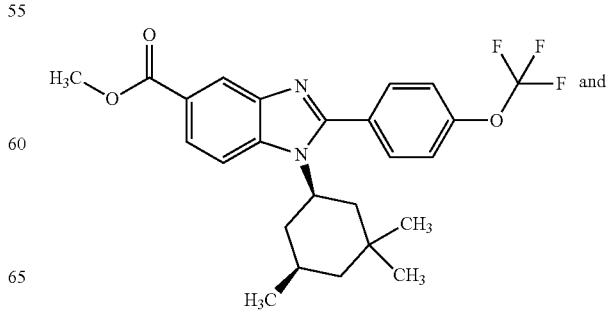

and

-continued

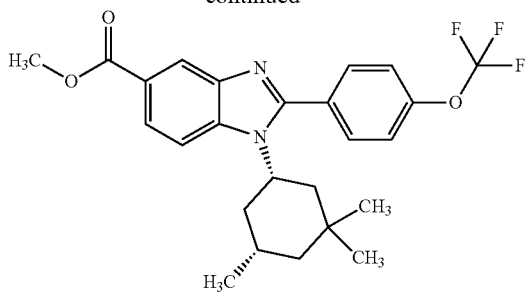

A solution of sodium sulfite (2.25 eq., 150 mg, 1.19 mmol) in water (1 mL) was stirred at rt for 30 min upon which a solution of 4-(trifluoromethoxy)benzaldehyde (CAS No. [659-28-9]; 1.00 eq, 101 mg, 0.530 mmol) in THF (1 mL) was added dropwise at rt and stirring at rt continued for 1 h. A solution of (±) methyl 3-amino-4-{[(cis)-3,3,5-trimethylcyclohexyl]amino}benzoate (intermediate 1-1; 1.30 eq., 200 mg, 0.689 mmol) in THF (1 mL) was added dropwise, the reaction mixture heated to 65° C. and stirring at this temperature continued overnight. Another amount of 4-(trifluoromethoxy)benzaldehyde (0.80 eq, 81 mg, 0.42 mmol) was added and the mixture stirred at 65° C. for another 3 h. The reaction mixture was diluted with water and extracted with ethyl acetate. The organic layer was washed with aqueous sat. sodium hydrocarbonate solution and brine, dried with sodium sulfate and concentrated in vacuo to give the title compound (333 mg, quant.) which was not further purified.

$^1$H-NMR (400 MHz, DMSO-d$_6$): δ [ppm]=0.84 (s, 3H), 0.90 (d, 3H), 0.99 (s, 3H), 1.09 (t, 1H), 1.32-1.35 (m, 1H), 1.65-1.72 (m, 2H), 1.82-1.90 (m, 2H), 2.10 (t, 1H), 3.89 (s, 3H), 4.44-4.52 (m, 1H), 7.59-7.61 (m, 2H), 7.81-7.85 (m, 2H), 7.88 (dd, 1H), 8.00 (d, 1H), 8.28 (d, 1H).

UPLC-MS (ESI+): [M+H]$^+$=461; R$_t$=1.66 min (Method E).

The enantiomers of the racemic material of example 2-1 were separated by chiral preparative HPLC (System: Agilent: Prep 1200, 2× Prep Pump, DLA, MWD, Gilson: Liquid Handler 215; Column: Chiralpak IC 5 µm 250×30 mm; Solvent: hexane/ethanol 70:30 (v/v); Flow: 50 ml/min; Temperature: rt; Solution: 261 mg/5.5 mL DCM/MeOH; Injection: 10×0.55 mL; Detection: UV 254 nm) and analytically characterized by chiral HPLC (System: Waters: Alliance 2695, DAD 996, ESA: Corona; Column: Chiralpak IC 5 µm 150×4.6 mm; Solvent: hexane/ethanol 70:30 (v/v); Flow: 1.0 mL/min; Temperature: 25° C.; Solution: 1.0 mg/mL EtOH/MeOH 1:1; Injection: 5.0 µL; Detection: DAD 254 nm):

Example 2-1-1 methyl 2-[4-(trifluoromethoxy)phenyl]-1-[(cis)-3,3,5-trimethylcyclohexyl]-1H-benzimidazole-5-carboxylate, Enantiomer A

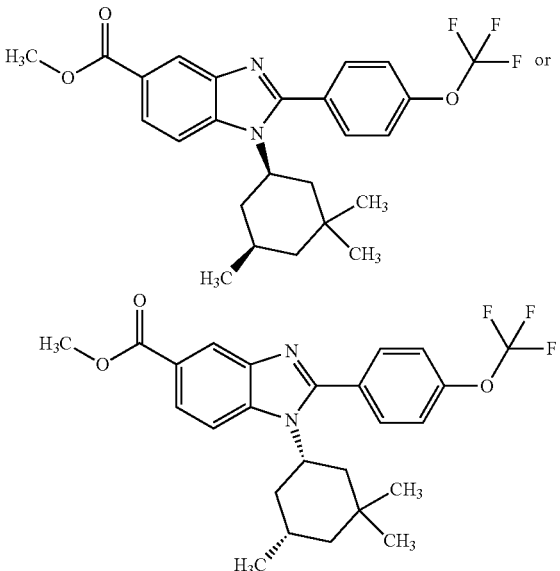

R$_t$ = 4.56 min

Example 2-1-2 methyl 2-[4-(trifluoromethoxy)phenyl]-1-[(cis)-3,3,5-trimethylcyclohexyl]-1H-benzimidazole-5-carboxylate, Enantiomer B

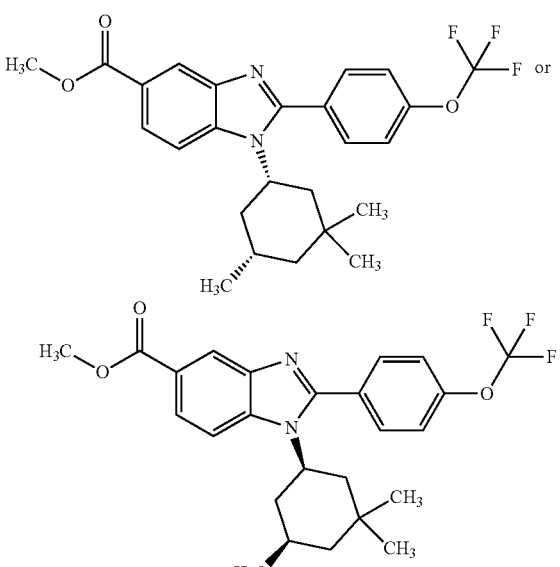

R$_t$ = 5.08 min

Example 2-2

(±) 2-[4-(trifluoromethoxy)phenyl]-1-[(cis)-3,3,5-trimethylcyclohexyl]-1H-benzimidazole-5-carboxylic Acid

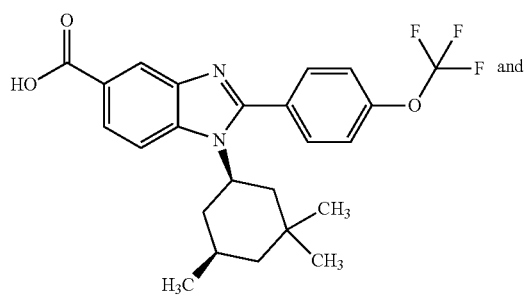

and

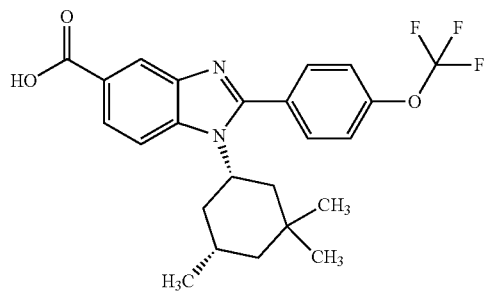

A solution of (±) methyl 2-[4-(trifluoromethoxy)phenyl]-1-[(cis)-3,3,5-trimethylcyclohexyl]-1H-benzimidazole-5-carboxylate (example 2-1; 32.5 mg, 0.0706 mmol) in a mixture of THF/water (1:1, 2 mL) was treated with lithium hydroxide (5.0 eq., 8.5 mg, 0.35 mmol) and stirred at 70° C. for 23 h. The reaction mixture was acidified with 2 M aqueous hydrochloric acid (pH 4-5) and diluted with ethyl acetate. The layers were separated and the aqouess layer extracted twice with ethyl acetate. The combined organic layers were washed with water and brine, dried with sodium sulfate and concentrated in vacuo. The obtained crude product (13 mg, 40%) was not further purified.

$^{1}$H-NMR (300 MHz, DMSO-$d_6$): δ [ppm]=0.84 (s, 3H), 0.89 (d, 3H), 0.99 (s, 3H), 1.09 (t, 1H), 1.32-1.36 (m, 1H), 1.56-1.73 (m, 2H), 1.83-1.91 (m, 2H), 2.11 (t, 1H), 4.42-4.53 (m, 1H), 7.58-7.61 (m, 2H), 7.81-7.84 (m, 2H), 7.87 (dd, 1H), 7.97 (d, 1H), 8.25 (d, 1H), 12.80 (br. s., 1H).

UPLC-MS (ESI+): [M+H]$^{+}$=447; R$_t$=1.53 min (Method E).

Example 2-2-1

2-[4-(trifluoromethoxy)phenyl]-1-[(cis)-3,3,5-trimethylcyclohexyl]-1H-benzimidazole-5-carboxylic Acid, Enantiomer A

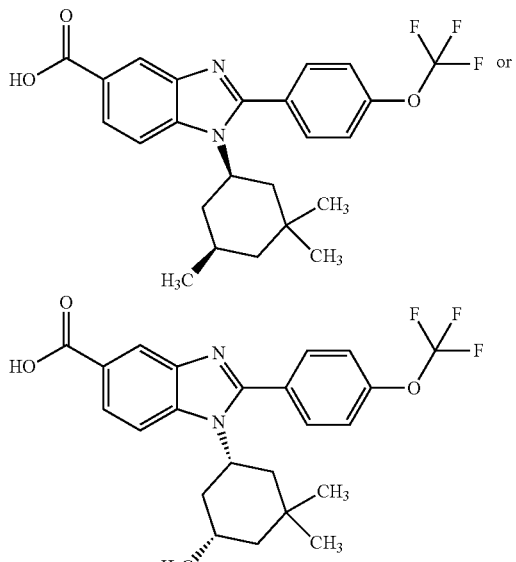

or

In analogy to example 2-2: Methyl 2-[4-(trifluoromethoxy)phenyl]-1-[(cis)-3,3,5-trimethylcyclohexyl]-1H-benzimidazole-5-carboxylate, enantiomer A (example 2-1-1; 108 mg, 0.235 mmol) was reacted with lithium hydroxide (5.0 eq., 28 mg, 1.2 mmol) in a mixture of THF/water (1:1, 4 mL) at 70° C. overnight to give the crude title compound (87.5 mg, 79%) which was not further purified.

$^{1}$H-NMR (400 MHz, DMSO-$d_6$): δ [ppm]=0.84 (s, 3H), 0.90 (d, 3H), 0.99 (s, 3H), 1.09 (t, 1H), 1.32-1.35 (m, 1H), 1.60-1.72 (m, 2H), 1.85-1.93 (m, 2H), 2.10 (t, 1H), 4.44-4.52 (m, 1H), 7.58-7.60 (m, 2H), 7.81-7.84 (m, 2H), 7.87 (dd, 1H), 7.97 (d, 1H), 8.26 (d, 1H), 12.77 (s, 1H).

UPLC-MS (ESI+): [M+H]$^{+}$=447; R$_t$=1.54 min (Method E).

Example 2-2-2

2-[4-(trifluoromethoxy)phenyl]-1-[(cis)-3,3,5-trimethylcyclohexyl]-1H-benzimidazole-5-carboxylic Acid, Enantiomer B

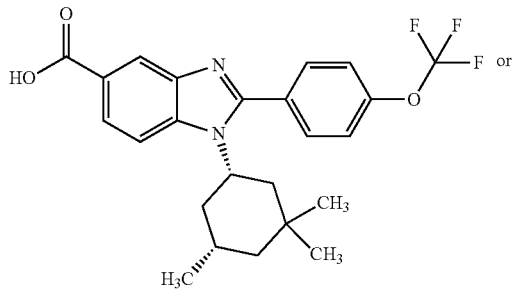

or

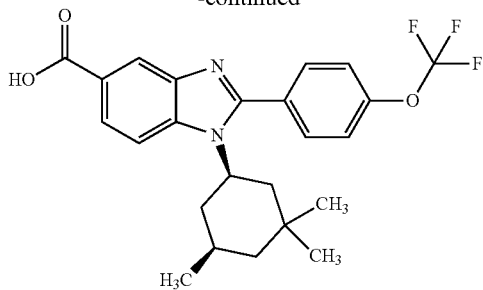

In analogy to example 2-2: Methyl 2-[4-(trifluoromethoxy)phenyl]-1-[(cis)-3,3,5-trimethylcyclohexyl]-1H-benzimidazole-5-carboxylate, enantiomer B (example 2-1-2; 115 mg, 0.250 mmol) was reacted with lithium hydroxide (5.0 eq., 30 mg, 1.2 mmol) in a mixture of THF/water (1:1, 4 mL) at 70° C. overnight to give the crude title compound (78 mg, 67%) which was not further purified.

$^1$H-NMR (400MHz, DMSO-d$_6$): δ [ppm]=0.84 (s, 3H), 0.90 (d, 3H), 0.99 (s, 3H), 1.09 (t, 1H), 1.32-1.35 (m, 1H), 1.60-1.72 (m, 2H), 1.82-1.93 (m, 2H), 2.10 (t, 1H), 4.44-4.52 (m, 1H), 7.58-7.60 (m, 2H), 7.81-7.84 (m, 2H), 7.87 (dd, 1H), 7.97 (d, 1H), 8.26 (d, 1H), 12.77 (s, 1H).

UPLC-MS (ESI+): [M+H]$^+$=447; R=1.54 min (Method E).

Example 2-3

(±) methyl 2-[4-(trifluoromethoxy)benzyl]-1-[(cis)-3,3,5-trimethylcyclohexyl]-1H-benzimidazole-5-carboxylate

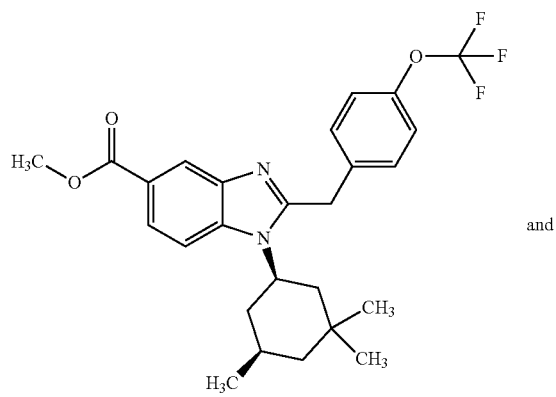

In a pressure tube a mixture of (±) methyl 3-amino-4-{[(cis)-3,3,5-trimethylcyclohexyl]amino}benzoate (intermediate 1-1; 200 mg, 0.689 mmol) and [4-(trifluoromethoxy)phenyl]acetic acid (CAS No. [4315-07-5]; 1.20 eq, 182 mg, 0.826 mmol) in ethyl acetate (2 mL) was treated with pyridine (25 eq., 1.4 mL, 17 mmol) and 2,4,6-tripropyl-1,3,5,2,4,6-trioxatriphosphinane 2,4,6-trioxide (CAS No. [68957-94-8]; 50 wt. % sol. in DMF, 5.0 eq., 2.2 g, 2.0 mL, 3.4 mmol), the tube sealed and stirred at 100° C. overnight. Upon cooling to rt the reaction mixture was partitioned between water and ethyl acetate and the layers separated. The organic layer was washed with brine, dried with sodium sulfate and concentrated in vacuo. The obtained material was purified by preparative HPLC to give the title compound (165 mg, 50%).

$^1$H-NMR (300 MHz, DMSO-d$_6$): δ [ppm]=0.69 (s, 3H), 0.83 (s, 3H), 0.86 (d, 3H), 0.93-1.05 (m, 2H), 1.26-1.31 (m, 1H), 1.58-1.71 (m, 3H), 1.87 (t, 1H), 3.87 (s, 3H), 4.33-4.42 (m, 2H), 4.55 (d, 1H), 7.33 (s, 4H), 7.76-7.83 (m, 2H), 8.18-8.20 (m, 1H).

UPLC-MS (ESI+): [M+H]$^+$=475; R$_t$=1.64 min (Method E).

The enantiomers of the racemic material of example 2-3 were separated by chiral preparative HPLC (System: Agilent: Prep 1200, 2× Prep Pump, DLA, MWD, Prep FC; Column: Chiralpak IA 5 μm 250×30 mm; Solvent: hexane/2-propanol 70:30 (v/v); Flow: 50 mL/min; Temperature: rt; Solution: 130 mg/1.8 mL DCM; Injection: 3×0.6 mL; Detection: UV 254 nm) and analytically characterized by chiral HPLC (System: Waters: Alliance 2695, DAD 996, ESA: Corona; Column: Chiralpak IA 3 μm 100×4.6 mm; Solvent: hexane/2-propanol 70:30 (v/v); Flow: 1.0 mL/min; Temperature: 25° C.; Solution: 1.0 mg/mL EtOH/MeOH 1:1; Injection: 5.0 μL; Detection: DAD 254 nm):

Example 2-3-1 methyl 2-[4-(trifluoromethoxy)benzyl]-1-[(cis)-3,3,5-trimethylcyclohexyl]-1H-benzimidazole-5-carboxylate, Enantiomer A

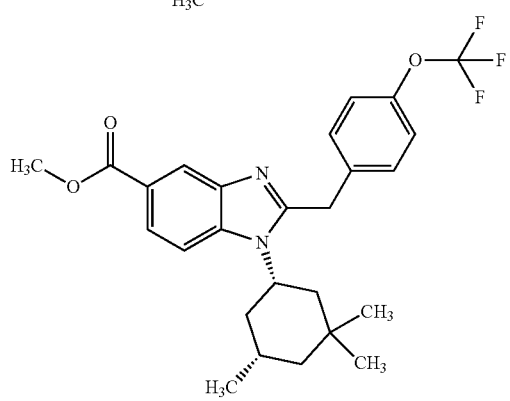

and

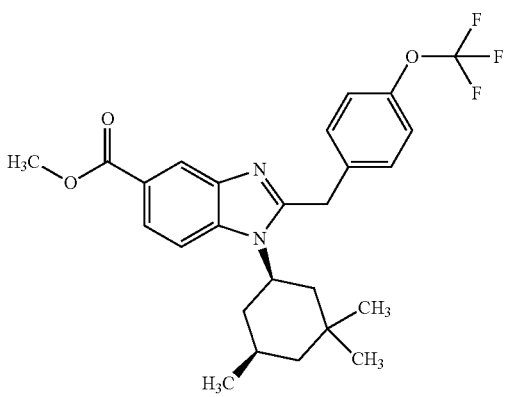

or

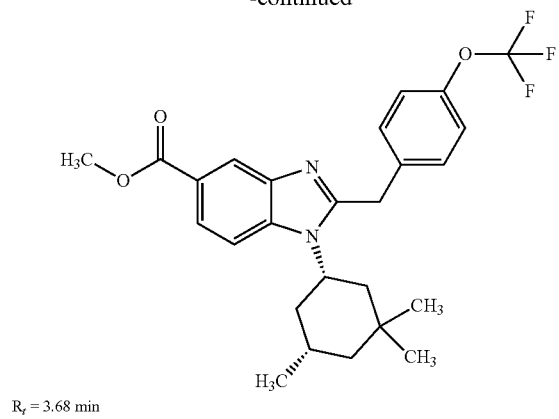

R_t = 3.68 min

Example 2-3-2 methyl 2-[4-(trifluoromethoxy)benzyl]-1-[(cis)-3,3,5-trimethylcyclohexyl]-1H-benzimidazole-5-carboxylate, Enantiomer B

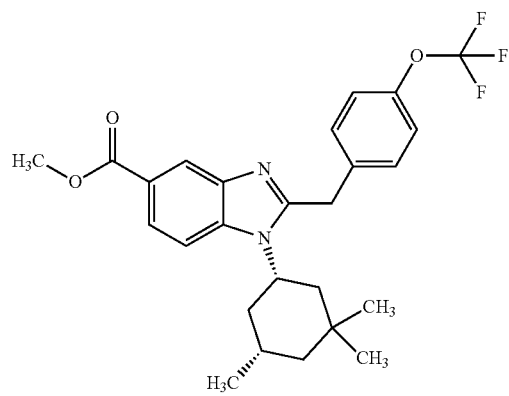

or

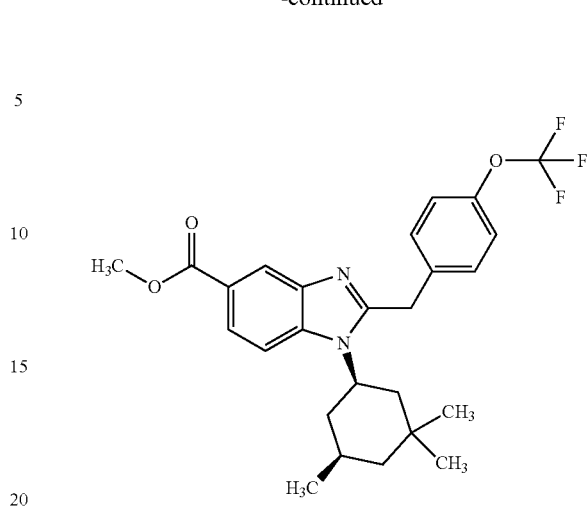

R_t = 5.09 min

The reference compounds in Table 2 were prepared in an analogous manner to example 2-3, starting from the given intermediates and the corresponding commercially available carboxylic acid derivatives. The enantiomers/diastereomers were separated and analyzed according to the given procedures.

TABLE 2

| Reference Cpd.; Intermediate; Carboxylic Acid used | Structure/Name | Method/ Analytical data |
|---|---|---|
| Reference Cpd. 2-4 Intermediate 1-1 2-[4-(trifluoromethoxy) phenyl] propanoic acid [75908-73-5] | (structure) | $^1$H-NMR (300 MHz, DMSO-$d_6$): δ [ppm] = 0.44-0.52 (m, 1.5H*), 0.64-0.72 (m, 3H), 0.89-0.98 (m, 6H), 1.24-1.28 (m, 2H), 1.41-1.52 (m, 1.5H*), 1.68-1.82 (m, 4.5H*), 2.01 (t, 0.5H*), 3.87 (s, 3H), 4.22-4.36 (m, 1H), 4.64 (q, 0.5H*), 4.84 (q, 0.5H*), 7.24-7.37 (m, 4H), 7.77-7.79 (m, 2H), 8.25-8.26 (m, 1H). UPLC-MS (ESI+): [M + H]$^+$ = 489; R_t = 1.66/1.71 min (Method E). | and

TABLE 2-continued

| Reference Cpd.; Intermediate; Carboxylic Acid used | Structure/Name | Method/ Analytical data |
|---|---|---|
| | 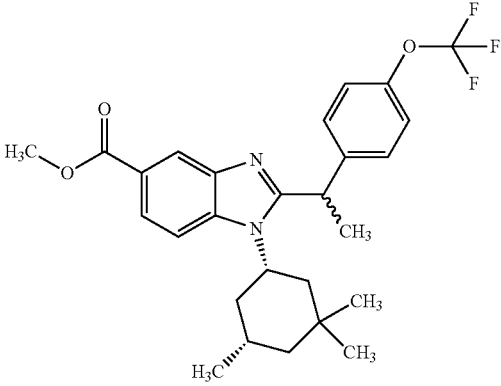methyl 2-{1-[4-(trifluoromethoxy)phenyl]ethyl}-1-[(cis)-3,3,5-trimethylcyclohexyl]-1H-benzimidazole-5-carboxylate | |
| Reference Cpd. 2-4-1 | methyl 2-{1-[4-(trifluoromethoxy)phenyl]ethyl}-1-[(cis)-3,3,5-trimethylcyclohexyl]-1H-benzimidazole-5-carboxylate, diastereomer A | Separation: System: Sepiatec: Prep SFC100; Column: Chiralpak IB 5 µm 250 × 30 mm; Solvent: $CO_2$/2-propanol 93/7; Flow: 100 mL/min; Pressure (outlet): 150 bar; Temperature: 40° C.; Solution: 211 mg/3.6 mL MeOH; Injection: 12 × 0.3 mL; Detection: UV 254 nm. Analysis: System: Agilent: 1260 AS, MWD, Aurora SFC-Module; Column: Chiralpak IB 5 µm 100 × 4.6 mm; Solvent: $CO_2$/2-propanol 93/7; Flow: 4.0 mL/min; Pressure (outlet): 100 bar; Temperature: 37.5° C.; Solution: 1.0 mg/mL MeOH; Injection: 10.0 µL; Detection: DAD 254 nm: $R_t$ = 2.13 min |
| Reference Cpd. 2-4-2 | methyl 2-{1-[4-(trifluoromethoxy)phenyl]ethyl}-1-[(cis)-3,3,5-trimethylcyclohexyl]-1H-benzimidazole-5-carboxylate, diastereomer B | $R_t$ = 3.26 min |
| Reference Cpd. 2-4-3 | methyl 2-{1-[4-(trifluoromethoxy)phenyl]ethyl}-1-[(cis)-3,3,5-trimethylcyclohexyl]-1H-benzimidazole-5-carboxylate, diastereomer C | $R_t$ = 4.26 min |
| Reference Cpd. 2-4-4 | methyl 2-{1-[4-(trifluoromethoxy)phenyl]ethyl}-1-[(cis)-3,3,5-trmethylcyclohexyl]-1H-benzimidazole-5-carboxylate, diastereomer D | $R_t$ = 5.18 min |

TABLE 2-continued

| Reference Cpd.; Intermediate; Carboxylic Acid used | Structure/Name | Method/ Analytical data |
| --- | --- | --- |
| Reference Cpd. 2-5 Intermediate 1-1 2-methyl-2-[4-(trifluoromethoxy) phenyl] propanoic acid [1260795-43-4] | 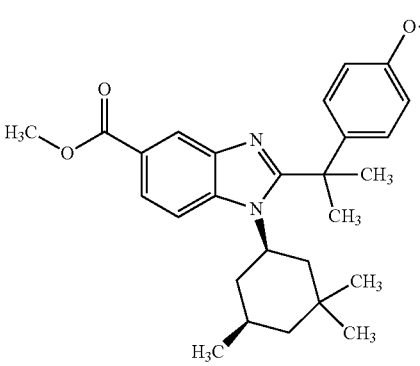 and 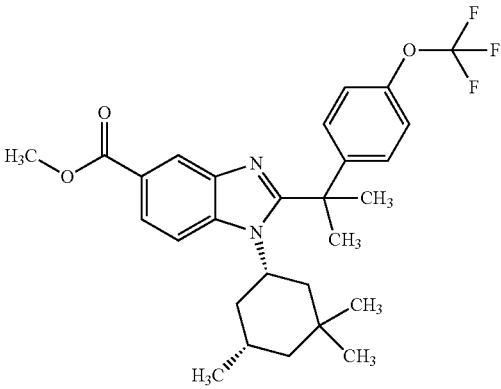 (±) methyl 2-{2-[4-(trifluoromethoxy)phenyl]propan-2-yl}-1-[(cis)-3,3,5-trimethylcyclohexyl]-1H-benzimidazole-5-carboxylate | $^1$H-NMR (400 MHz, DMSO-$d_6$): δ [ppm] = 0.54 (s, 3H), 0.73 (d, 3H), 0.85 (s, 3H), 0.96-0.98 (m, 1H), 1.10-1.12 (m, 2H), 1.18-1.21 (m, 2H), 1.56-1.59 (m, 1H), 1.76 (s, 3H), 1.81 (s, 3H), 1.95 (t, 1H), 3.87-3.95 (m, 4H), 7.31-7.33 (m, 2H), 7.37-7.39 (m, 2H), 7.77-7.81 (m, 2H), 8.26 (s, 1H). UPLC-MS (ESI+): [M + H]$^+$ = 503; R$_t$ = 1.74 min (Method E). |

The examples in Table 3 were prepared in an analogous manner to example 2-3, starting from the given intermediates and the corresponding commercially available carboxylic acid derivatives. The enantiomers/diastereomers were separated and analyzed according to the given procedures.

TABLE 3

| Example; Intermediate; Carboxylic Acid used | Structure/Name | Method/ Analytical data |
|---|---|---|
| Ex. 2-6 Intermediate 1-1 [4-(propan-2-yloxy)phenyl] acetic acid [55784-07-1] | 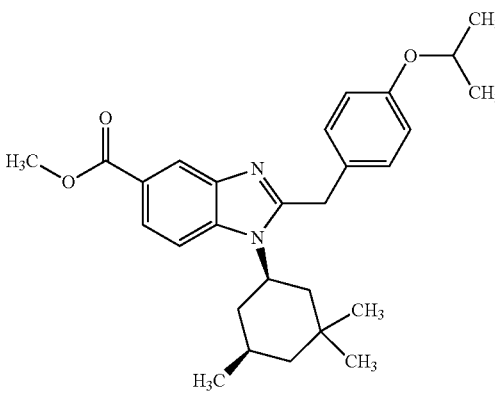<br><br>and<br><br>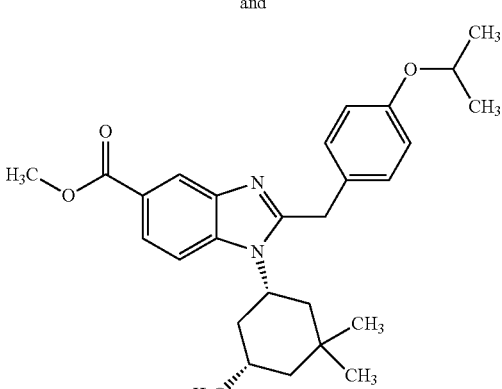<br><br>(±) methyl 2-[4-(propan-2-yloxy)benzyl]-1-[(cis)-3,3,5-trimethylcyclohexyl]-1H-benzimidazole-5-carboxylate | ¹H-NMR (400 MHz, DMSO-d₆): δ [ppm] = 0.74 (s, 3H), 0.84-0.87 (m, 6H), 0.98-1.05 (m, 2H), 1.21 (d, 6H), 1.27-1.30 (m, 1H), 1.52 (br. s., 1H), 1.63-1.67 (m, 2H), 1.87 (t, 1H), 3.87 (s, 3H), 4.25 (d, 1H), 4.36-4.44 (m, 2H), 4.54 (sept, 1H), 6.83-6.88 (m, 2H), 7.07-7.10 (m, 2H), 7.78 (d, 2H), 8.19 (s, 1H). UPLC-MS (ESI+): [M + H]⁺ = 449; $R_t$ = 1.61 min (Method E). |
| Ex. 2-6-1 | 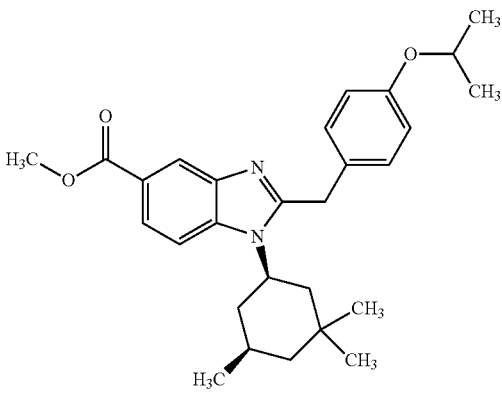<br><br>or | Separation: System: Sepiatec: Prep SFC100; Column: Chiralpak IA 5 μm 250 × 20 mm; Solvent: CO₂/2-propanol 75/25; Flow: 80 mL/min; Pressure (outlet): 150 bar; Temperature: 40° C.; Solution: 167 mg/2 mL DCM; Injection: 20 × 0.1 mL; Detection: MWD 254 nm. Analysis: System: Agilent: 1260 AS, MWD, Aurora SFC-Module; Column: Chiralpak IA 5 μm 100 × 4.6 mm; Solvent: CO₂/2-propanol 75/25; Flow: 4.0 mL/min; Pressure (outlet): 100 bar; Temperature: 37.5° C.; Solution: 1.0 mg/mL MeOH; Injection: 5 μL; Detection: MWD 254 nm: $R_t$ = 1.85 min |

TABLE 3-continued
| Example;<br>Intermediate;<br>Carboxylic<br>Acid used | Structure/Name | Method/<br>Analytical data |
|---|---|---|
| | 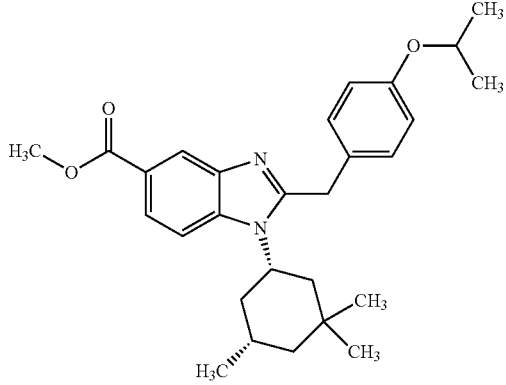<br>methyl 2-[4-(propan-2-yloxy)benzyl]-1-[(cis)-3,3,5-trimethylcyclohexyl]-1H-benzimidazole-5-carboxylate, enantiomer A | |
| Ex. 2-6-2 | 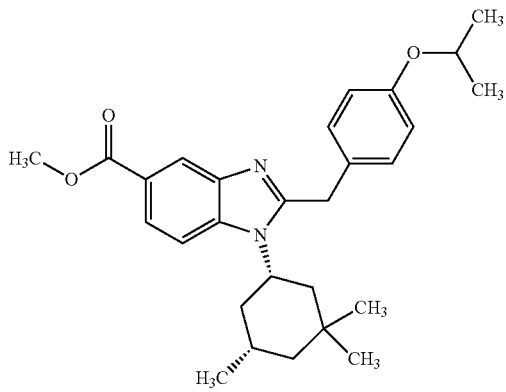<br>or<br>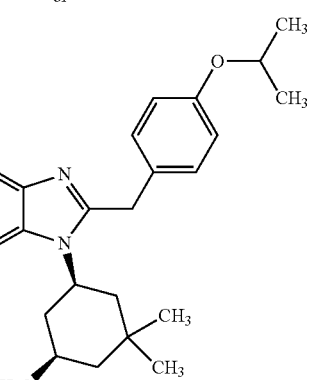<br>methyl 2-[4-(propan-2-yloxy)benzyl]-1-[(cis)-3,3,5-trimethylcyclohexyl]-1H-benzimidazole-5-carboxylate, enantiomer B | $R_t$ = 2.48 min |

TABLE 3-continued

| Example; Intermediate; Carboxylic Acid used | Structure/Name | Method/ Analytical data |
|---|---|---|
| Ex. 2-7 Intermediate 1-1 [4-(propan-2-yl)phenyl] acetic acid [4476-28-2] | 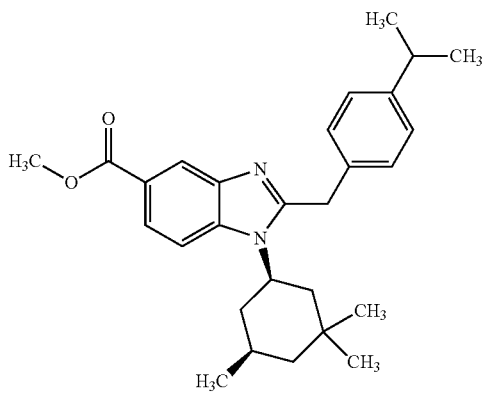<br>and<br>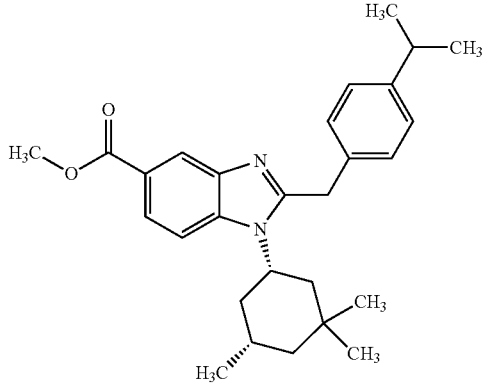<br>(±) methyl 2-[4-(propan-2-yl)benzyl]-1-[(cis)-3,3,5-trimethylcyclohexyl]-1H-benzimidazole-5-carboxylate | $^1$H-NMR (400 MHz, DMSO-$d_6$): δ [ppm] = 0.68 (s, 3H), 0.82 (br. s., 6H), 0.94-1.03 (m, 2H), 1.15 (d, 6H), 1.25-1.28 (m, 1H), 1.45-1.47 (m, 1H), 1.60-1.64 (m, 2H), 1.84 (t, 1H), 2.84 (sept, 1H), 3.87 (s, 3H), 4.28-4.44 (m, 3H), 7.08-7.11 (m, 2H), 7.16-7.18 (m, 2H), 7.78 (d, 2H), 8.20 (s, 1H). UPLC-MS (ESI+): [M + H]$^+$ = 433; R$_t$ = 1.72 min (Method E). |
| Ex. 2-8 Intermediate 1-1 [4-(trifluoromethyl) phenyl] acetic acid [32857-62-8] | 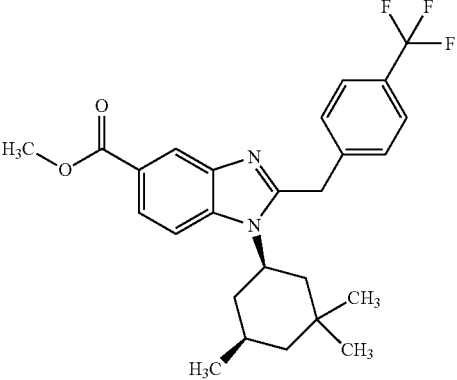<br>and | $^1$H-NMR (400 MHz, DMSO-$d_6$): δ [ppm] = 0.68 (s, 3H), 0.84-0.86 (m, 6H), 0.98-1.04 (m, 2H), 1.27-1.30 (m, 1H), 1.59-1.70 (m, 3H), 1.89 (t, 1H), 3.87 (s, 3H), 4.32-4.39 (m, 1H), 4.47 (d, 1H), 4.61 (d, 1H), 7.44-7.46 (m, 2H), 7.69-7.71 (m, 2H), 7.79 (dd, 1H), 7.83 (d, 1H), 8.20 (d, 1H). UPLC-MS (ESI+): [M + H]$^+$ = 459; R$_t$ = 1.62 min (Method E). |

TABLE 3-continued

| Example; Intermediate; Carboxylic Acid used | Structure/Name | Method/ Analytical data |
|---|---|---|
| | (±) methyl 2-[4-(trifluoromethyl)benzyl]-1-[(cis)-3,3,5-trimethylcyclohexyl]-1H-benzimidazole-5-carboxylate | |
| Ex. 2-9 Intermediate 1-1 (4-fluorophenyl) acetic acid [405-50-5] | (±) methyl 2-(4-fluorobenzyl)-1-[(cis)-3,3,5-trimethylcyclohexyl]-1H-benzimidazole-5-carboxylate and | $^1$H-NMR (400 MHz, DMSO-d$_6$): δ [ppm] = 0.74 (s, 3H), 0.86-0.87 (m, 6H), 0.98-1.05 (m, 2H), 1.28-1.32 (m, 1H), 1.60-1.71 (m, 3H), 1.89 (t, 1H), 3.87 (s, 3H), 4.33 (d, 1H), 4.37-4.44 (m, 1H), 4.48 (d, 1H), 7.13-7.18 (m, 2H), 7.24-7.27 (m, 2H), 7.78 (dd, 1H), 7.81 (d, 1H), 8.19 (s, 1H). UPLC-MS (ESI+): [M + H]$^+$ = 409; R$_t$ = 1.53 min (Method E). |

TABLE 3-continued

| Example; Intermediate; Carboxylic Acid used | Structure/Name | Method/ Analytical data |
|---|---|---|
| Ex. 2-10 Intermediate 1-1 (4-methyl-phenyl) acetic acid [622-47-9] | 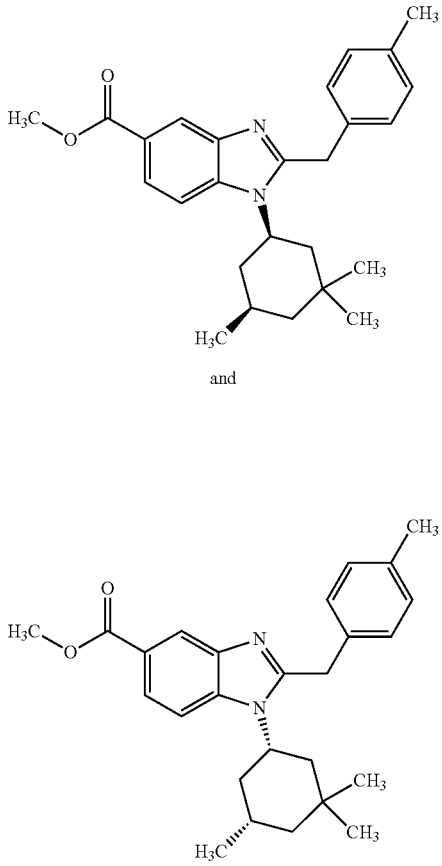<br><br>(±) methyl 2-(4-methylbenzyl)-1-[(cis)-3,3,5-trimethylcyclohexyl]-1H-benzimidazole-5-carboxylate | $^1$H-NMR (400 MHz, DMSO-d$_6$): δ [ppm] = 0.72 (s, 3H), 0.83-0.84 (m, 6H), 0.96-1.06 (m, 2H), 1.26-1.30 (m, 1H), 1.51-1.52 (m, 1H), 1.59-1.66 (m, 2H), 1.87 (t, 1H), 2.25 (s, 3H), 3.86 (s, 3H), 4.27 (d, 1H), 4.38-4.44 (m, 2H), 7.07-7.12 (m, 4H), 7.75-7.79 (m, 2H), 8.18 (s, 1H). UPLC-MS (ESI+): [M + H]$^+$ = 405; R$_t$ = 1.59 min (Method E). |
| Ex. 2-11 Intermediate 1-1 (4-tert-butyl-phenyl) acetic acid [32857-63-9] | 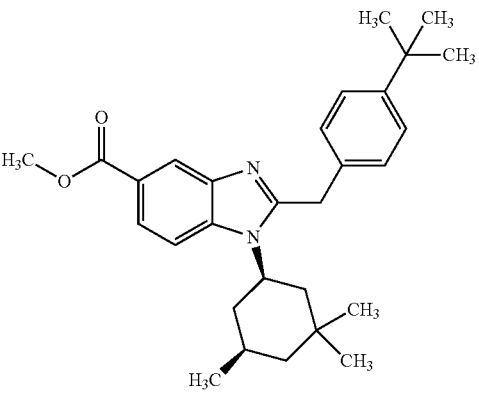 | $^1$H-NMR (400 MHz, DMSO-d$_6$): δ [ppm] = 0.68 (s, 3H), 0.81-0.82 (m, 6H), 0.94-1.01 (m, 2H), 1.24-1.28 (m, 10H), 1.44-1.45 (m, 1H), 1.59-1.63 (m, 2H), 1.84 (t, 1H), 3.87 (s, 3H), 4.30 (d, 1H), 4.35-4.39 (m, 1H), 4.42 (d, 1H), 7.09-7.12 (m, 2H), 7.31-7.34 (m, 2H), 7.77 (d, 2H), 8.20 (s, 1H). UPLC-MS (ESI+): [M + H]$^+$ = 447; R$_t$ = 1.75 min (Method E). |

TABLE 3-continued

| Example; Intermediate; Carboxylic Acid used | Structure/Name | Method/ Analytical data |
| --- | --- | --- |
| | (±) methyl 2-(4-tert-butylbenzyl)-1-[(cis)-3,3,5-trimethylcyclohexyl]-1H-benzimidazole-5-carboxylate | |
| Ex. 2-12 Intermediate 1-1 phenylacetic acid [103-82-2] | (±) methyl 2-benzyl-1-[(cis)-3,3,5-trimethylcyclohexyl]-1H-benzimidazole-5-carboxylate<br>and | $^1$H-NMR (400 MHz, DMSO-d$_6$): δ [ppm] = 0.71 (s, 3H), 0.84-0.85 (m, 6H), 1.00-1.03 (m, 2H), 1.27-1.30 (m, 1H), 1.54-1.55 (m, 1H), 1.64-1.71 (m, 2H), 1.87 (t, 1H), 3.87 (s, 3H), 4.34 (d, 1H), 4.39-4.43 (m, 1H), 4.47 (d, 1H), 7.20-7.26 (m, 3H), 7.30-7.36 (m, 2H), 7.76-7.81 (m, 2H), 8.20 (s, 1H). UPLC-MS (ESI+): [M + H]$^+$ = 391; R$_t$ = 1.53 min (Method E). |
| Ex. 2-13 Intermediate 1-1 [2-(trifluoro-methoxy)phenyl] acetic acid [220239-67-8] | and | $^1$H-NMR (300 MHz, DMSO-d$_6$): δ [ppm] = 0.74 (s, 3H), 0.85-0.89 (m, 6H), 0.97-1.07 (m, 1H), 1.20-1.34 (m, 2H), 1.57-1.72 (m, 3H), 1.96 (t, 1H), 3.86 (s, 3H), 4.25-4.41 (m, 2H), 4.47 (d, 1H), 7.18 (d, 1H), 7.32-7.38 (m, 1H), 7.40-7.44 (m, 2H), 7.79 (d, 1H), 7.85 (d, 1H), 8.17 (d, 1H). UPLC-MS (ESI+): [M + H]$^+$ = 475; R$_t$ = 1.65 min (Method E). |

TABLE 3-continued

| Example; Intermediate; Carboxylic Acid used | Structure/Name | Method/ Analytical data |
|---|---|---|
| | (± methyl 2-[2-(trifluoromethoxy)benzyl]-1-[(cis)-3,3,5-trimethylcyclohexyl]-1H-benzimidazole-5-carboxylate | |
| Ex. 2-14 Intermediate 1-1 [3-(trifluoromethoxy)phenyl] acetic acid [203302-97-0] | and<br><br>(±) methyl 2-[3-(trifluoromethoxy)benzyl]-1-[(cis)-3,3,5-trimethylcyclohexyl]-1H-benzimidazole-5-carboxylate | UPLC-MS (ESI+): [M + H]$^+$ = 475; R$_t$ = 1.64 min (Method E). |

TABLE 3-continued

| Example; Intermediate; Carboxylic Acid used | Structure/Name | Method/ Analytical data |
|---|---|---|
| Ex. 2-15 Intermediate 1-1 (4-methyl-2-phenyl-1,3-thiazol-5-yl)acetic acid [34272-67-8] | 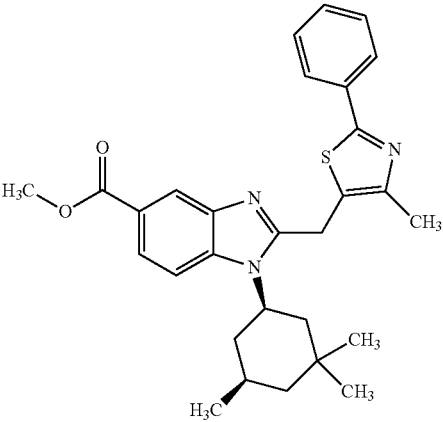<br>and<br>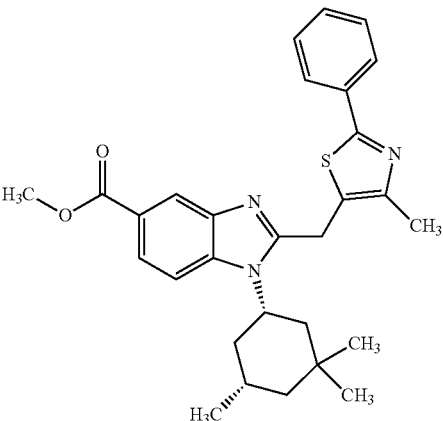<br>(±) methyl 2-[(4-methyl-2-phenyl-1,3-thiazol-5-yl)methyl]-1-[(cis)-3,3,5-trimethylcyclohexyl]-1H-benzimidazole-5-carboxylate | UPLC-MS (ESI+): [M + H]$^+$ = 488; R$_t$ = 1.62 min (Method A). |
| Ex. 2-16 Intermediate 1-1 (5-fluoro-2-methyl-1H-indol-3-yl)acetic acid [71987-67-2] | 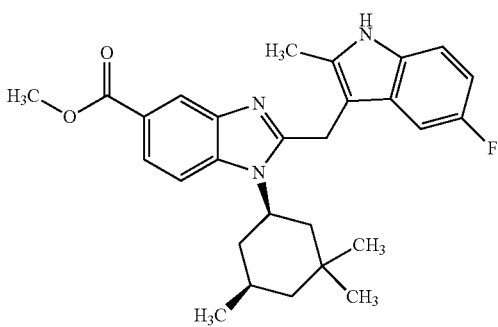<br>and | UPLC-MS (ESI+): [M + H]$^+$ = 462; R$_t$ = 1.41 min (Method E). |

TABLE 3-continued

| Example; Intermediate; Carboxylic Acid used | Structure/Name | Method/ Analytical data |
|---|---|---|
| | (±) methyl 2-[(5-fluoro-2-methyl-1H-indol-3-yl)methyl]-1-[(cis)-3,3,5-trimethylcyclohexyl]-1H-benzimidazole-5-carboxylate | |
| Ex. 2-17 Intermediate 1-1 (1-methyl-1H-indol-3-yl)acetic acid [1912-48-7] | and<br><br>(±) methyl 2-[(1-methyl-1H-indol-3-yl)methyl]-1-[(cis)-3,3,5-trimethylcyclohexyl]-1H-benzimidazole-5-carboxylate | UPLC-MS (ESI+): [M + H]$^+$ = 444; R$_t$ = 1.50 min (Method E). |

TABLE 3-continued

| Example;<br>Intermediate;<br>Carboxylic<br>Acid used | Structure/Name | Method/<br>Analytical data |
|---|---|---|
| Ex. 2-18<br>Intermediate<br>1-2 [4-<br>(trifluoro-<br>methoxy)<br>phenyl]<br>acetic acid<br>[4315-07-5] | ![structure] <br><br>and<br><br>![structure]<br><br>(±) methyl 6-methyl-2-[4-<br>(trifluoromethoxy)benzyl]-1-[(cis)-<br>3,3,5-trimethylcyclohexyl]-1H-<br>benzimidazole-5-carboxylate | $^1$H-NMR (400 MHz, DMSO-d$_6$): δ<br>[ppm] = 0.69 (s, 3H), 0.84-0.87 (m, 6H), 0.93-0.96<br>(m, 1H), 1.04 (t, 1H), 1.24-1.29 (m, 1H), 1.52-<br>1.53 (m, 1H), 1.66-1.74 (m, 2H),<br>1.88 (t, 1H), 2.64 (s, 3H), 3.83 (s, 3H),<br>4.27-4.37 (m, 2H), 4.50 (d, 1H), 7.31 (s, 4H), 7.59<br>(s,1H), 8.11 (s, 1H). UPLC-MS (ESI+): [M + H]$^+$ =<br>489; R$_t$ = 1.69 min (Method F). |
| Ex. 2-18-1 | ![structure]<br><br>or | Separation:<br>System: Agilent: Prep 1200, 2 × Prep Pump, DLA,<br>MWD, Prep FC; Column: Chiralpak IC 5 μm<br>250 × 30 mm No.: 009 BF; Solvent: hexane/2-propanol/<br>diethylamine 70:30:0.1 (v/v/v);<br>Flow: 50 mL/min; Temperature: rt;<br>Solution: 250 mg/2.5 mL DCM/MeOH; Injection: 5 ×<br>0.5 mL; Detection: UV 254 nm. Analysis:<br>System: Waters: Alliance 2695, DAD 996, ESA: Corona;<br>Column: Chiralpak IC 3 μm 100 × 4.6 mm;<br>Solvent: hexane/2-propanol/diethylamine 70:30:0.1<br>(v/v/v); Flow: 1.0 mL/min; Temperature:<br>25° C.; Solution: 1.0 mg/mL EtOH/MeOH 1:1; Injection:<br>5.0 μL; Detection: DAD 254 nm:<br>R$_t$ = 4.96 min |

TABLE 3-continued
| Example; Intermediate; Carboxylic Acid used | Structure/Name | Method/ Analytical data |
|---|---|---|
| | 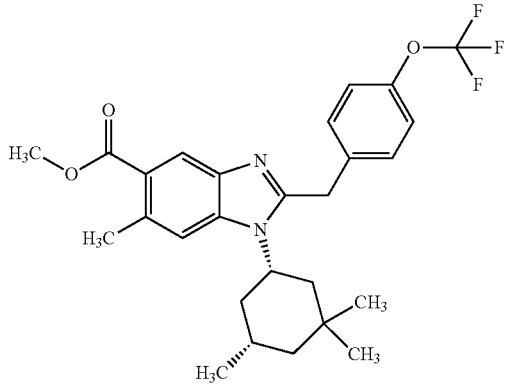<br>methyl 6-methyl-2-[4-(trifluoromethoxy)benzyl]-1-[(cis)-3,3,5-trimethylcyclohexyl]-1H-benzimidazole-5-carboxylate, enantiomer A | |
| Ex. 2-18-2 | 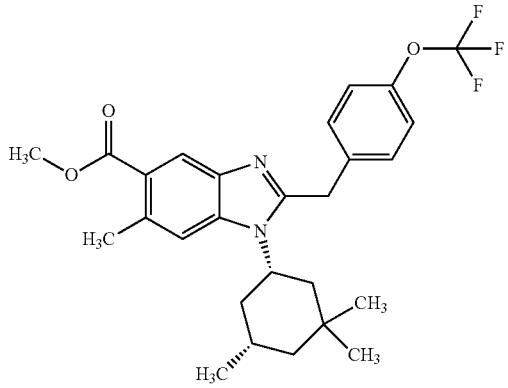<br>or<br>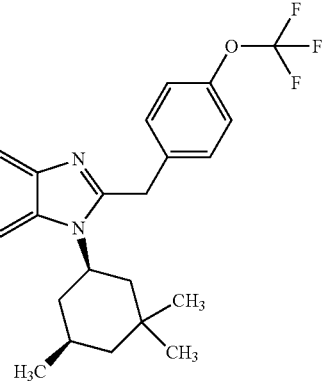<br>methyl 6-methyl-2[4-(trifluoromethoxy)benzyl]-1-[(cis)-3,3,5-trimethylcyclohexyl]-1H-benzimidazole-5-carboxylate, enantiomer B | $R_t$ = 5.79 min |

| Example; Intermediate; Carboxylic Acid used | Structure/Name | Method/ Analytical data |
|---|---|---|
| Ex. 2-19 Intermediate 1-4 [4-(trifluoro-methoxy) phenyl] acetic acid [4315-07-5] | [structure of methyl 6-methoxy-2-[4-(trifluoromethoxy)benzyl]-1-[(cis)-3,3,5-trimethylcyclohexyl]-1H-benzimidazole-5-carboxylate] and [second structure] (±) methyl 6-methoxy-2-[4-(trifluoromethoxy)benzyl]-1-[(cis)-3,3,5-trimethylcyclohexyl]-1H-benzimidazole-5-carboxylate | $^1$H-NMR (400 MHz, DMSO-d$_6$): δ [ppm] = 0.70 (s, 3H), 0.85-0.87 (m, 6H), 0.95-1.04 (m, 2H), 1.26-1.30 (m, 1H), 1.55 (br. s., 1H), 1.61-1.68 (m, 2H), 1.85 (t, 1H), 3.79 (s, 3H), 3.86 (s, 3H), 4.27-4.35 (m, 2H), 4.48 (d, 1H), 7.12 (s, 1H), 7.31 (s, 4H), 7.90 (s, 1H). UPLC-MS (ESI+): [M + H]$^+$ = 505; R$_t$ = 1.59 min (Method F). |
| Ex. 2-19-1 | [structure] or | Separation: System: Sepiatec: Prep SFC100; Column: Chiralpak IB 5 μm 250 × 20 mm; Solvent: CO$_2$/2-propanol 89/11; Flow: 80 mL/min; Pressure (outlet): 150 bar; Temperature: 40° C.; Solution: 328 mg/3 mL DCM/MeOH 1:1; Injection: 10 × 0.3 mL; Detection: UV 254 nm. Analysis: System: Agilent: 1260 AS, MWD, Aurora SFC-Module; Column: Chiralpak IB 5 μm 100 × 4.6 mm; Solvent: CO$_2$/2-propanol 89/11; Flow: 4.0 mL/min; Pressure (outlet): 100 bar; Temperature: 37.5° C.; Solution: 1.0 mg/mL EtOH/MeOH; Injection: 10.0 μL; Detection: DAD 254 nm: R$_t$ = 2.34 min |

TABLE 3-continued
| Example; Intermediate; Carboxylic Acid used | Structure/Name | Method/ Analytical data |
|---|---|---|
| | 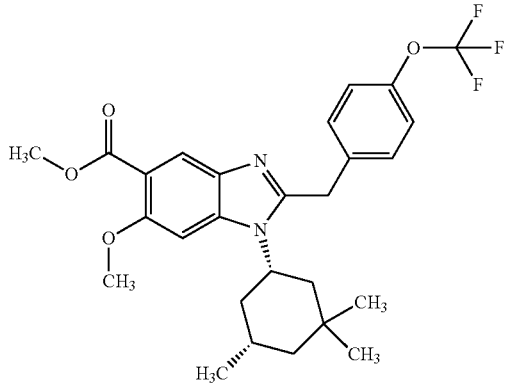methyl 6-methoxy-2-[4-(trifluoromethoxy)benzyl]-1-[(cis)-3,3,5-trimethylcyclohexyl]-1H-benzimidazole-5-carboxylate, enantiomer A | |
| Ex. 2-19-2 | 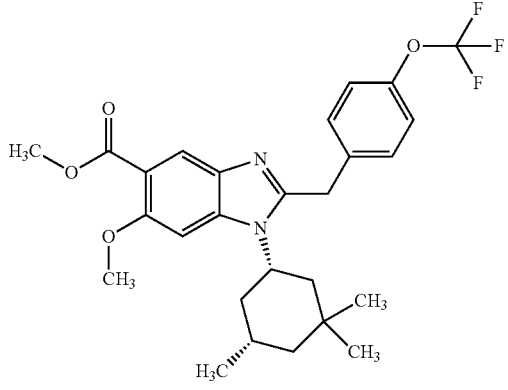or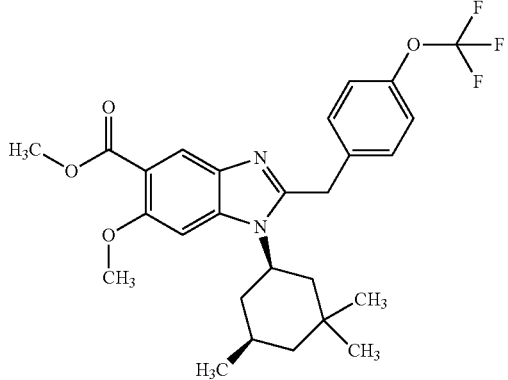methyl 6-methoxy-2-[4-(trifluoromethoxy)benzyl]-1-[(cis)-3,3,5-trimethylcyclohexyl]-1H-benzimidazole-5-carboxylate, enantiomer B | $R_t$ = 3.86 min |

TABLE 3-continued

| Example; Intermediate; Carboxylic Acid used | Structure/Name | Method/ Analytical data |
|---|---|---|
| Ex. 2-20 Intermediate 1-7 [4-(trifluoro-methoxy) phenyl] acetic acid [4315-07-5] | 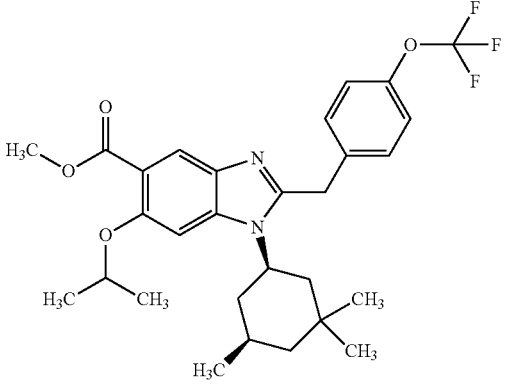  and  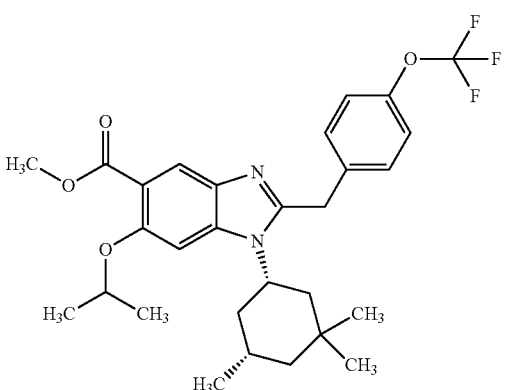  (±) methyl 6-(propan-2-yloxy)-2[4-(trifluoromethoxy)benzyl]-1-[(cis)-3,3,5-trimethylcyclohexyl]-1H-benzimidazole-5-carboxylate | $^1$H-NMR (400 MHz, DMSO-d$_6$): δ [ppm] = 0.69 (s, 3H), 0.84-0.87 (m, 6H), 0.95-1.03 (m, 2H), 1.26-1.29 (m, 7H), 1.57-1.65 (m, 3H), 1.80 (t, 1H), 3.79 (s, 3H), 4.27-4.35 (m, 2H), 4.48 (d, 1H), 4.60 (sept, 1H), 7.16 (s, 1H), 7.32 (s, 4H), 7.88 (s, 1H). UPLC-MS (ESI+): [M + H]$^+$ = 533; R$_t$ = 1.71 min (Method F). |
| Ex. 2-20-1 | 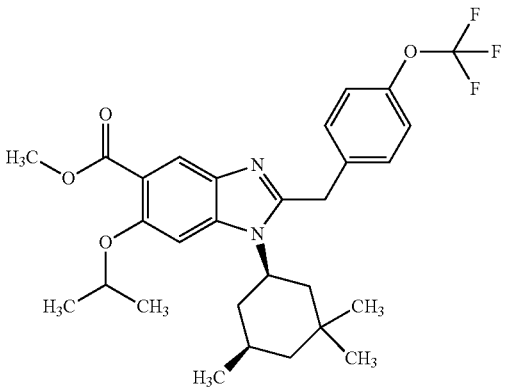  or | Separation: System: Agilent: Prep 1200, 2 × Prep Pump, DLA, MWD, Prep FC; Column: Chiralpak IC 5 μm 250 × 20 mm; Solvent: hexane/ ethanol/diethylamine 71:29:0.1 (v/v/v); Flow: 15 mL/min; Temperature: rt; Solution: 110 mg/ 1.5 mL DCM/MeOH 1:1; Injection: 16 × 0.1 mL; Detection: UV 254 nm. Analysis: System: Agilent 1260/ Agilent 1290; Column: Chiralpak IC 3 μm 100 × 4.6 mm; Solvent: hexane/ethanol/diethylamine 71:29:0.1 (v/v/v); Flow: 1.0 mL/min Temperature: 25° C.; Solution: 1.0 mg/mL EtOH/MeOH 1:1; Injection: 5.0 μL; Detection: DAD 254 nm: R$_t$ = 3.96 min |

TABLE 3-continued

| Example; Intermediate; Carboxylic Acid used | Structure/Name | Method/ Analytical data |
|---|---|---|
| | 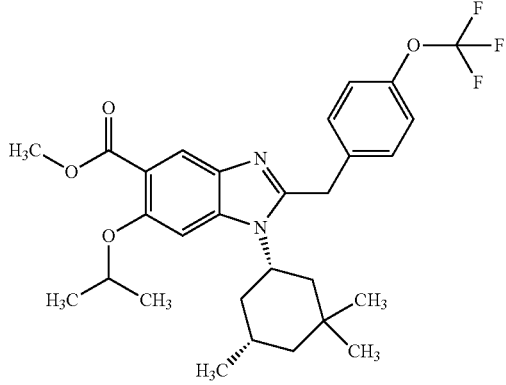<br>methyl 6-(propan-2-yloxy)-2-[4-(trifluoromethoxy)benzyl]-1-[(cis)-3,3,5-trimethylcyclohexyl]-1H-benzimidazole-5-carboxylate, enantiomer A | |
| Ex. 2-20-2 | 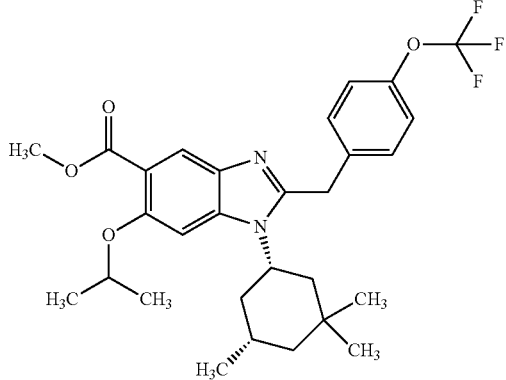<br>or<br>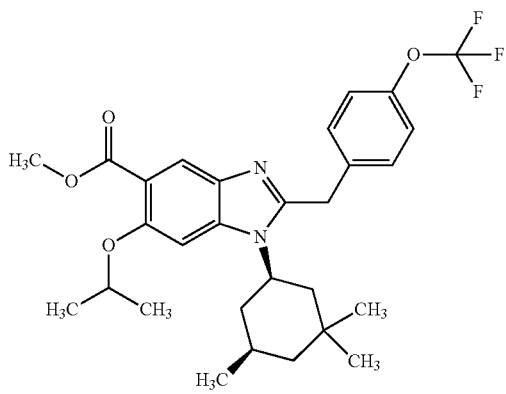<br>methyl 6-(propan-2-yloxy)-2-[4-(trifluoromethoxy)benzyl]-1-[(cis)-3,3,5-trimethylcyclohexyl]-1H-benzimidazole-5-carboxylate, enantiomer B | $R_t$ = 4.87 min |

TABLE 3-continued

| Example;<br>Intermediate;<br>Carboxylic<br>Acid used | Structure/Name | Method/<br>Analytical data |
|---|---|---|
| Ex. 2-21<br>Intermediate<br>1-8 [4-<br>(trifluoro-<br>methoxy)<br>phenyl]<br>acetic acid<br>[4315-07-5] | *structure*<br><br>and<br><br>*structure*<br><br>(±) methyl 6-(2,2,2-trifluoroethoxy)-<br>2-[4-(trifluoromethoxy)benzyl]-1-<br>[(cis)-3,3,5-trimethylcyclohexyl]-1H-<br>benzimidazole-5-carboxylate | UPLC-MS (ESI+): [M + H]⁺ = 573;<br>$R_t$ = 1.67 min (Method F). |
| Ex. 2-21-1 | *structure*<br><br>or | Separation: System: Agilent: Prep 1200, 2 × Prep Pump,<br>DLA, MWD, Gilson: Liquid Handler 215;<br>Column: Chiralpak IB 5 μm<br>250 × 20 mm; Solvent: hexane/2- propanol 80:20 (v/v);<br>Flow: 25 mL/min; Temperature: rt;<br>Solution: 100 mg/2 mL DCM/MeOH; Injection: 4 ×<br>0.5 mL; Detection: UV 254 nm. Analysis:<br>System: Agilent 1200; Column:<br>Chiralpak IB 3 μm 100 × 4.6 mm;<br>Solvent: hexane/2-propanol 80:20 (v/v); Flow: 1.0 mL/min;<br>Temperature: 25° C.; Solution: 1.0 mg/mL EtOH/MeOH<br>2:1; Injection: 5.0 μL; Detection: DAD<br>254 nm: $R_t$ = 2.45 min |

TABLE 3-continued

| Example; Intermediate; Carboxylic Acid used | Structure/Name | Method/ Analytical data |
|---|---|---|
| | 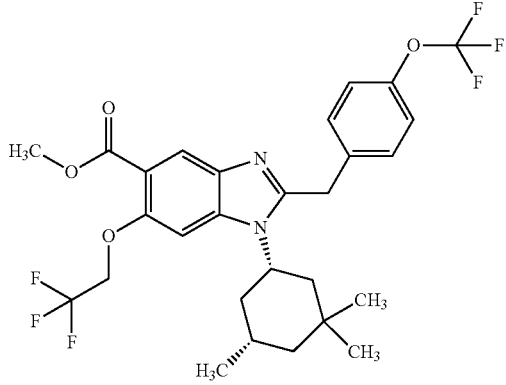

methyl 6-(2,2,2-trifluoroethoxy)-2-
[4-(trifluoromethoxy)benzyl]-1-
[(cis)-3,3,5-trimethylcyclohexyl]-1H-
benzimidazole-5-carboxylate,
enantiomer A | |
| Ex. 2-21-2 | 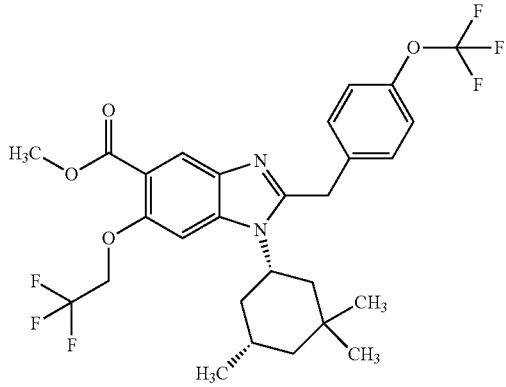

or

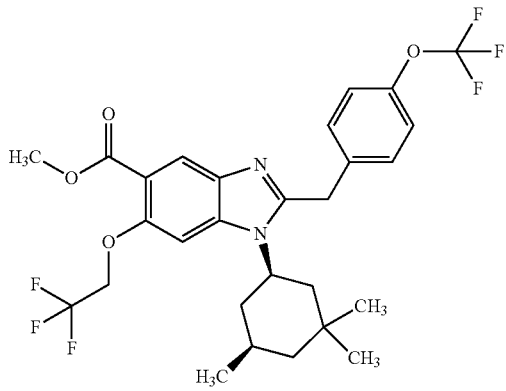

methyl 6-(2,2,2-trifluoroethoxy)-2-
[4-(trifluoromethoxy)benzyl]-1-
[(cis)-3,3,5-trimethylcyclohexyl]-1H-
benzimidazole-5-carboxylate,
enantiomer B | $R_t$ = 3.42 min |

TABLE 3-continued

| Example; Intermediate; Carboxylic Acid used | Structure/Name | Method/ Analytical data |
|---|---|---|
| Ex. 2-22 Intermediate 1-3 [4-(trifluoromethoxy) phenyl] acetic acid [4315-07-5] | methyl 4-fluoro-1-(3,3,5,5-tetramethylcyclohexyl)-2-[4-(trifluoromethoxy)benzyl]-1H-benzimidazole-5-carboxylate | $^1$H-NMR (300 MHz, DMSO-d$_6$): δ [ppm] = 0.76 (s, 6H), 0.86 (s, 6H), 1.07-1.28 (m, 4H), 1.94 (t, 2H), 3.88 (s, 3H), 4.24-4.32 (m, 1H), 4.48 (s, 2H), 7.29-7.36 (m, 4H), 7.64-7.73 (m, 2H). UPLC-MS (ESI+): [M + H]$^+$ = 507; R$_t$ = 1.70 min (Method E). |
| Ex. 2-23 Intermediate 1-9 [4-(trifluoromethoxy) phenyl] acetic acid [4315-07-5] | and (±) 2-[4-(trifluoromethoxy)benzyl]-1-[(cis)-3,3,5-trimethylcyclohexyl]-1H-benzimidazole-5-carbonitrile | UPLC-MS (ESI+): [M + H]$^+$ = 442; R$_t$ = 1.62 min (Method F). |

TABLE 3-continued

| Example; Intermediate; Carboxylic Acid used | Structure/Name | Method/ Analytical data |
| --- | --- | --- |
| Ex. 2-24 Intermediate 1-9 [4-(propan-2-yloxy)phenyl] acetic acid [55784-07-1] | (±) 2-[4-(propan-2-yloxy)benzyl]-1-[(cis)-3,3,5-trimethylcyclohexyl]-1H-benzimidazole-5-carbonitrile | $^1$H-NMR (400 MHz, DMSO-d$_6$): δ [ppm] = 0.75 (s, 3H), 0.83-0.84 (m, 6H), 0.99-1.04 (m, 2H), 1.21 (d, 6H), 1.26-1.29 (m, 1H), 1.52 (br. s., 1H), 1.62-1.66 (m, 2H), 1.85 (t, 1H), 4.26 (d, 1H), 4.38-4.46 (m, 2H), 4.55 (sept, 1H), 6.84-6.84 (m, 2H), 7.07-7.09 (m, 2H), 7.53 (dd, 1H), 7.89 (d, 1H)), 8.13 (d, 1H). UPLC-MS (ESI+): [M + H]$^+$ = 416; R$_t$ = 1.63 min (Method F). |
| Ex. 2-25 Intermediate 1-9 [4-(propan-2-yl)phenyl) phenyl]acetic acid [4476-28-2] | | UPLC-MS (ESI+): [M + H]$^+$ = 400; R$_t$ = 1.72 min (Method F). |

TABLE 3-continued

| Example; Intermediate; Carboxylic Acid used | Structure/Name | Method/ Analytical data |
|---|---|---|
| | (±) 2-[4-(propan-2-yl)benzyl]-1-[(cis)-3,3,5-trimethylcyclohexyl]-1H-benzimidazole-5-carbonitrile | |
| Ex. 2-26 Intermediate 1-9 [4-(trifluoromethyl)phenyl]acetic acid [32857-62-8] | and<br><br>(±) 2-[4-(trifluoromethyl)benzyl]-1-[(cis)-3,3,5-trimethylcyclohexyl]-1H-benzimidazole-5-carbonitrile | UPLC-MS (ESI+): [M + H]$^+$ = 426; R$_t$ = 1.60 min (Method F). |

TABLE 3-continued

| Example; Intermediate; Carboxylic Acid used | Structure/Name | Method/ Analytical data |
|---|---|---|
| Ex. 2-27 Intermediate 1-6 [4-(trifluoromethoxy) phenyl] acetic acid [4315-07-5] | *structure shown* and  (±) methyl 3-{6-methyl-2-[4-(trifluoromethoxy)benzyl]-1-[(cis)-3,3,5-trimethylcyclohexyl]-1H-benzimidazol-5-yl}propanoate | $^1$H-NMR (400 MHz, DMSO-$d_6$): δ [ppm] = 0.69 (s, 3H), 0.84-0.86 (m, 6H), 0.90-0.93 (m, 1H), 0.97-1.03 (m, 1H), 1.24-1.30 (m, 1H), 1.48-1.51 (m, 1H), 1.64-1.69 (m, 2H), 1.86 (t, 1H), 2.37 (s, 3H), 2.60-2.64 (m, 2H), 2.88-2.92 (m, 2H), 3.61 (s, 3H), 4.23-4.30 (m, 2H), 4.42 (d, 1H), 7.30 (s, 4H), 7.35 (s, 1H), 7.41 (s, 1H). UPLC-MS (ESI+): [M + H]$^+$ = 517; R$_t$ = 1.69 min (Method F). |

TABLE 3-continued

| Example; Intermediate; Carboxylic Acid used | Structure/Name | Method/ Analytical data |
|---|---|---|
| Ex. 2-28 Intermediate 1-5 [4-(trifluoromethoxy) phenyl] acetic acid [4315-07-5] | *(structure)* and *(structure)* (±) methyl 3-{6-methoxy-2-[4-(trifluoromethoxy)benzyl]-1-[(cis)-3,3,5-trimethylcyclohexyl]-1H-benzimidazol-5-yl}propanoate | $^1$H-NMR (400 MHz, DMSO-d$_6$): δ [ppm] = 0.70 (s, 3H), 0.84-0.87 (m, 6H), 0.92-1.01 (m, 2H), 1.27-1.30 (m, 1H), 1.50-1.53 (m, 1H), 1.60-1.67 (m, 2H), 1.84 (t, 1H), 2.56-2.60 (m, 2H), 2.86-2.89 (m, 2H), 3.59 (s, 3H), 3.84 (s, 3H), 4.25-4.31 (m, 2H), 4.42 (d, 1H), 6.97 (s, 1H), 7.27-7.32 (m, 4H), 7.35 (s, 1H). UPLC-MS (ESI+): [M + H]$^+$ = 533; R$_t$ = 1.66 min (Method F). |
| Ex. 2-28-1 | *(structure)* or | Separation: System: Agilent: Prep 1200, 2 × Prep Pump, DLA, MWD, Gilson: Liquid Handler 215; Column: Chiralpak IF 5 μm 250 × 20 mm; Solvent: hexane/ 2-propanol 80:20 (v/v); Flow: 25 mL/min; Temperature: rt; Solution: 120 mg/2.5 mL DCM/MeOH; Injection: 5 × 0.5 mL; Detection: UV 254 nm. Analysis: System: Agilent 1200; Column: Chiralpak IF 3 μm 100 × 4.6 mm; Solvent: hexane/2-propanol 80:20 (v/v); Flow: 1.0 mL/min; Temperature: 25° C.; Solution: 1.0 mg/mL EtOH/MeOH 2:1; Injection: 5.0 μL; Detection: DAD 254 nm: R$_t$ = 4.16 min |

TABLE 3-continued
| Example; Intermediate; Carboxylic Acid used | Structure/Name | Method/ Analytical data |
|---|---|---|
| | 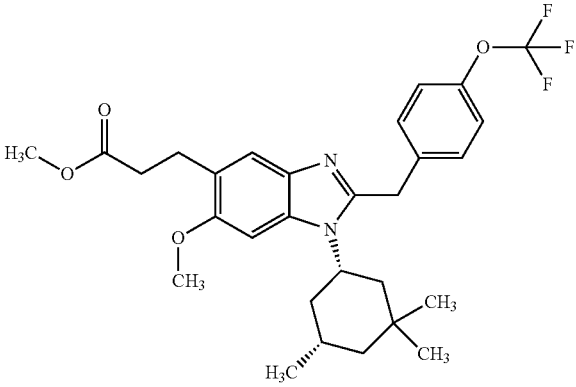<br>methyl 3-{6-methoxy-2-[4-(trifluoromethoxy)benzyl]-1-[(cis)-3,3,5-trimethylcyclohexyl]-1H-benzimidazol-5-yl}propanoate, enantiomer A | |
| Ex. 2-28-2 | 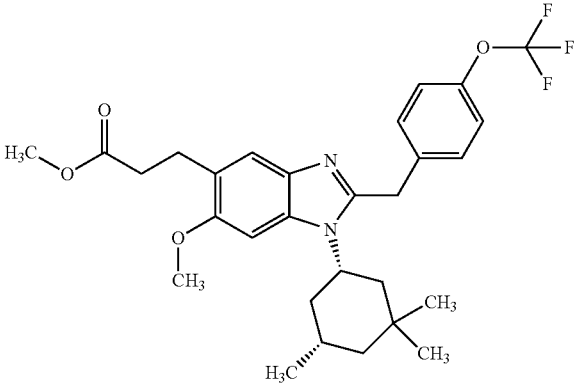<br>or<br>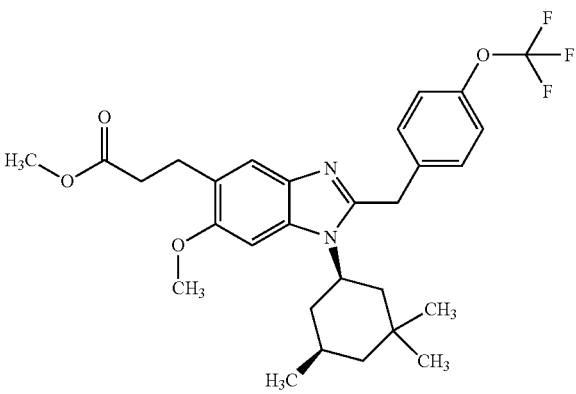<br>methyl 3-{6-methoxy-2-[4-(trifluoromethoxy)benzyl]-1-[(cis)-3,3,5-trimethylcyclohexyl]-1H-benzimidazol-5-yl}propanoate, enantiomer B | $R_t$ = 4.62 min |

Example 2-29

(±) 2-[4-(trifluoromethoxy)benzyl]-1-[(cis)-3,3,5-trimethylcyclohexyl]-1H-benzimidazole-5-carboxylic Acid

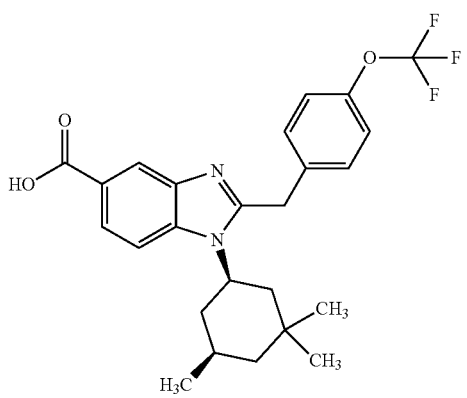

and

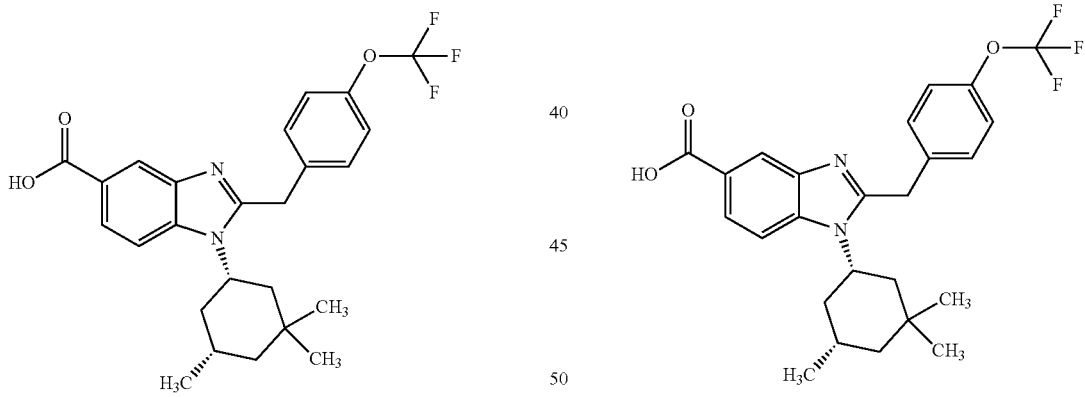

A solution of (±) methyl 2-[4-(trifluoromethoxy)benzyl]-1-[(cis)-3,3,5-trimethylcyclohexyl]-1H-benzimidazole-5-carboxylate (example 2-3; 35 mg, 0.0738 mmol) in a mixture of THF/water (1:1, 2 mL) was treated with lithium hydroxide (5.0 eq., 8.8 mg, 0.37 mmol) and stirred at 70° C. overnight. The reaction mixture was acidified with 2 M aqueous hydrochloric acid (pH 3-4) and diluted with ethyl acetate. The layers were separated and the aquoues layer extracted twice with ethyl acetate. The combined organic layers were washed with water and brine, dried with sodium sulfate and concentrated in vacuo. The obtained crude product (34 mg, quant.) was not further purified.

UPLC-MS (ESI+): [M+H]$^+$=461; R$_t$=1.49 min (Method E).

Example 2-29-1

2-[4-(trifluoromethoxy)benzyl]-1-[(cis)-3,3,5-trimethylcyclohexyl]-1H-benzimidazole-5-carboxylic Acid, Enantiomer A

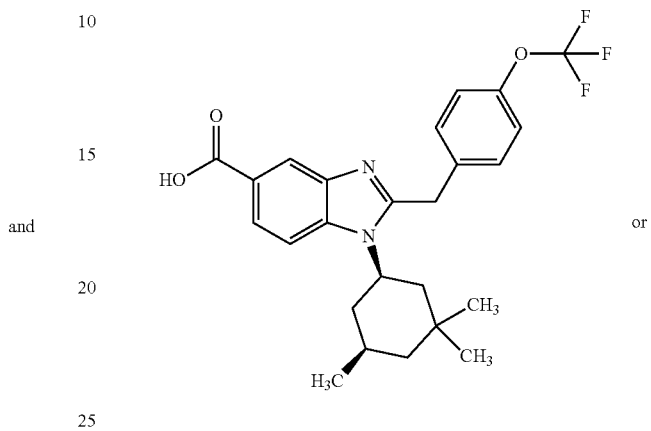

or

In analogy to example 2-29: Methyl 2-[4-(trifluoromethoxy)benzyl]-1-[(cis)-3,3,5-trimethylcyclohexyl]-1H-benzimidazole-5-carboxylate, enantiomer A (example 2-3-1; 48 mg, 0.10 mmol) was reacted with lithium hydroxide (5.0 eq., 12 mg, 0.51 mmol) in a mixture of THF/water (1:1, 2 mL) at 70° C. overnight to give the crude title compound (44 mg, 85%) which was not further purified.

$^1$H-NMR (300 MHz, DMSO-d$_6$): δ [ppm]=0.70 (s, 3H), 0.84-0.87 (m, 6H), 0.95-1.06 (m, 2H), 1.23-1.31 (m, 1H), 1.58-1.72 (m, 3H), 1.88 (t, 1H), 4.37-4.43 (m, 2H), 4.56 (d, 1H), 7.33 (s, 4H), 7.80 (s, 2H), 8.19 (s, 1H), 12.71 (br. s., 1H).

UPLC-MS (ESI+): [M+H]$^+$=461; R$_t$=1.49 min (Method E).

Example 2-29-2

2-[4-(trifluoromethoxy)benzyl]-1-[(cis)-3,3,5-trimethylcyclohexyl]-1H-benzimidazole-5-carboxylic Acid, Enantiomer B

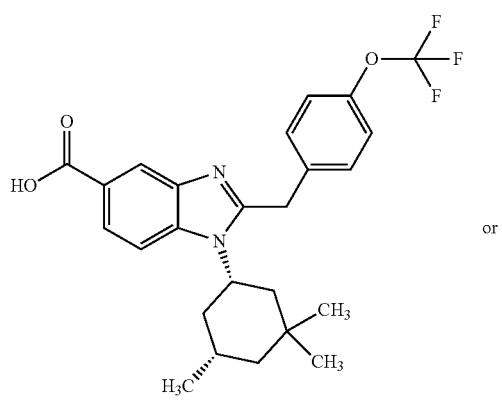

or

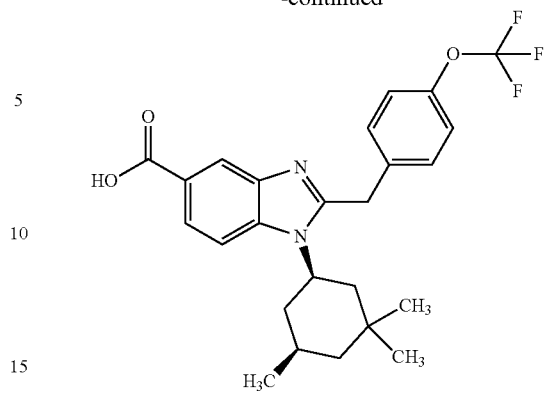

In analogy to example 2-29: Methyl 2-[4-(trifluoromethoxy)benzyl]-1-[(cis)-3,3,5-trimethylcyclohexyl]-1H-benzimidazole-5-carboxylate, enantiomer B (example 2-3-2; 51 mg, 0.11 mmol) was reacted with lithium hydroxide (5.0 eq., 13 mg, 0.54 mmol) in a mixture of THF/water (1:1, 2 mL) at 70° C. overnight to give the crude title compound (41 mg, 75%) which was not further purified.

$^1$H-NMR (300 MHz, DMSO-$d_6$): δ [ppm]=0.69 (s, 3H), 0.84-0.87 (m, 6H), 0.95-1.05 (m, 2H), 1.23-1.31 (m, 1H), 1.58-1.71 (m, 3H), 1.88 (t, 1H), 4.33-4.42 (m, 2H), 4.55 (d, 1H), 7.30-7.36 (m, 4H), 7.78 (s, 2H), 8.19 (s, 1H), 12.68 (br. s., 1H).

UPLC-MS (ESI+): [M+H]$^+$=461; $R_t$=1.49 min (Method E).

The examples in Table 4 were prepared in an analogous manner to example 2-29, starting from the given ester precursors.

TABLE 4

| Example | Structure/Name | Analytical data | Ester precursor |
|---|---|---|---|
| 2-30 | ![structure] and | UPLC-MS (ESI+): [M + H]$^+$ = 475; $R_t$ = 1.54/1.55 min (Method E). | Ref. Cpd. 2-4 |

TABLE 4-continued

| Example | Structure/Name | Analytical data | Ester precursor |
|---|---|---|---|
| | 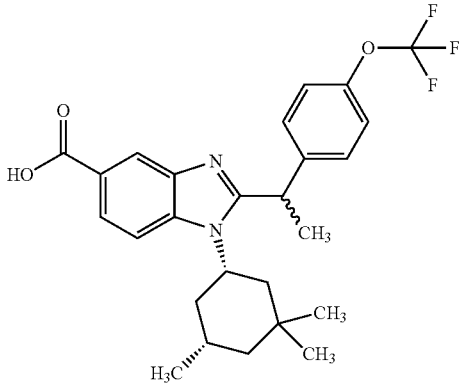<br>2-{1-[4-(trifluoromethoxy)phenyl]ethyl}-1-[(cis)-3,3,5-trimethylcyclohexyl]-1H-benzimidazole-5-carboxylic acid | | |
| 2-30-1 | 2-{1-[4-(trifluoromethoxy)phenyl]ethyl}-1-[(cis)-3,3,5-trimethylcyclohexyl]-1H-benzimidazole-5-carboxylic acid, diastereomer A | UPLC-MS (ESI+): $[M + H]^+ = 475$; $R_t = 0.92$ min (Method B). | Ref. Cpd. 2-4-1 |
| 2-30-2 | 2-{1-[4-(trifluoromethoxy)phenyl]ethyl}-1-[(cis)-3,3,5-trimethylcyclohexyl]-1H-benzimidazole-5-carboxylic acid, diastereomer B | UPLC-MS (ESI+): $[M + H]^+ = 475$; $R_t = 0.92$ min (Method B). | Ref. Cpd. 2-4-2 |
| 2-30-3 | 2-{1-[4-(trifluoromethoxy)phenyl]ethyl}-1-[(cis)-3,3,5-trimethylcyclohexyl]-1H-benzimidazole-5-carboxylic acid, diastereomer C | UPLC-MS (ESI+): $[M + H]^+ = 475$; $R_t = 0.92$ min (Method B). | Ref. Cpd. 2-4-3 |
| 2-30-4 | 2-{1-[4-(trifluoromethoxy)phenyl]ethyl}-1-[(cis)-3,3,5-trimethylcyclohexyl]-1H-benzimidazole-5-carboxylic acid, diastereomer D | UPLC-MS (ESI+): $[M + H]^+ = 475$; $R_t = 0.92$ min (Method B). | Ref. Cpd. 2-4-4 |
| 2-31 | 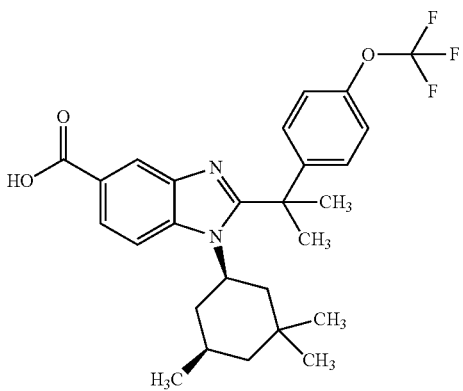<br>and | UPLC-MS (ESI−): $[M - H]^- = 487$; $R_t = 1.60$ min (Method E). | Ref. Cpd. 2-5 |

TABLE 4-continued
| Example | Structure/Name | Analytical data | Ester precursor |
|---|---|---|---|
| | 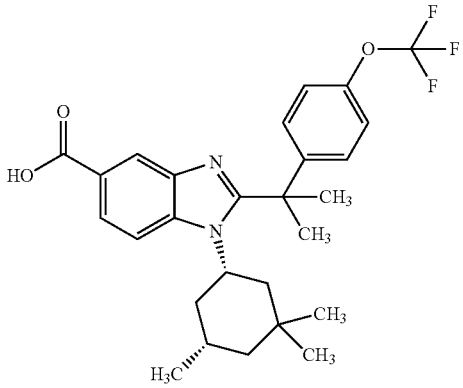 (±) 2-{2-[4-(trifluoromethoxy)phenyl]propan-2-yl}-1-[(cis)-3,3,5-trimethylcyclohexyl]-1H-benzimidazole-5-carboxylic acid | | |
| 2-32 | 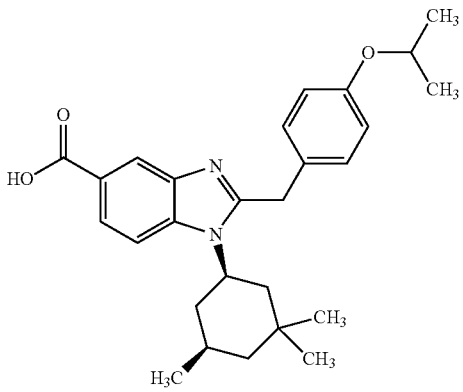 and 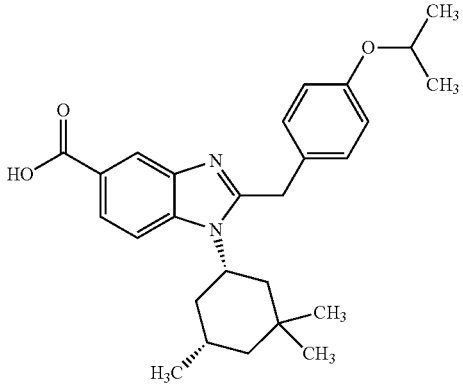 (±) 2-[4-(propan-2-yloxy)benzyl]-1-[(cis)-3,3,5-trimethylcyclohexyl]-1H-benzimidazole-5-carboxylic acid | UPLC-MS (ESI−): [M − H]⁻ = 433; $R_t$ = 1.43 min (Method E). | Example 2-6 |

TABLE 4-continued

| Example | Structure/Name | Analytical data | Ester precursor |
|---|---|---|---|
| 2-32-1 | 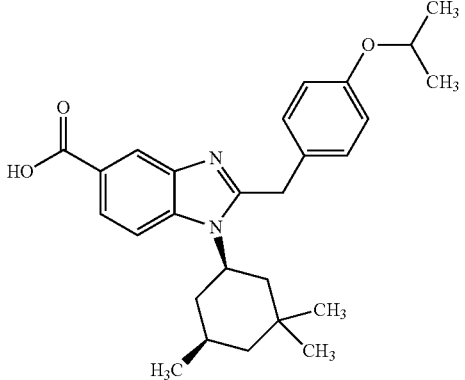<br>or<br>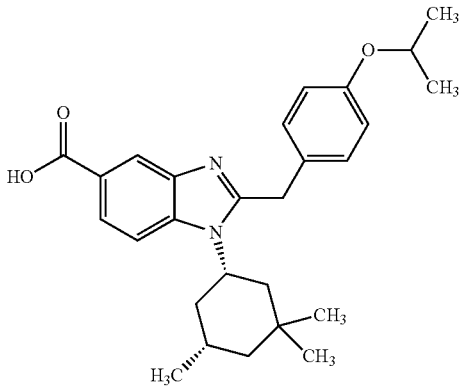<br>2-[4-(propan-2-yloxy)benzyl]-1-[(cis)-3,3,5-trimethylcyclohexyl]-1H-benzimidazole-5-carboxylic acid, enantiomer A | $^1$H-NMR (300 MHz, DMSO-d$_6$): δ [ppm] = 0.75 (s, 3H), 0.84-0.85 (m, 6H), 1.01-1.05 (m, 2H), 1.20-1.33 (m, 7H), 1.52 (br. s., 1H), 1.63-1.68 (m, 2H), 1.88 (t, 1H), 4.24 (d, 1H), 4.35-4.45 (m, 2H), 4.55 (sept, 1H), 6.84-6.87 (m, 2H), 7.07-7.10 (m, 2H), 7.73-7.79 (m, 2H), 8.17 (s, 1H), 12.65 (br. s., 1H).<br>UPLC-MS (ESI−): [M − H]$^-$ = 433; R$_t$ = 1.41 min (Method A). | Example. 2-6-1 |
| 2-32-2 | 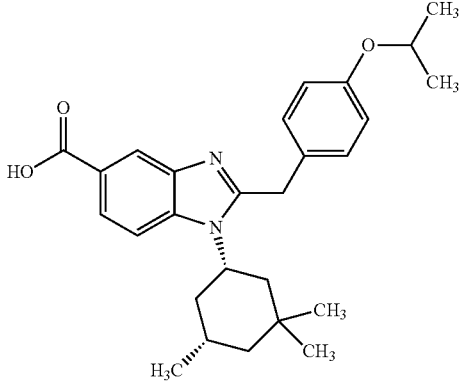<br>or | $^1$H-NMR (300 MHz, DMSO-d$_6$): δ [ppm] = 0.75 (s, 3H), 0.84-0.85 (m, 6H), 1.01-1.05 (m, 2H), 1.20-1.33 (m, 7H), 1.52 (br. s., 1H), 1.63-1.68 (m, 2H), 1.88 (t, 1H), 4.24 (d, 1H), 4.36-4.45 (m, 2H), 4.55 (sept, 1H), 6.84-6.87 (m, 2H), 7.07-7.10 (m, 2H), 7.73-7.79 (m, 2H), 8.17 (s, 1H), 12.66 (br. s., 1H).<br>UPLC-MS (ESI−): [M − H]$^-$ = 433; R$_t$ = 1.41 min (Method A). | Example 2-6-2 |

TABLE 4-continued

| Example | Structure/Name | Analytical data | Ester precursor |
|---|---|---|---|
| | 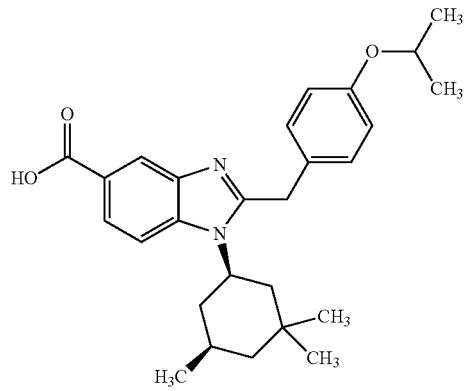2-[4-(propan-2-yloxy)benzyl]-1-[(cis)-3,3,5-trimethylcyclohexyl]-1H-benzimidazole-5-carboxylic acid, enantiomer B | | |
| 2-33 | 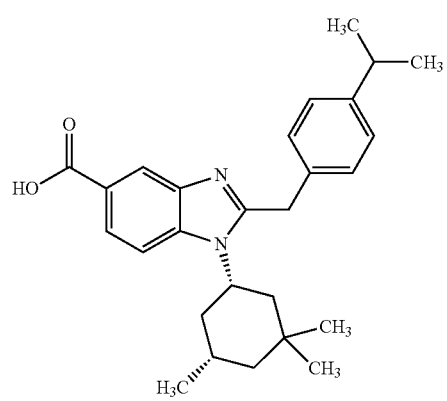and | $^1$H-NMR (400 MHz, DMSO-d$_6$): δ [ppm] = 0.68 (s, 3H), 0.83 (s, 6H), 0.95-1.02 (m, 2H), 1.16 (d, 6H), 1.25-1.28 (m, 1H), 1.46-1.49 (m, 1H), 1.60-1.65 (m, 2H), 1.85 (t, 1H), 2.84 (sept, 1H), 4.28-4.45 (m, 3H), 7.09-7.11 (m, 2H), 7.17-7.19 (m, 2H), 7.74-7.79 (m, 2H), 8.18 (s, 1H), 12.17 (br. s., 1H). UPLC-MS (ESI−): [M − H]$^-$ = 417; R$_t$ = 1.54 min (Method E). | Example 2-7 |

(±) 2-[4-(propan-2-yl)benzyl]-1-[(cis)-3,3,5-trimethylcyclohexyl]-1H-benzimidazole-5-carboxylic acid TABLE 4-continued
| Example | Structure/Name | Analytical data | Ester precursor |
|---|---|---|---|
| 2-34 | 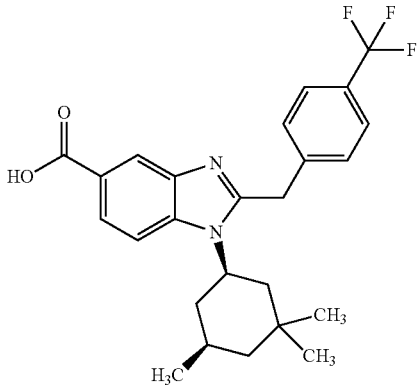<br><br>(±) 2-[4-(trifluoromethyl)benzyl]-1-[(cis)-3,3,5-trimethylcyclohexyl]-1H-benzimidazole-5-carboxylic acid | UPLC-MS (ESI−): [M − H]⁻ = 443; $R_t$ = 1.46 min (Method E). | Example 2-8 |
| 2-35 | 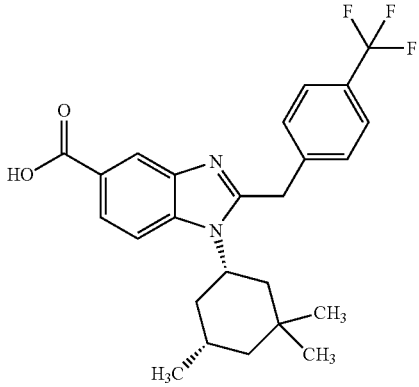<br><br>and | UPLC-MS (ESI−): [M − H]⁻ = 393; $R_t$ = 1.35 min (Method E). | Example 2-9 |

TABLE 4-continued
| Example | Structure/Name | Analytical data | Ester precursor |
|---|---|---|---|
| | 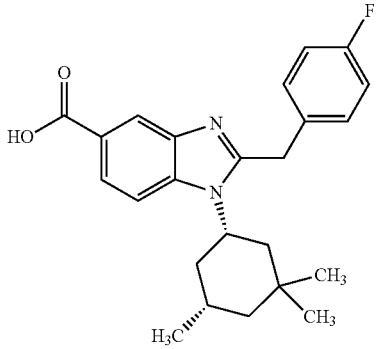<br>(±) 2-(4-fluorobenzyl)-1-[(cis)-3,3,5-trimethylcyclohexyl]-1H-benzimidazole-5-carboxylic acid | | |
| 2-36 | 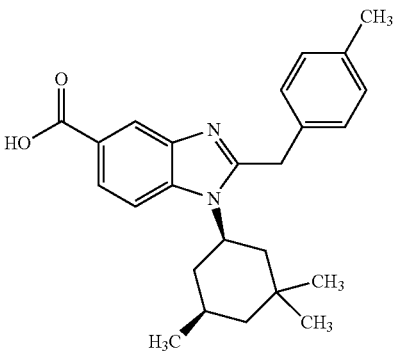<br>and<br>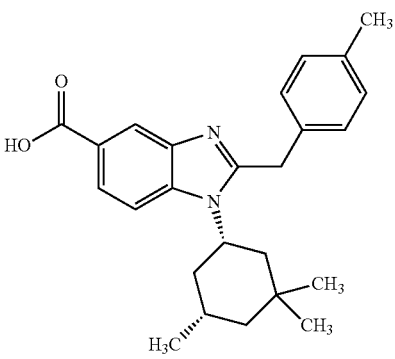<br>(±) 2-(4-methylbenzyl)-1-[(cis)-3,3,5-trimethylcyclohexyl]-1H-benzimidazole-5-carboxylic acid | UPLC-MS (ESI−):<br>[M − H]⁻ = 389;<br>$R_t$ = 1.40 min<br>(Method E). | Example 2-10 |

TABLE 4-continued
| Example | Structure/Name | Analytical data | Ester precursor |
|---|---|---|---|
| 2-37 | 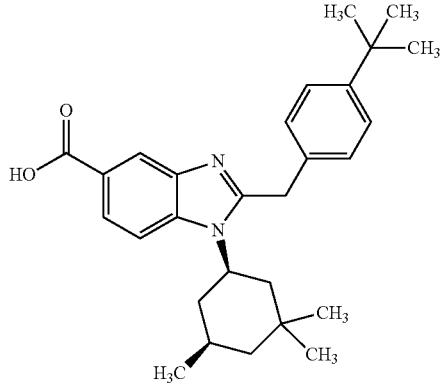<br><br>(±) 2-(4-tert-butylbenzyl)-1-[(cis)-3,3,5-trimethylcyclohexyl]-1H-benzimidazole-5-carboxylic acid | $^1$H-NMR (400 MHz, DMSO-d$_6$): δ [ppm] = 0.68 (s, 3H), 0.83 (s, 6H), 0.95-1.02 (m, 2H), 1.24-1.28 (m, 10H), 1.44-1.45 (m, 1H), 1.60-1.67 (m, 2H), 1.85 (t, 1H), 4.28-4.44 (m, 3H), 7.10-7.12 (m, 2H), 7.32-7.34 (m, 2H), 7.73-7.79 (m, 2H), 8.18 (d, 1H), 12.48 (br. s., 1H). UPLC-MS (ESI−): [M − H]$^−$ = 431; R$_t$ = 1.58 min (Method E). | Example 2-11 |
| 2-38 | 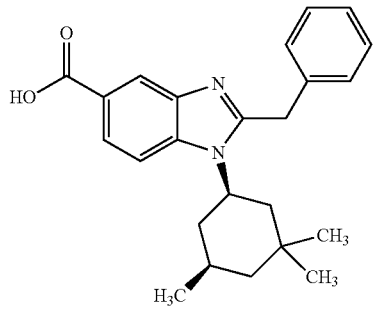<br>and | UPLC-MS (ESI+): [M + H]$^+$ = 377; R$_t$ = 1.34 min (Method E). | Example 2-12 |

TABLE 4-continued

| Example | Structure/Name | Analytical data | Ester precursor |
|---|---|---|---|
| | (±) 2-benzyl-1-[(cis)-3,3,5-trimethylcyclohexyl]-1H-benzimidazole-5-carboxylic acid | | |
| 2-39 | and<br>(±) 2-[2-(trifluoromethoxy)benzyl]-1-[(cis)-3,3,5-trimethylcyclohexyl]-1H-benzimidazole-5-carboxylic acid | UPLC-MS (ESI+):<br>[M + H]$^+$ = 461;<br>R$_t$ = 1.50 min<br>(Method E). | Example 2-13 |
| 2-40 | and | UPLC-MS (ESI+):<br>[M + H]$^+$ = 461;<br>R$_t$ = 1.48 min<br>(Method E). | Example 2-14 |

TABLE 4-continued
| Example | Structure/Name | Analytical data | Ester precursor |
|---|---|---|---|
| | 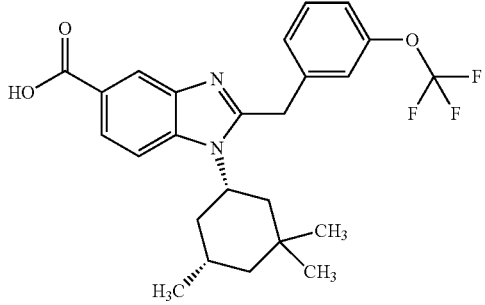<br>(±) 2-[3-(trifluoromethoxy)benzyl]-1-[(cis)-3,3,5-trimethylcyclohexyl]-1H-benzimidazole-5-carboxylic acid | | |
| 2-41 | 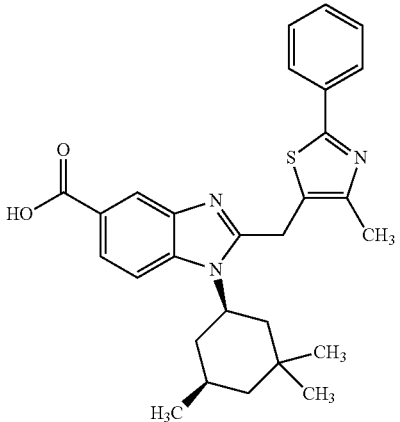<br>and<br>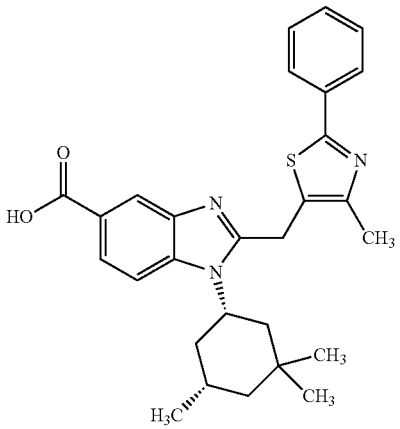<br>(±) 2-[(4-methyl-2-phenyl-1,3-thiazol-5-yl)methyl]-1-[(cis)-3,3,5-trimethylcyclohexyl]-1H-benzimidazole-5-carboxylic acid | UPLC-MS (ESI+): [M + H]$^+$ = 474; R$_t$ = 1.47 min (Method E). | Example 2-15 |

TABLE 4-continued

| Example | Structure/Name | Analytical data | Ester precursor |
|---|---|---|---|
| 2-42 | 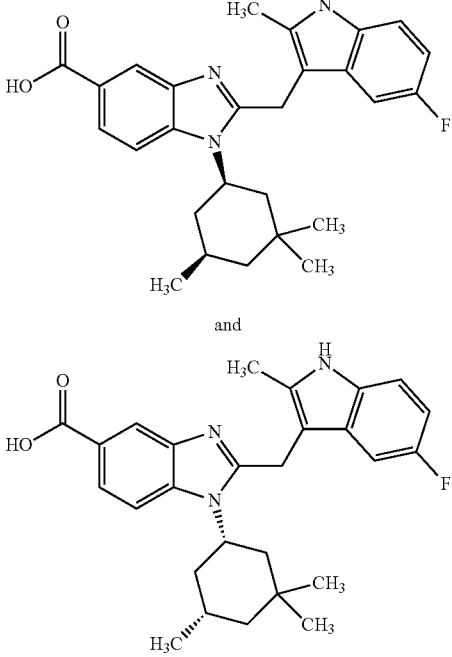<br>and<br><br>(±) 2-[(5-fluoro-2-methyl-1H-indol-3-yl)methyl]-1-[(cis)-3,3,5-trimethylcyclohexyl]-1H-benzimidazole-5-carboxylic acid | UPLC-MS (ESI+): [M + H]$^+$ = 448; R$_t$ = 1.27 min (Method E). | Example 2-16 |
| 2-43 | 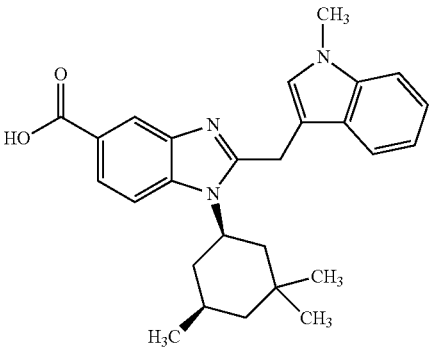<br>and<br>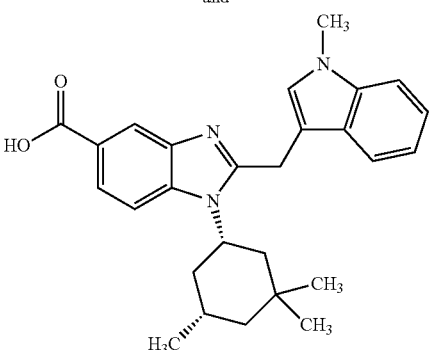<br>(±) 2-[(1-methyl-1H-indol-3-yl)methyl]-1-[(cis)-3,3,5-trimethylcyclohexyl]-1H-benzimidazole-5-carboxylic acid | UPLC-MS (ESI+): [M + H]$^+$ = 430; R$_t$ = 1.32 min (Method E). | Example 2-17 |

TABLE 4-continued

| Example | Structure/Name | Analytical data | Ester precursor |
|---|---|---|---|
| 2-44 | 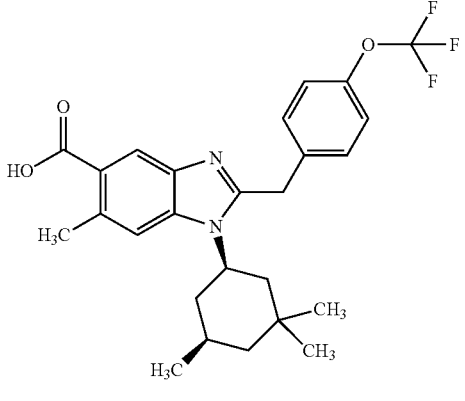<br><br>and<br><br>(±) 6-methyl-2-[4-(trifluoromethoxy)benzyl]-1-[(cis)-3,3,5-trimethylcyclohexyl]-1H-benzimidazole-5-carboxylic acid | $^1$H-NMR (400 MHz, DMSO-d$_6$): δ [ppm] = 0.69 (s, 3H), 0.86-0.89 (m, 6H), 0.99-1.01 (m, 1H), 1.09-1.19 (m, 1H), 1.23-1.30 (m, 1H), 1.68-1.78 (m, 3H), 1.94 (t, 1H), 2.70 (s, 3H), 4.45-4.50 (m, 1H), 4.61 (d, 1H), 4.79 (d, 1H), 7.37-7.39 (m, 2H), 7.43-7.45 (m, 2H), 7.91 (s, 1H), 8.20 (s, 1H), 13.03 (br. s., 1H).<br>UPLC-MS (ESI+): [M + H]$^+$ = 475; R$_t$ = 0.94 min (Method F). | Example 2-18 |
| 2-44-1 | 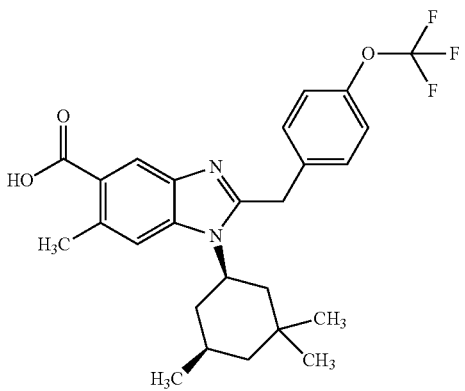<br><br>or | $^1$H-NMR (400 MHz, DMSO-d$_6$): δ [ppm] = 0.69 (s, 3H), 0.84-0.87 (m, 6H), 0.93-0.96 (m, 1H), 1.01-1.07 (m, 1H), 1.26-1.29 (m, 1H), 1.53-1.55 (m, 1H), 1.67-1.71 (m, 2H), 1.89 (t, 1H), 2.65 (s, 3H), 4.28-4.38 (m, 2H), 4.51 (d, 1H), 7.32 (s, 4H), 7.56 (s, 1H), 8.11 (s, 1H), 12.50 (br. s., 1H).<br>UPLC-MS (ESI+): [M + H]$^+$ = 475; R$_t$ = 0.93 min (Method F). | Example 2-18-1 |

TABLE 4-continued

| Example | Structure/Name | Analytical data | Ester precursor |
|---|---|---|---|
| | 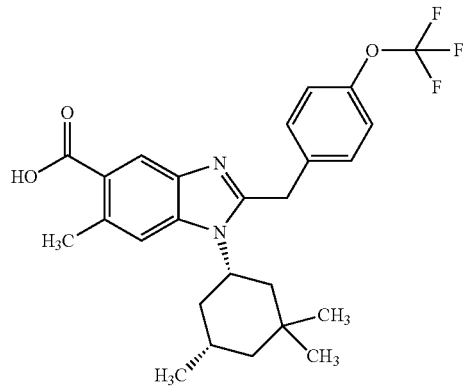 6-methyl-2-[4-(trifluoromethoxy)benzyl]-1-[(cis)-3,3,5-trimethylcyclohexyl]-1H-benzimidazole-5-carboxylic acid, enantiomer A | | |
| 2-44-2 | 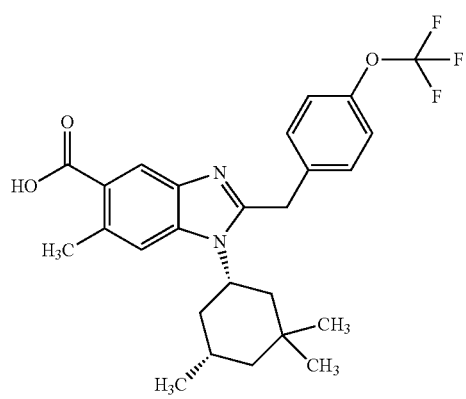 or 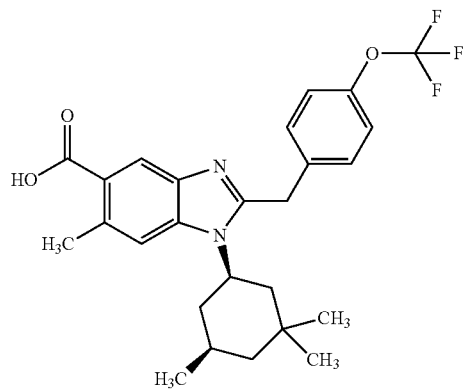 6-methyl-2-[4-(trifluoromethoxy)benzyl]-1-[(cis)-3,3,5-trimethylcyclohexyl]-1H-benzimidazole-5-carboxylic acid, enantiomer B | $^1$H-NMR (400 MHz, DMSO-$d_6$): δ [ppm] = 0.69 (s, 3H), 0.84-0.87 (m, 6H), 0.93-0.96 (m, 1H), 1.01-1.07 (m, 1H), 1.26-1.29 (m, 1H), 1.53-1.55 (m, 1H), 1.67-1.71 (m, 2H), 1.89 (t, 1H), 2.65 (s, 3H), 4.27-4.38 (m, 2H), 4.51 (d, 1H), 7.32 (s, 4H), 7.56 (s, 1H), 8.11 (s, 1H), 12.50 (br. s., 1H). UPLC-MS (ESI+): [M + H]$^+$ = 475; R$_t$ = 0.94 min (Method F). | Example 2-18-2 |

TABLE 4-continued

| Example | Structure/Name | Analytical data | Ester precursor |
|---|---|---|---|
| 2-45 | 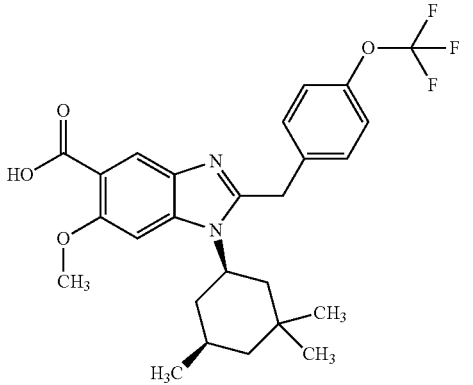  and  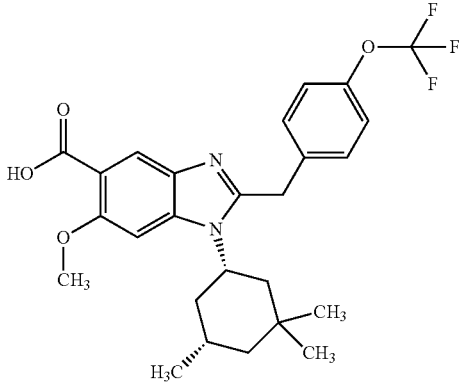  (±) 6-methoxy-2-[4-(trifluoromethoxy)benzyl]-1-[(cis)-3,3,5-trimethylcyclohexyl]-1H-benzimidazole-5-carboxylic acid  or | $^1$H-NMR (400 MHz, DMSO-$d_6$): δ [ppm] = 0.70 (s, 3H), 0.86-0.89 (m, 6H), 1.00-1.09 (m, 2H), 1.27-1.30 (m, 1H), 1.65-1.72 (m, 3H), 1.88 (t, 1H), 3.91 (s, 3H), 4.39-4.51 (m, 2H), 4.66 (d, 1H), 7.23 (s, 1H), 7.34-7.40 (m, 4H), 7.98 (s, 1H), 12.67 (br. s., 1H). UPLC-MS (ESI+): [M + H]$^+$ = 491; R$_t$ = 1.47 min (Method E). | Example 2-19 |
| 2-45-1 | 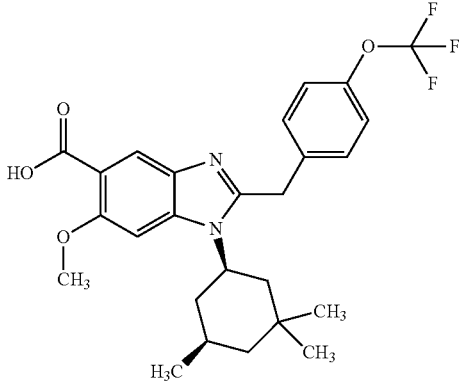 | $^1$H-NMR (400 MHz, DMSO-$d_6$): δ [ppm] = 0.70 (s, 3H), 0.85-0.87 (m, 6H), 0.93-1.04 (m, 2H), 1.26-1.30 (m, 1H), 1.55 (br. s., 1H), 1.61-1.71 (m, 2H), 1.85 (t, 1H), 3.87 (s, 3H), 4.28-4.35 (m, 2H), 4.49 (d, 1H), 7.11 (s, 1H), 7.32 (s, 4H), 7.91 (s, 1H), 12.36 (br. s., 1H). UPLC-MS (ESI+): [M + H]$^+$ = 491; R$_t$ = 0.92 min (Method F). | Example 2-19-1 |

TABLE 4-continued

| Example | Structure/Name | Analytical data | Ester precursor |
|---|---|---|---|
| | 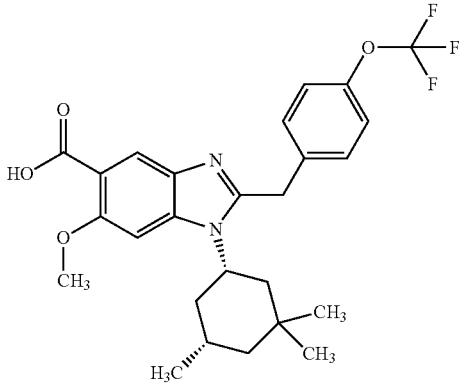<br>6-methoxy-2-[4-(trifluoromethoxy)benzyl]-1-[(cis)-3,3,5-trimethylcyclohexyl]-1H-benzimidazole-5-carboxylic acid, enantiomer A | | |
| 2-45-2 | 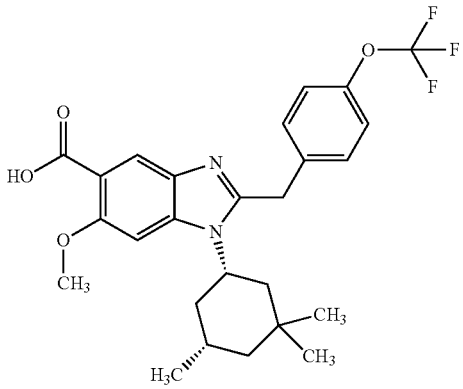<br>or<br>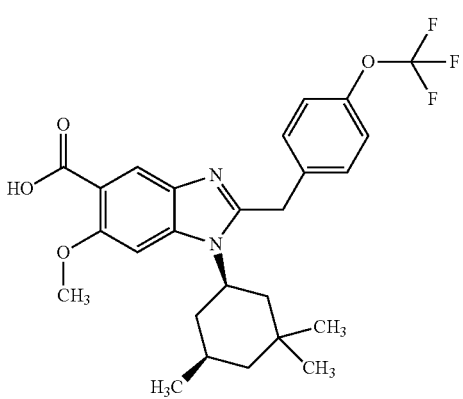<br>6-methoxy-2-[4-(trifluoromethoxy)benzyl]-1-[(cis)-3,3,5-trimethylcyclohexyl]-1H-benzimidazole-5-carboxylic acid, enantiomer b | $^1$H-NMR (400 MHz, DMSO-$d_6$): δ [ppm] = 0.70 (s, 3H), 0.86-0.88 (m, 6H), 0.97-1.06 (m, 2H), 1.27-1.30 (m, 1H), 1.60-1.70 (m, 3H), 1.86 (t, 1H), 3.89 (s, 3H), 4.34-4.43 (m, 2H), 4.57 (d, 1H), 7.17 (s, 1H), 7.34 (s, 4H), 7.94 (s, 1H), 12.50 (br. s., 1H).<br>UPLC-MS (ESI+): [M + H]$^+$ = 491; $R_t$ = 0.92 min (Method F). | Example 2-19-2 |

TABLE 4-continued
| Example | Structure/Name | Analytical data | Ester precursor |
|---|---|---|---|
| 2-46 | 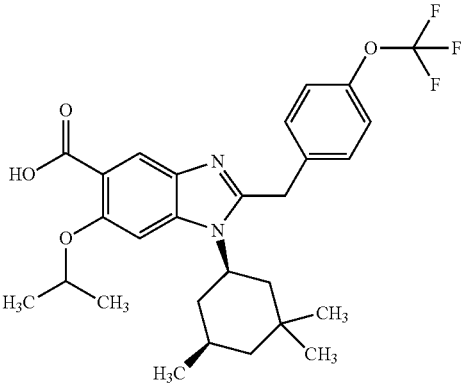 and 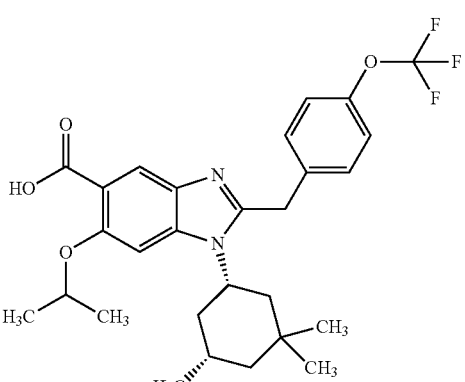 (±) 6-(propan-2-yloxy)-2-[4-(trifluoromethoxy)benzyl]-1-[(cis)-3,3,5-trimethylcyclohexyl]-1H-benzimidazole-5-carboxylic acid | UPLC-MS (ESI+): [M + H]$^+$ = 519; R$_t$ = 0.93 min (Method D). | Example 2-20 |
| 2-46-1 | 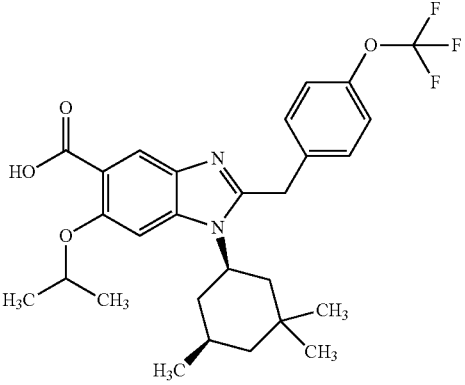 or | UPLC-MS (ESI+): [M + H]$^+$ = 519; R$_t$ = 0.97 min (Method F). | Example 2-20-1 |

TABLE 4-continued
| Example | Structure/Name | Analytical data | Ester precursor |
|---|---|---|---|
| | 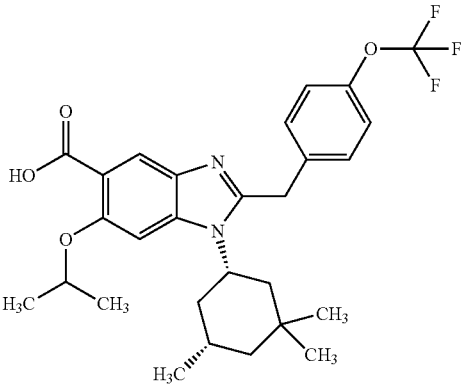6-(propan-2-yloxy)-2-[4-(trifluoromethoxy)benzyl]-1-[(cis)-3,3,5-trimethylcyclohexyl]-1H-benzimidazole-5-carboxylic acid, enantiomer A | | |
| 2-46-2 | 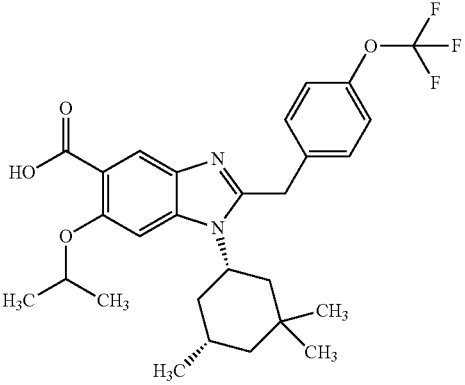or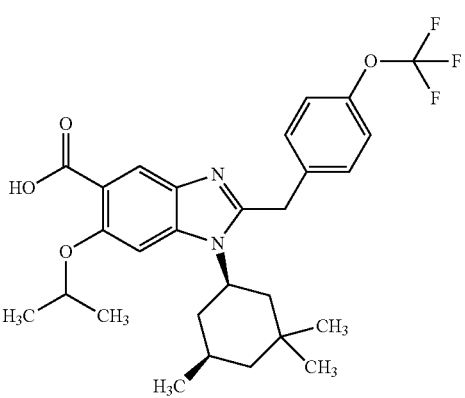6-(propan-2-yloxy)-2-[4-(trifluoromethoxy)benzyl]-1-[(cis)-3,3,5-trimethylcyclohexyl]-1H-benzimidazole-5-carboxylic acid, enantiomer B | UPLC-MS (ESI+): [M + H]$^+$ = 519; R$_t$ = 0.97 min (Method F). | Example 2-20-2 |

TABLE 4-continued
| Example | Structure/Name | Analytical data | Ester precursor |
|---|---|---|---|
| 2-47 | 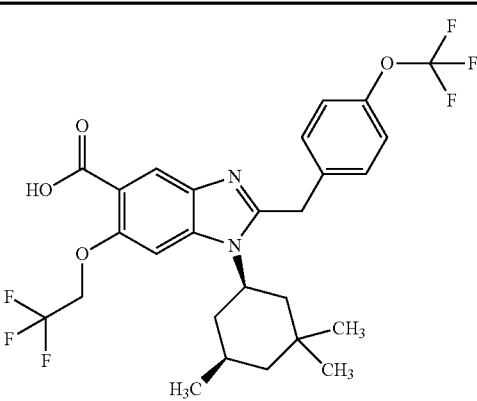 and 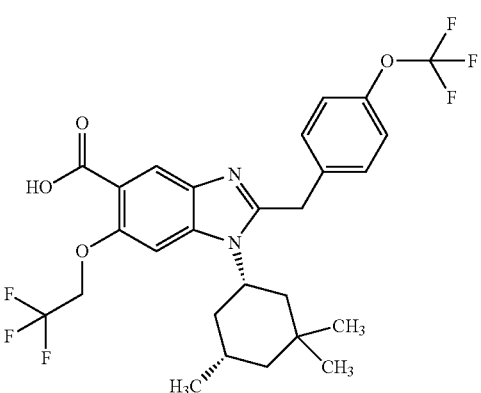<br>(±) 6-(2,2,2-trifluoroethoxy)-2-[4-(trifluoromethoxy)benzyl]-1-[(cis)-3,3,5-trimethylcyclohexyl]-1H-benzimidazole-5-carboxylic acid | UPLC-MS (ESI+): [M + H]$^+$ = 559; R$_t$ = 0.99 min (Method F). | Example 2-21 |
| 2-47-1 | 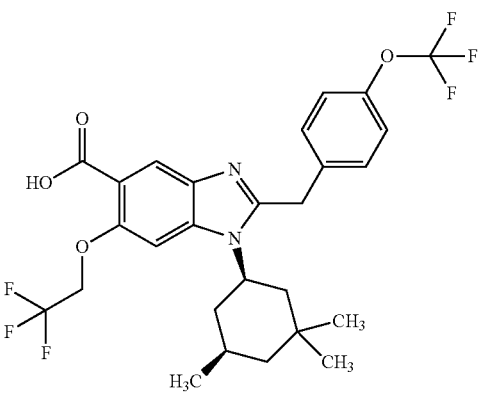<br>or | UPLC-MS (ESI+): [M + H]$^+$ = 559; R$_t$ = 0.98 min (Method F). | Example 2-21-1 |

TABLE 4-continued

| Example | Structure/Name | Analytical data | Ester precursor |
|---|---|---|---|
| | 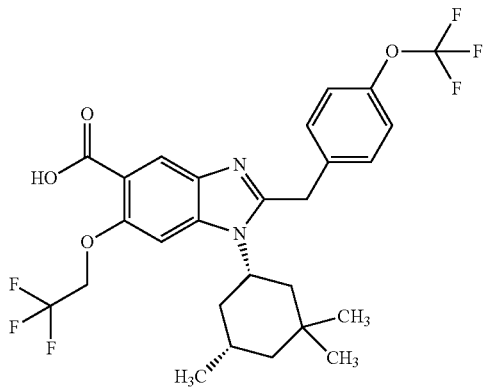
6-(2,2,2-trifluoroethoxy)-2-[4-(trifluoromethoxy)benzyl]-1-[(cis)-3,3,5-trimethylcyclohexyl]-1H-benzimidazole-5-carboxylic acid, enantiomer A | | |
| 2-47-2 | 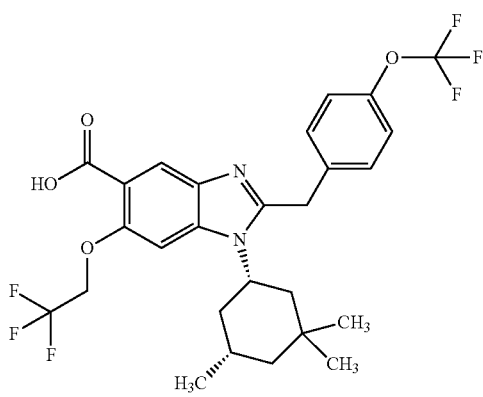
or
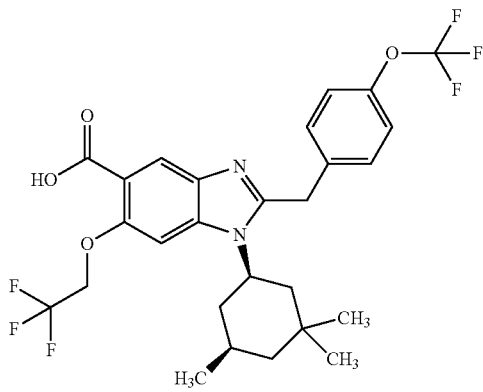
6-(2,2,2-trifluoroethoxy)-2-[4-(trifluoromethoxy)benzyl]-1-[(cis)-3,3,5-trimethylcyclohexyl]-1H-benzimidazole-5-carboxylic acid, enantiomer B | UPLC-MS (ESI+): $[M + H]^+ = 559$; $R_t = 0.96$ min (Method F). | Example 2-21-2 |

TABLE 4-continued

| Example | Structure/Name | Analytical data | Ester precursor |
|---|---|---|---|
| 2-48 | 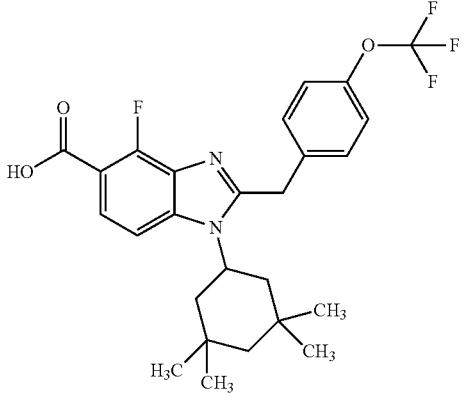<br>4-fluoro-1-(3,3,5,5-tetramethylcyclohexyl)-2-[4-(trifluoromethoxy)benzyl]-1H-benzimidazole-5-carboxylic acid | $^1$H-NMR (400 MHz, DMSO-d$_6$): δ [ppm] = 0.77 (s, 6H), 0.86 (s, 6H), 1.14-1.17 (m, 1H), 1.24-1.28 (m, 3H), 1.94 (t, 2H), 4.24-4.32 (m, 1H), 4.46 (s, 2H), 7.29-7.35 (m, 4H), 7.63-7.68 (m, 2H), 13.00 (br. s., 1H). UPLC-MS (ESI+): [M + H]$^+$ = 493; R$_t$ = 1.56 min (Method E). | Example 2-22 |
| 2-49 | 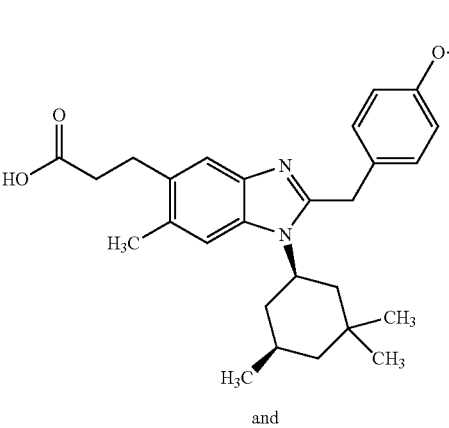<br>and<br>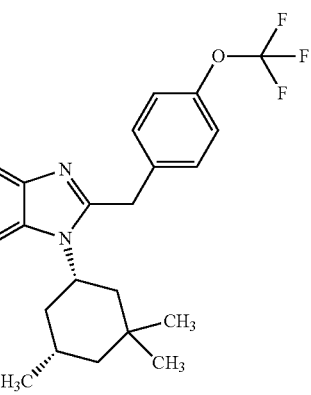<br>(±) 3-{6-methyl-2-[4-(trifluoromethoxy)benzyl]-1-[(cis)-3,3,5-trimethylcyclohexyl]-1H-benzimidazol-5-yl}propanoic acid | $^1$H-NMR (400 MHz, DMSO-d$_6$): δ [ppm] = 0.69 (s, 3H), 0.84-0.87 (m, 6H), 0.92-0.95 (m, 1H), 1.01-1.07 (m, 1H), 1.23-1.30 (m, 1H), 1.54-1.56 (m, 1H), 1.67-1.72 (m, 2H), 1.89 (t, 1H), 2.40 (s, 3H), 2.54-2.56 (m, 2H), 2.87-2.91 (m, 2H), 4.30-4.39 (m, 2H), 4.53 (d, 1H), 7.33 (s, 4H), 7.42 (s, 1H), 7.54 (s, 1H), 12.16 (br. s., 1H). UPLC-MS (ESI+): [M + H]$^+$ = 503; R$_t$ = 1.00 min (Method D). | Example 2-27 |

TABLE 4-continued

| Example | Structure/Name | Analytical data | Ester precursor |
|---|---|---|---|
| 2-50 | 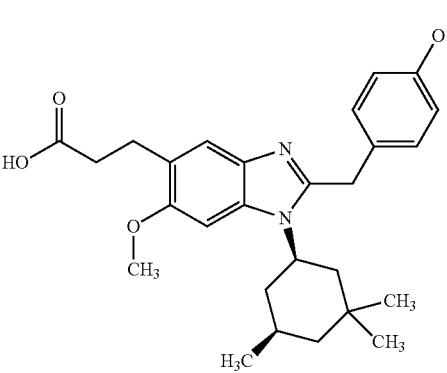<br>and<br>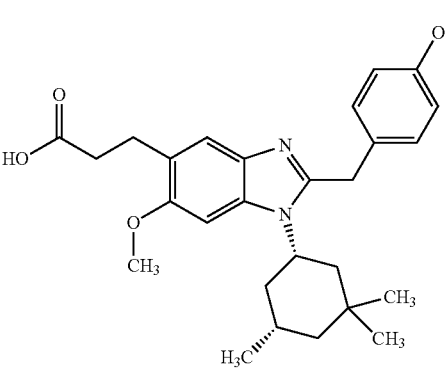<br>(±) 3-{6-methoxy-2-[4-(trifluoromethoxy)benzyl]-1-[(cis)-3,3,5-trimethylcyclohexyl]-1H-benzimidazol-5-yl}propanoic acid | $^1$H-NMR (400 MHz, DMSO-$d_6$): δ [ppm] = 0.71 (s, 3H), 0.87-0.90 (m, 6H), 1.04-1.12 (m, 2H), 1.28-1.31 (m, 1H), 1.72-1.77 (m, 3H), 1.91 (t, 1H), 2.54-2.55 (m, 2H), 2.90-2.94 (m, 2H), 3.94 (s, 3H), 4.47-4.60 (m, 2H), 4.78 (d, 1H), 7.21 (s, 1H), 7.38-7.44 (m, 4H), 7.59 (s, 1H), 12.17 (br. s., 1H).<br>UPLC-MS (ESI+): [M + H]$^+$ = 519; $R_t$ = 1.00 min (Method F). | Example 2-28 |
| 2-50-1 | 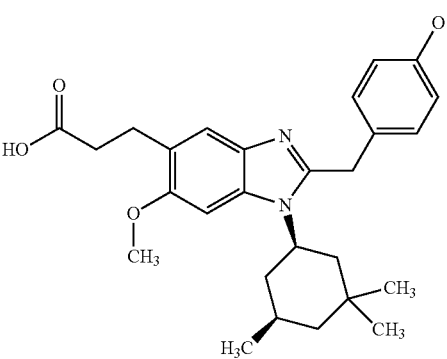<br>or | $^1$H-NMR (400 MHz, DMSO-$d_6$): δ [ppm] = 0.71 (s, 3H), 0.87-0.90 (m, 6H), 1.05-1.11 (m, 2H), 1.28-1.32 (m, 1H), 1.72-1.76 (m, 3H), 1.91 (t, 1H), 2.54-2.55 (m, 2H), 2.90-2.94 (m, 2H), 3.94 (s, 3H), 4.47-4.52 (m, 1H), 4.58 (d, 1H), 4.77 (d, 1H), 7.20 (s, 1H), 7.37-7.44 (m, 4H), 7.58 (s, 1H), 12.16 (br. s., 1H).<br>UPLC-MS (ESI+): [M + H]+ = 519; $R_t$ = 0.95 min (Method F). | Example 2-28-1 |

TABLE 4-continued

| Example | Structure/Name | Analytical data | Ester precursor |
|---|---|---|---|
| | 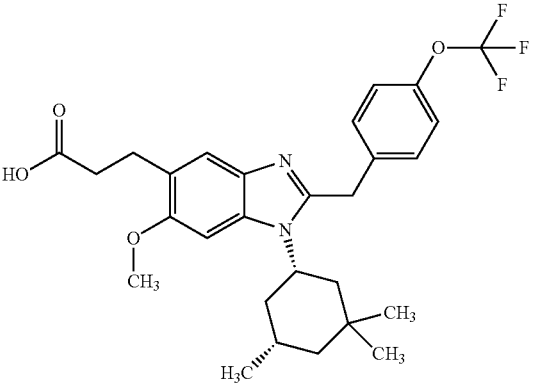<br>3-{6-methoxy-2-[4-(trifluoromethoxy)benzyl]-1-[(cis)-3,3,5-trimethylcyclohexyl]-1H-benzimidazol-5-yl}propanoic acid, enantiomer A | | |
| 2-50-2 | 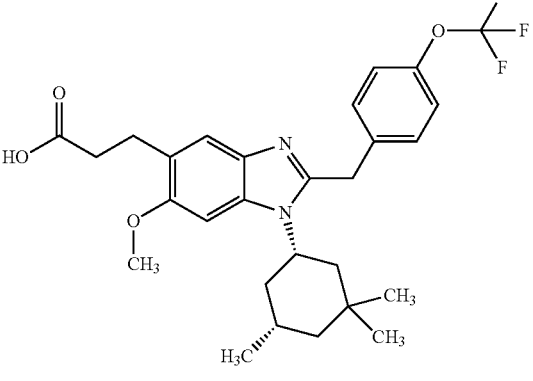<br>or<br>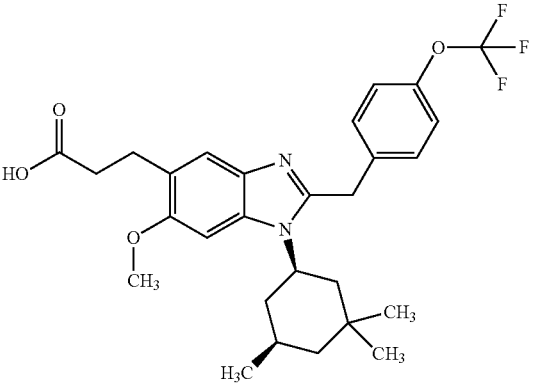<br>3-{6-methoxy-2-[4-(trifluoromethoxy)benzyl]-1-[(cis)-3,3,5-trimethylcyclohexyl]-1H-benzimidazol-5-yl}propanoic acid, enantiomer B | $^1$H-NMR (400 MHz, DMSO-$d_6$): δ [ppm] = 0.71 (s, 3H), 0.87-0.90 (m, 6H), 1.03-1.12 (m, 2H), 1.28-1.31 (m, 1H), 1.72-1.76 (m, 3H), 1.91 (t, 1H), 2.52-2.55 (m, 2H), 2.90-2.94 (m, 2H), 3.94 (s, 3H), 4.47-4.53 (m, 1H), 4.61 (d, 1H), 4.80 (d, 1H), 7.21 (s, 1H), 7.37-7.45 (m, 4H), 7.59 (s, 1H), 12.17 (br. s., 1H).<br>UPLC-MS (ESI+): [M + H]$^+$ = 519; R$_t$ = 0.95 min (Method F). | Example 2-28-2 |

Example 2-51 methyl 3-{4-fluoro-1-(3,3,5,5-tetramethylcyclohexyl)-2-[4-(trifluoromethoxy)benzyl]-1H-benzimidazol-5-yl}propanoate

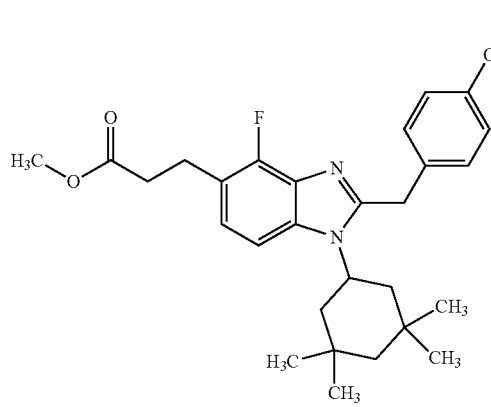

A solution of 4-trifluoromethoxyphenylacetic acid (CAS-No. [4315-07-5]; 1.00 eq., 126 mg, 0.571 mmol) in tetrahydrofuran (13 mL) was treated with 1,1'-carbonyl-diimidazole (1.0 eq., 93 mg, 0.57 mmol) at rt and subsequently heated at 75° C. for 1 h. A solution of methyl 3-{3-amino-2-fluoro-4-[(3,3,5,5-tetramethylcyclohexyl)amino]phenyl}propanoate (intermediate 1-10; 1.00 eq., 200 mg, 0.571 mmol) in tetrahydrofuran (3 mL) was added and the reaction was heated at 75° C. for 18 h. The volatiles were removed and the deep red residue taken up in acetic acid (6 mL) and heated at 110° C. for 2 h. The reaction mixture was diluted with ethyl acetate (20 mL) and washed with aqueous 2 M sodium hydroxide solution until the washings were basic. The organic layer was dried with solid sodium sulfate and concentrated under vacuum. The crude material was purified by flash chromatography (SiO$_2$-heptane/ethyl acetate) to give the title compound (159 mg, 52%) as a brown gum.

$^1$H-NMR (300 MHz, CDCl$_3$): δ [ppm]=0.77 (s, 6H), 0.88 (s, 6H), 1.10-1.31 (m, 4H), 1.86 (t, 2H), 2.69 (t, 2H), 3.09 (t, 2H), 3.68 (s, 3H), 4.23-4.28 (m, 1H), 4.36 (s, 2H), 7.02 (t, 1H), 7.15-7.25 (m, 5H).

UPLC-MS (ESI+): [M+H]$^+$=535; R$_t$=1.12 min (Method G).

Example 2-52

3-{4-fluoro-1-(3,3,5,5-tetramethylcyclohexyl)-2-[4-(trifluoromethoxy)benzyl]-1H-benzimidazol-5-yl}Propanoic Acid

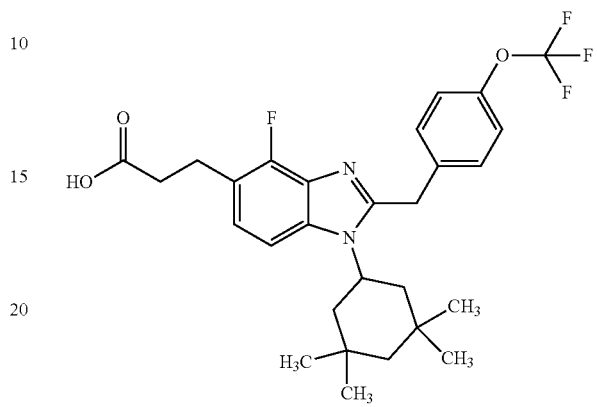

A solution of methyl 3-{4-fluoro-1-(3,3,5,5-tetramethylcyclohexyl)-2-[4-(trifluoromethoxy)benzyl]-1H-benzimidazol-5-yl}propanoate (example 2-51; 159 mg, 0.297 mmol) in tetrahydrofuran (30 mL) and water (7.5 mL) was treated with lithium hydroxide monohydrate (4.0 eq., 50 mg, 1.2 mmol) and the reaction was stirred at rt for 66 h. Saturated ammonium chloride solution was added (to pH 5) and the mixture extracted with ethyl acetate (3×30 mL). The combined organic layers were dried with solid sodium sulfate and concentrated under vacuum. Purification by trituration (diethyl ether) gave the title compound (132 mg, 85%) as a pale peach solid.

$^1$H-NMR (300 MHz, CDCl$_3$): δ [ppm]=0.77 (s, 6H), 0.88 (s, 6H), 1.10-1.30 (m, 4H), 1.88 (t, 2H), 2.76 (t, 2H), 3.13 (t, 2H), 4.24-4.28 (m, 1H), 4.39 (s, 2H), 7.00-7.20 (m, 6H).

UPLC-MS (ESI+): [M+H]$^+$=521; R$_t$=2.30 min (Method H).

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient.

Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents. Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349 ; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CC_2F_2$, $F_2ClC\text{-}CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 min.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. antihyper-proliferative or other indication agents, and the like, as well as with admixtures and combinations thereof. Other indication agents include, but are not limited to, anti-angiogenic agents, mitotic inhibitors, alkylating agents, antimetabolites, DNA-intercalating antibiotics, growth factor inhibitors, cell cycle inhibitors, enzyme inhibitors, toposisomerase inhibitors, biological response modifiers, or antihormones.

Examples of chemotherapeutic agents and anti-cancer agents include: 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate,amrubicin, amsacrine, anastrozole, ancestim, anethole dithiolethione, angiolabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin +estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone +pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

A compound of general formula (I) as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, MK-2206, novolimus, OSI-027, perifosine, PF-04691502, PF-05212384, PX-866, rapamycin, RG-7167, RO-4987655, RO-5126766, selumetinib, TAK-733, trametinib, triciribine, UCN-01, WX-554, XL-147, XL-765, zotarolimus, ZSTK-474.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit mutated isocitratdehydrogenase 1 (mIDH1 R132H) and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses are affected by inhibition of mutated isocitratdehydrogenase 1 (mIDH1 R132H), such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyperproliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, anaplastic astrocytoma, diffuse astrocytoma, glioblastoma, oligodendroglioma, secondary glioblastoma multiforme as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth. Methods of testing for a particular pharmacological or pharmaceutical property are well known to persons skilled in the art.

The example testing experiments described herein serve to illustrate the present invention and the invention is not limited to the examples given.

Biological Assays:

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Mutant IDH1 R132H Biochemical Assay mIDH1 catalyzes the NADPH-dependent reduction of alpha-ketoglutarate (α-KG) to (2R)-2-hydroxyglutarate (2-HG). NADPH consumption was measured by luminescent readout.

The biochemical reactions were performed at 32° C. in 384-well plates using a reaction volume of 41 μL and the following assay buffer conditions: 50 mM Tris pH 7.5, 100 mM NaCl, 20 mM $MgCl_2$, 0.05% BSA, 0.01% Brij, 1 μM NADPH, and 250 μM α-KG. The IDH1 R132H enzyme was used in a final concentration of 1.5 nM. Test compounds were used in a concentration range between 0.002 and 10 μM. The final DMSO concentration was 2.4%.

The reaction was incubated for 30 minutes, then 40 μL of detection mix (0.75 μg/mL Luciferase, 0.02 U/mL Oxidoreductase, 4 μg/mL FMN, 2 μL/mL decanal/ethanol, 50 mM Tris pH 7.5, 0.5% Glycerin, 0.01% Tween-20, 0.05% BSA) was added. Luminescence was measured on a luminescent reader (10 seconds measuring time, 1 second integration period, 30% sensitivity). The decrease in luminescence is proportional to mIDH1 activity. $IC_{50}$ values are determined by interpolation from plots of relative luminescence versus inhibitor concentration.

TABLE 5

$IC_{50}$ values of selected examples in mutant IDH1 R132H biochemical assay

| Example | Mutant IDH1 R132H $IC_{50}$ [μM] |
| --- | --- |
| 2-1 | 9.9 |
| 2-1-1 | 1.0 |
| 2-1-2 | 5.7 |
| 2-2 | 0.19 |
| 2-2-1 | 0.13 |
| 2-2-2 | 0.39 |
| 2-3 | 0.67 |
| 2-3-1 | 1.7 |
| 2-3-2 | 0.61 |
| 2-6 | 1.5 |
| 2-6-1 | n.d. |
| 2-6-2 | n.d. |
| 2-7 | 0.33 |
| 2-8 | 1.5 |
| 2-9 | 4.2 |
| 2-10 | 1.5 |
| 2-11 | 1.4 |
| 2-12 | 3.5 |
| 2-13 | 10 |
| 2-14 | 10 |
| 2-15 | 8.0 |
| 2-16 | 5.8 |
| 2-17 | 9.0 |
| 2-18 | 0.15 |
| 2-18-1 | 0.14 |
| 2-18-2 | 1.2 |
| 2-19 | 0.16 |
| 2-19-1 | 1.0 |
| 2-19-2 | 0.07 |
| 2-20 | 2.8 |
| 2-20-1 | 1.3 |
| 2-20-2 | 3.3 |
| 2-21 | >10 |
| 2-21-1 | 5.0 |
| 2-21-2 | 12 |
| 2-22 | 0.80 |
| 2-23 | 0.75 |
| 2-24 | 1.5 |
| 2-25 | 0.35 |
| 2-26 | 0.70 |
| 2-27 | 0.18 |
| 2-28 | 0.18 |
| 2-28-1 | 1.2 |
| 2-28-2 | 0.10 |
| 2-29 | 0.10 |
| 2-29-1 | 0.14 |
| 2-29-2 | 0.05 |
| 2-30 | 2.7 |
| 2-30-1 | 5.0 |
| 2-30-2 | 0.95 |
| 2-30-3 | 2.0 |
| 2-30-4 | >10 |
| 2-31 | 3.8 |
| 2-32 | 0.25 |
| 2-32-1 | 0.45 |
| 2-32-2 | 0.30 |
| 2-33 | 0.05 |
| 2-34 | 0.12 |
| 2-35 | 1.3 |
| 2-36 | 0.58 |
| 2-37 | 0.05 |
| 2-38 | 2.4 |
| 2-39 | 5.0 |
| 2-40 | 1.8 |
| 2-41 | 2.3 |
| 2-42 | 7.0 |
| 2-43 | 6.6 |
| 2-44 | 0.07 |
| 2-44-1 | 0.02 |
| 2-44-2 | 0.13 |
| 2-45 | 0.03 |
| 2-45-1 | 0.30 |
| 2-45-2 | 0.02 |
| 2-46 | 0.33 |
| 2-46-1 | 0.12 |
| 2-46-2 | 0.50 |
| 2-47 | 1.0 |
| 2-47-1 | 2.0 |
| 2-47-2 | 0.65 |
| 2-48 | 0.08 |
| 2-49 | 0.08 |
| 2-50 | 0.03 |
| 2-50-1 | 0.20 |
| 2-50-2 | 0.02 |
| 2-51 | n.d. |
| 2-52 | 0.08 |
| Reference compound 2-4 | >10 |
| Reference compound 2-4-1 | >10 |
| Reference compound 2-4-2 | >10 |
| Reference compound 2-4-3 | 5.0 |
| Reference compound 2-4-4 | >10 |
| Reference compound 2-5 | >10 | n.d.: not determined

Mutant IDH1 Cellular Assay

Levels of (2R)-2-hydroxyglutarate (2HG) were measured in medium of a cell line with overexpression of mutated isocitrate dehydrogenase (mIDH) protein. mIDH catalyzes the NADPH-dependent reduction of alpha-ketoglutarate to 2-HG. Cells (LN229 R132H, Mohrenz et al., Apoptosis (2013) 18:1416-1425) were grown in DMEM containing 10% FCS. They were harvested by trypsin and seeded into 96-well plates. Cells were incubated overnight at 37° C. in 5% $CO_2$. The next day test compounds were added to each cell well. The final concentration of DMSO was 0.1% and DMSO controls were included. The plates were then placed in an incubator for 24 hours.

2-HG was measured according to Balss et al. (Acta Neuropathol (2012) 124: 883-891). Briefly, $HClO_4$ was added to each well and the plates were centrifuged. Aliquots are removed and incubated with hydroxyglutarate dehydrogenase (HGDH), diaphorase, NAD+, and resazurin. The conversion of resazurin to resorufin was detected by fluorescence spectroscopy at Ex 540 nm Em 600 nm. The increase in fluorescence is proportional to 2-HG production. $IC_{50}$ values are determined by interpolation from plots of relative fluorescence vs inhibitor concentration.

TABLE 6

IC$_{50}$ values of selected examples in mutant IDH1 cellular assay

| Example | Mutant IDH1 IC$_{50}$ [μM] |
| --- | --- |
| 2-7 | 3.0 |
| 2-18 | 1.8 |
| 2-18-1 | 2.6 |
| 2-19 | 2.3 |
| 2-19-2 | 1.2 |
| 2-27 | 0.50 |
| 2-28 | 1.1 |
| 2-28-2 | 0.12 |
| 2-29 | 0.95 |
| 2-29-2 | 0.60 |
| 2-32 | 2.7 |
| 2-32-2 | 2.5 |
| 2-33 | 0.35 |
| 2-34 | 1.9 |
| 2-37 | 2.5 |
| 2-44 | 0.17 |
| 2-44-1 | 0.40 |
| 2-44-2 | 2.6 |
| 2-45 | 0.16 |
| 2-45-1 | 1.6 |
| 2-45-2 | 0.12 |
| 2-46 | 1.5 |
| 2-46-1 | 0.60 |
| 2-48 | 0.80 |
| 2-49 | 0.28 |
| 2-50 | 0.21 |
| 2-50-1 | 3.6 |
| 2-50-2 | 0.38 |
| 2-52 | 1.8 |

The invention claimed is:
1. A compound of formula (I)

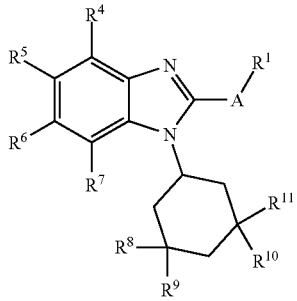

wherein:
A is a bond, a —CH$_2$— group, or a —(CH$_2$)$_2$— group, and
R$^5$ is selected from the group consisting of:
—C(O)OH, —C(=O)OR$^{12}$, HOC(=O)—(C$_1$-C$_6$-alkyl)-, R$^{12}$OC(=O)—(C$_1$-C$_6$-alkyl)-, HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)-, —C(=O)N(R$^{13}$)R$^{14}$, R$^{13}$(R$^{14}$)NC(=O)—(C$_1$-C$_6$-alkyl)-, R$^{13}$(R$^{14}$)NC(=O)—(C$_2$-C$_6$-alkenyl)-, R$^{13}$(R$^{14}$)NC(=O)—(C$_1$-C$_6$-alkoxy)- and cyano;
or
A is a —CH(CH$_3$)— group or a —C(CH$_3$)$_2$— group, and
R$^5$ is selected from the group consisting of:
—C(=O)OH, HOC(=O)—(C$_1$-C$_6$-alkyl)-, R$^{12}$OC(=O)—(C$_1$-C$_6$-alkyl)-, HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)-, —C(=O)N(R$^{13}$)R$^{14}$, R$^{13}$(R$^{14}$)NC(=O)—(C$_1$-C$_6$-alkyl)-, R$^{13}$(R$^{14}$)NC(=O)—(C$_2$-C$_6$-alkenyl)-, R$^{13}$(R$^{14}$)NC(=O)—(C$_1$-C$_6$-alkoxy)- and cyano;

R$^1$ is a phenyl group or a 5-, 6- or 9-membered heteroaryl group,
wherein the phenyl group is optionally substituted with one, two or three substituents, which are, independently of each other, a halogen atom or a group selected from the group consisting of:
C$_1$-C$_6$-alkyl, C$_3$-C$_6$-cycloalkyl, C$_1$-C$_6$-alkoxy, C$_3$-C$_6$-cycloalkyloxy, C$_1$-C$_6$-haloalkyl, C$_1$-C$_6$-haloalkoxy and cyano,
and
wherein the heteroaryl group is optionally substituted with one, two or three substituents, which are, independently of each other, a halogen atom or a group selected from the group consisting of:
C$_1$-C$_3$-alkyl and phenyl;
R$^4$ is a hydrogen atom or a halogen atom;
R$^6$ is a hydrogen atom, a halogen atom, or a group selected from the group consisting of:
C$_1$-C$_6$-alkyl, C$_1$-C$_6$-alkoxy, C$_3$-C$_6$-cycloalkyl, C$_3$-C$_6$-cycloalkyloxy, C$_1$-C$_6$-haloalkyl, C$_1$-C$_6$-haloalkoxy and cyano;
R$^7$ is a hydrogen atom;
R$^8$ is a C$_1$-C$_3$-alkyl group;
R$^9$, R$^{10}$, and R$^{11}$
are independently selected from the group consisting of:
hydrogen and C$_1$-C$_3$-alkyl;
R$^{12}$ is selected from the group consisting of:
C$_1$-C$_6$-alkyl and C$_3$-C$_6$-cycloalkyl; and
R$^{13}$ and R$^{14}$
are independently selected from the group consisting of:
hydrogen and C$_1$-C$_6$-alkyl;
or
R$^{13}$ and R$^{14}$
are taken together with the nitrogen atom to which they are attached to form a 4- to 6-membered heterocycloalkyl group,
wherein the 4- to 6-membered heterocycloalkyl group is optionally substituted with one substituent selected from the group consisting of: C$_1$-C$_3$-alkyl, C$_1$-C$_3$-haloalkyl, C$_1$-C$_3$-alkoxy, C$_1$-C$_3$-haloalkoxy, amino, hydroxy, halogen and cyano,
or
wherein the 4- to 6-membered heterocycloalkyl group is optionally substituted with two halogen atoms,
or a stereoisomer, a tautomer, an N-oxide, a hydrate, a solvate, or a salt thereof, or a mixture of any of the foregoing.
2. The compound according to claim 1, wherein:
A is a bond, a —CH$_2$— group, or a —(CH$_2$)$_2$— group, and
R$^5$ is selected from the group consisting of:
—C(O)OH, —C(=O)OR$^{12}$, HOC(=O)—(C$_1$-C$_6$-alkyl)-, R$^{12}$OC(=O)—(C$_1$-C$_6$-alkyl)-, HOC(=O)—(C$_2$-C$_6$-alkenyl)-, R$^{12}$OC(=O)—(C$_2$-C$_6$-alkenyl)-, HOC(=O)—(C$_1$-C$_6$-alkoxy)-, R$^{12}$OC(=O)—(C$_1$-C$_6$-alkoxy)- and cyano;
or
A is a —CH(CH$_3$)— group or a —C(CH$_3$)$_2$— group, and $R^5$ is selected from the group consisting of:
—C(=O)OH, HOC(=O)—($C_1$-$C_6$-alkyl)-, $R^{12}$OC(=O)—($C_1$-$C_6$-alkyl)-, HOC(=O)—($C_2$-$C_6$-alkenyl)-, $R^{12}$OC(=O)—($C_2$-$C_6$-alkenyl)-, HOC(=O)—($C_1$-$C_6$-alkoxy)-, $R^{12}$OC(=O)—($C_1$-$C_6$-alkoxy)- and cyano;

$R^1$ is a phenyl group or a 5-, 6- or 9-membered heteroaryl group,
wherein the phenyl group is optionally substituted with one, two or three substituents, which are, independently of each other, a halogen atom or a group selected from the group consisting of:
$C_1$-$C_6$-alkyl, $C_3$-$C_6$-cycloalkyl, $C_1$-$C_6$-alkoxy, $C_3$-$C_6$-cycloalkyloxy, $C_1$-$C_6$-haloalkyl, $C_1$-$C_6$-haloalkoxy and cyano;
and
wherein the heteroaryl group is optionally substituted with one, two or three substituents, which are, independently of each other, a halogen atom or a group selected from the group consisting of:
$C_1$-$C_3$-alkyl and phenyl;

$R^4$ is a hydrogen atom or a halogen atom;
$R^6$ is a hydrogen atom, a halogen atom, a group selected from the group consisting of:
$C_1$-$C_6$-alkyl, $C_1$-$C_6$-alkoxy, $C_3$-$C_6$-cycloalkyl, $C_3$-$C_6$-cycloalkyloxy, $C_1$-$C_6$-haloalkyl, $C_1$-$C_6$-haloalkoxy and cyano;
$R^7$ is a hydrogen atom;
$R^8$ is a $C_1$-$C_3$-alkyl group;
$R^9$, $R^{10}$, and $R^{11}$
are independently selected from the group consisting of:
hydrogen and $C_1$-$C_3$-alkyl; and
$R^{12}$ is selected from the group consisting of:
$C_1$-$C_6$-alkyl and $C_3$-$C_6$-cycloalkyl,
or a stereoisomer, a tautomer, an N-oxide, a hydrate, a solvate, or a salt thereof, or a mixture of any of the foregoing.

3. The compound according to claim 1, wherein:
A is a bond, a —$CH_2$— group, or a —($CH_2$)$_2$— group,
and
$R^5$ is selected from the group consisting of:
—C(O)OH, —C(=O)O$R^{12}$, HOC(=O)—($C_1$-$C_3$-alkyl)-, $R^{12}$OC(=O)—($C_1$-$C_3$-alkyl)-, HOC(=O)—($C_2$-$C_3$-alkenyl)-, $R^{12}$OC(=O)—($C_2$-$C_3$-alkenyl)-, HOC(=O)—($C_1$-$C_3$-alkoxy)-, $R^{12}$OC(=O)—($C_1$-$C_3$-alkoxy)- and cyano;
or
A is a —CH($CH_3$)— group or a —C($CH_3$)$_2$— group,
and
$R^5$ is selected from the group consisting of:
—C(=O)OH, HOC(=O)—($C_1$-$C_3$-alkyl)-, $R^{12}$OC(=O)—($C_1$-$C_3$-alkyl)-, HOC(=O)—($C_2$-$C_3$-alkenyl)-, $R^{12}$OC(=O)—($C_2$-$C_3$-alkenyl)-, HOC(=O)—($C_1$-$C_3$-alkoxy)-, $R^{12}$OC(=O)—($C_1$-$C_3$-alkoxy)- and cyano;
$R^1$ is a phenyl group or a 5-, 6- or 9-membered heteroaryl group,
wherein the phenyl group is optionally substituted with one, two or three substituents, which are, independently of each other, a halogen atom or a group selected from the group consisting of:
$C_1$-$C_6$-alkyl, $C_3$-$C_6$-cycloalkyl, $C_1$-$C_6$-alkoxy, $C_3$-$C_6$-cycloalkyloxy, $C_1$-$C_3$-haloalkyl, $C_1$-$C_3$-haloalkoxy and cyano,
and wherein the heteroaryl group is optionally substituted with one, two or three substituents, which are, independently of each other, a halogen atom or a group selected from the group consisting of:
$C_1$-$C_3$-alkyl and phenyl;
$R^4$ is a hydrogen atom or a halogen atom;
$R^6$ is a hydrogen atom, a halogen atom, or a group selected from the group consisting of:
$C_1$-$C_3$-alkyl, $C_1$-$C_6$-alkoxy, $C_3$-$C_6$-cycloalkyl, $C_3$-$C_6$-cycloalkyloxy, $C_1$-$C_3$-haloalkyl, $C_1$-$C_3$-haloalkoxy and cyano;
$R^7$ is a hydrogen atom;
$R^8$ is a $C_1$-$C_3$-alkyl group;
$R^9$, $R^{10}$, and $R^{11}$
are independently selected from the group consisting of:
hydrogen and $C_1$-$C_3$-alkyl; and
$R^{12}$ is a $C_1$-$C_3$-alkyl group,
or a stereoisomer, a tautomer, an N-oxide, a hydrate, a solvate, or a salt thereof, or a mixture of any of the foregoing.

4. The compound according to claim 1, wherein:
A is a bond or a —$CH_2$— group,
and
$R^5$ is selected from the group consisting of:
—C(O)OH, —C(=O)O$R^{12}$, HOC(=O)—($C_1$-$C_2$-alkyl)-, $R^{12}$OC(=O)—($C_1$-$C_2$-alkyl)- and cyano;
or
A is a —CH($CH_3$)— group or a —C($CH_3$)$_2$— group,
and
$R^5$ is a —C(=O)OH group;
$R^1$ is a phenyl group or a 5- or 9-membered heteroaryl group,
wherein the phenyl group is optionally substituted with one or two substituents, which are, independently of each other, a halogen atom or a group selected from the group consisting of:
$C_1$-$C_6$-alkyl, $C_1$-$C_6$-alkoxy, $C_1$-$C_3$-haloalkyl and $C_1$-$C_3$-haloalkoxy,
and
wherein the heteroaryl group is optionally substituted with one or two substituents, which are, independently of each other, a halogen atom or a group selected from the group consisting of:
$C_1$-$C_3$-alkyl and phenyl;
$R^4$ is a hydrogen atom or a halogen atom;
$R^6$ is a hydrogen atom or a group selected from the group consisting of:
$C_1$-$C_3$-alkyl, $C_1$-$C_6$-alkoxy, and $C_1$-$C_3$-haloalkoxy;
$R^7$ is a hydrogen atom;
$R^8$ is a methyl group;
$R^9$, $R^{10}$, and $R^{11}$
are independently selected from the group consisting of:
hydrogen and methyl; and
$R^{12}$ is a $C_1$-$C_3$-alkyl group,
or a stereoisomer, a tautomer, an N-oxide, a hydrate, a solvate, or a salt thereof, or a mixture of any of the foregoing.

5. The compound according to claim 1, wherein:
A is a bond or a —$CH_2$— group,
and
$R^5$ is selected from the group consisting of:
—C(O)OH, —C(=O)O$R^{12}$, HOC(=O)—($CH_2$)$_2$—, $R^{12}$OC(=O)—($CH_2$)$_2$— and cyano;
or
A is a —CH($CH_3$)— group or a —C($CH_3$)$_2$— group, and
R⁵ is a —C(=O)OH group;
R¹ is a phenyl group or a 5- or 9-membered heteroaryl group,
 wherein the phenyl group is optionally substituted with a fluorine atom or a group selected from the group consisting of:
  methyl, isopropyl, tert-butyl, isopropoxy, trifluoromethyl and trifluoromethoxy,
 and
 wherein the heteroaryl group is optionally substituted with one or two substituents, which are, independently of each other, a fluorine atom or a group selected from the group consisting of:
  methyl and phenyl;
R⁴ is a hydrogen atom or a fluorine atom;
R⁶ is a hydrogen atom or a group selected from the group consisting of:
 methyl, methoxy, isopropoxy and 2,2,2-trifluoroethoxy;
R⁷ is a hydrogen atom;
R⁸ is a methyl group;
R⁹ is selected from the group consisting of:
 hydrogen and methyl;
R¹⁰ and R¹¹ are each methyl groups; and
R¹² is a methyl group,
or a stereoisomer, a tautomer, an N-oxide, a hydrate, a solvate, or a salt thereof, or a mixture of any of the foregoing.

6. The compound according to claim 1, which is selected from the group consisting of:
(±) methyl 2-[4-(trifluoromethoxy)phenyl]-1-[(cis)-3,3,5-trimethylcyclohexyl]-1H-benzimidazole-5-carboxylate;
methyl 2-[4-(trifluoromethoxy)phenyl]-1-[(1R,5R)-3,3,5-trimethylcyclohexyl]-1H-benzimidazole-5-carboxylate;
methyl 2-[4-(trifluoromethoxy)phenyl]-1-[(1S,5S)-3,3,5-trimethylcyclohexyl]-1H-benzimidazole-5-carboxylate;
(±) 2-[4-(trifluoromethoxy)phenyl]-1-[(cis)-3,3,5-trimethylcyclohexyl]-1H-benzimidazole-5-carboxylic acid;
2-[4-(trifluoromethoxy)phenyl]-1-[(1R,5R)-3,3,5-trimethylcyclohexyl]-1H-benzimidazole-5-carboxylic acid;
2-[4-(trifluoromethoxy)phenyl]-1-[(1S,5S)-3,3,5-trimethylcyclohexyl]-1H-benzimidazole-5-carboxylic acid;
(±) methyl 2-[4-(trifluoromethoxy)benzyl]-1-[(cis)-3,3,5-trimethylcyclohexyl]-1H-benzimidazole-5-carboxylate;
methyl 2-[4-(trifluoromethoxy)benzyl]-1-[(1R,5R)-3,3,5-trimethylcyclohexyl]-1H-benzimidazole-5-carboxylate;
methyl 2-[4-(trifluoromethoxy)benzyl]-1-[(1S,5S)-3,3,5-trimethylcyclohexyl]-1H-benzimidazole-5-carboxylate;
(±) methyl 2-[4-(propan-2-yloxy)benzyl]-1-[(cis)-3,3,5-trimethylcyclohexyl]-1H-benzimidazole-5-carboxylate;
methyl 2-[4-(propan-2-yloxy)benzyl]-1-[(1R,5R)-3,3,5-trimethylcyclohexyl]-1H-benzimidazole-5-carboxylate;
methyl 2-[4-(propan-2-yloxy)benzyl]-1-[(1S,5S)-3,3,5-trimethylcyclohexyl]-1H-benzimidazole-5-carboxylate;
(±) methyl 2-[4-(propan-2-yl)benzyl]-1-[(cis)-3,3,5-trimethylcyclohexyl]-1H-benzimidazole-5-carboxylate;
methyl 2-[4-(propan-2-yl)benzyl]-1-[(1R,5R)-3,3,5-trimethylcyclohexyl]-1H-benzimidazole-5-carboxylate;
methyl 2-[4-(propan-2-yl)benzyl]-1-[(1S,5S)-3,3,5-trimethylcyclohexyl]-1H-benzimidazole-5-carboxylate;
(±) methyl 2-[4-(trifluoromethyl)benzyl]-1-[(cis)-3,3,5-trimethylcyclohexyl]-1H-benzimidazole-5-carboxylate;
methyl 2-[4-(trifluoromethyl)benzyl]-1-[(1R,5R)-3,3,5-trimethylcyclohexyl]-1H-benzimidazole-5-carboxylate;
methyl 2-[4-(trifluoromethyl)benzyl]-1-[(1S,5S)-3,3,5-trimethylcyclohexyl]-1H-benzimidazole-5-carboxylate;
(±) methyl 2-(4-fluorobenzyl)-1-[(cis)-3,3,5-trimethylcyclohexyl]-1H-benzimidazole-5-carboxylate;
methyl 2-(4-fluorobenzyl)-1-[(1R,5R)-3,3,5-trimethylcyclohexyl]-1H-benzimidazole-5-carboxylate;
methyl 2-(4-fluorobenzyl)-1-[(1S,5S)-3,3,5-trimethylcyclohexyl]-1H-benzimidazole-5-carboxylate;
(±) methyl 2-(4-methylbenzyl)-1-[(cis)-3,3,5-trimethylcyclohexyl]-1H-benzimidazole-5-carboxylate;
methyl 2-(4-methylbenzyl)-1-[(1R,5R)-3,3,5-trimethylcyclohexyl]-1H-benzimidazole-5-carboxylate;
methyl 2-(4-methylbenzyl)-1-[(1S,5S)-3,3,5-trimethylcyclohexyl]-1H-benzimidazole-5-carboxylate;
(±) methyl 2-(4-tert-butylbenzyl)-1-[(cis)-3,3,5-trimethylcyclohexyl]-1H-benzimidazole-5-carboxylate;
methyl 2-(4-tert-butylbenzyl)-1-[(1R,5R)-3,3,5-trimethylcyclohexyl]-1H-benzimidazole-5-carboxylate;
methyl 2-(4-tert-butylbenzyl)-1-[(1S,5S)-3,3,5-trimethylcyclohexyl]-1H-benzimidazole-5-carboxylate;
(±) methyl 2-benzyl-1-[(cis)-3,3,5-trimethylcyclohexyl]-1H-benzimidazole-5-carboxylate;
methyl 2-benzyl-1-[(1R,5R)-3,3,5-trimethylcyclohexyl]-1H-benzimidazole-5-carboxylate;
methyl 2-benzyl-1-[(1S,5S)-3,3,5-trimethylcyclohexyl]-1H-benzimidazole-5-carboxylate;
(±) methyl 2-[2-(trifluoromethoxy)benzyl]-1-[(cis)-3,3,5-trimethylcyclohexyl]-1H-benzimidazole-5-carboxylate;
methyl 2-[2-(trifluoromethoxy)benzyl]-1-[(1R,5R)-3,3,5-trimethylcyclohexyl]-1H-benzimidazole-5-carboxylate;
methyl 2-[2-(trifluoromethoxy)benzyl]-1-[(1S,5S)-3,3,5-trimethylcyclohexyl]-1H-benzimidazole-5-carboxylate;
(±) methyl 2-[3-(trifluoromethoxy)benzyl]-1-[(cis)-3,3,5-trimethylcyclohexyl]-1H-benzimidazole-5-carboxylate;
methyl 2-[3-(trifluoromethoxy)benzyl]-1-[(1R,5R)-3,3,5-trimethylcyclohexyl]-1H-benzimidazole-5-carboxylate;
methyl 2-[3-(trifluoromethoxy)benzyl]-1-[(1S,5S)-3,3,5-trimethylcyclohexyl]-1H-benzimidazole-5-carboxylate;
(±) methyl 2-[(4-methyl-2-phenyl-1,3-thiazol-5-yl)methyl]-1-[(cis)-3,3,5-trimethylcyclohexyl]-1H-benzimidazole-5-carboxylate;
methyl 2-[(4-methyl-2-phenyl-1,3-thiazol-5-yl)methyl]-1-[(1R,5R)-3,3,5-trimethylcyclohexyl]-1H-benzimidazole-5-carboxylate;
methyl 2-[(4-methyl-2-phenyl-1,3-thiazol-5-yl)methyl]-1-[(1S,5S)-3,3,5-trimethylcyclohexyl]-1H-benzimidazole-5-carboxylate;
(±) methyl 2-[(5-fluoro-2-methyl-1H-indol-3-yl)methyl]-1-[(cis)-3,3,5-trimethylcyclohexyl]-1H-benzimidazole-5-carboxylate;

methyl 2-[(5-fluoro-2-methyl-1H-indol-3-yl)methyl]-1-[(1R,5R)-3,3,5-trimethylcyclohexyl]-1H-benzimidazole-5-carboxylate;
methyl 2-[(5-fluoro-2-methyl-1H-indol-3-yl)methyl]-1-[(1S,5S)-3,3,5-trimethylcyclohexyl]-1H-benzimidazole-5-carboxylate;
(±) methyl 2-[(1-methyl-1H-indol-3-yl)methyl]-1-[(cis)-3,3,5-trimethylcyclohexyl]-1H-benzimidazole-5-carboxylate;
methyl 2-[(1-methyl-1H-indol-3-yl)methyl]-1-[(1R,5R)-3,3,5-trimethylcyclohexyl]-1H-benzimidazole-5-carboxylate;
methyl 2-[(1-methyl-1H-indol-3-yl)methyl]-1-[(1S,5S)-3,3,5-trimethylcyclohexyl]-1H-benzimidazole-5-carboxylate;
(±) methyl 6-methyl-2-[4-(trifluoromethoxy)benzyl]-1-[(cis)-3,3,5-trimethylcyclohexyl]-1H-benzimidazole-5-carboxylate;
methyl 6-methyl-2-[4-(trifluoromethoxy)benzyl]-1-[(1R,5R)-3,3,5-trimethylcyclohexyl]-1H-benzimidazole-5-carboxylate;
methyl 6-methyl-2-[4-(trifluoromethoxy)benzyl]-1-[(1S,5S)-3,3,5-trimethylcyclohexyl]-1H-benzimidazole-5-carboxylate;
(±) methyl 6-methoxy-2-[4-(trifluoromethoxy)benzyl]-1-[(cis)-3,3,5-trimethylcyclohexyl]-1H-benzimidazole-5-carboxylate;
methyl 6-methoxy-2-[4-(trifluoromethoxy)benzyl]-1-[(1R,5R)-3,3,5-trimethylcyclohexyl]-1H-benzimidazole-5-carboxylate;
methyl 6-methoxy-2-[4-(trifluoromethoxy)benzyl]-1-[(1S,5S)-3,3,5-trimethylcyclohexyl]-1H-benzimidazole-5-carboxylate;
(±) methyl 6-(propan-2-yloxy)-2-[4-(trifluoromethoxy)benzyl]-1-[(cis)-3,3,5-trimethylcyclohexyl]-1H-benzimidazole-5-carboxylate;
methyl 6-(propan-2-yloxy)-2-[4-(trifluoromethoxy)benzyl]-1-[(1R,5R)-3,3,5-trimethylcyclohexyl]-1H-benzimidazole-5-carboxylate;
methyl 6-(propan-2-yloxy)-2-[4-(trifluoromethoxy)benzyl]-1-[(1S,5S)-3,3,5-trimethylcyclohexyl]-1H-benzimidazole-5-carboxylate;
(±) methyl 6-(2,2,2-trifluoroethoxy)-2-[4-(trifluoromethoxy)benzyl]-1-[(cis)-3,3,5-trimethylcyclohexyl]-1H-benzimidazole-5-carboxylate;
methyl 6-(2,2,2-trifluoroethoxy)-2-[4-(trifluoromethoxy)benzyl]-1-[(1R,5R)-3,3,5-trimethylcyclohexyl]-1H-benzimidazole-5-carboxylate;
methyl 6-(2,2,2-trifluoroethoxy)-2-[4-(trifluoromethoxy)benzyl]-1-[(1S,5S)-3,3,5-trimethylcyclohexyl]-1H-benzimidazole-5-carboxylate;
methyl 4-fluoro-1-(3,3,5,5-tetramethylcyclohexyl)-2-[4-(trifluoromethoxy)benzyl]-1H-benzimidazole-5-carboxylate;
(±) 2-[4-(trifluoromethoxy)benzyl]-1-[(cis)-3,3,5-trimethylcyclohexyl]-1H-benzimidazole-5-carbonitrile;
2-[4-(trifluoromethoxy)benzyl]-1-[(1R,5R)-3,3,5-trimethylcyclohexyl]-1H-benzimidazole-5-carbonitrile;
2-[4-(trifluoromethoxy)benzyl]-1-[(1S,5S)-3,3,5-trimethylcyclohexyl]-1H-benzimidazole-5-carbonitrile;
(±) 2-[4-(propan-2-yloxy)benzyl]-1-[(cis)-3,3,5-trimethylcyclohexyl]-1H-benzimidazole-5-carbonitrile;
2-[4-(propan-2-yloxy)benzyl]-1-[(1R,5R)-3,3,5-trimethylcyclohexyl]-1H-benzimidazole-5-carbonitrile;
2-[4-(propan-2-yloxy)benzyl]-1-[(1S,5S)-3,3,5-trimethylcyclohexyl]-1H-benzimidazole-5-carbonitrile;
(±) 2-[4-(propan-2-yl)benzyl]-1-[(cis)-3,3,5-trimethylcyclohexyl]-1H-benzimidazole-5-carbonitrile;
2-[4-(propan-2-yl)benzyl]-1-[(1R,5R)-3,3,5-trimethylcyclohexyl]-1H-benzimidazole-5-carbonitrile;
2-[4-(propan-2-yl)benzyl]-1-[(1S,5S)-3,3,5-trimethylcyclohexyl]-1H-benzimidazole-5-carbonitrile;
(±) 2-[4-(trifluoromethyl)benzyl]-1-[(cis)-3,3,5-trimethylcyclohexyl]-1H-benzimidazole-5-carbonitrile;
2-[4-(trifluoromethyl)benzyl]-1-[(1R,5R)-3,3,5-trimethylcyclohexyl]-1H-benzimidazole-5-carbonitrile;
2-[4-(trifluoromethyl)benzyl]-1-[(1S,5S)-3,3,5-trimethylcyclohexyl]-1H-benzimidazole-5-carbonitrile;
(±) methyl 3-{6-methyl-2-[4-(trifluoromethoxy)benzyl]-1-[(cis)-3,3,5-trimethylcyclohexyl]-1H-benzimidazol-5-yl}propanoate;
methyl 3-{6-methyl-2-[4-(trifluoromethoxy)benzyl]-1-[(1R,5R)-3,3,5-trimethylcyclohexyl]-1H-benzimidazol-5-yl}propanoate;
methyl 3-{6-methyl-2-[4-(trifluoromethoxy)benzyl]-1-[(1S,5S)-3,3,5-trimethylcyclohexyl]-1H-benzimidazol-5-yl}propanoate;
(±) methyl 3-{6-methoxy-2-[4-(trifluoromethoxy)benzyl]-1-[(cis)-3,3,5-trimethylcyclohexyl]-1H-benzimidazol-5-yl}propanoate;
methyl 3-{6-methoxy-2-[4-(trifluoromethoxy)benzyl]-1-[(1R,5R)-3,3,5-trimethylcyclohexyl]-1H-benzimidazol-5-yl}propanoate;
methyl 3-{6-methoxy-2-[4-(trifluoromethoxy)benzyl]-1-[(1S,5S)-3,3,5-trimethylcyclohexyl]-1H-benzimidazol-5-yl}propanoate;
(±) 2-[4-(trifluoromethoxy)benzyl]-1-[(cis)-3,3,5-trimethylcyclohexyl]-1H-benzimidazole-5-carboxylic acid;
2-[4-(trifluoromethoxy)benzyl]-1-[(1R,5R)-3,3,5-trimethylcyclohexyl]-1H-benzimidazole-5-carboxylic acid;
2-[4-(trifluoromethoxy)benzyl]-1-[(1S,5S)-3,3,5-trimethylcyclohexyl]-1H-benzimidazole-5-carboxylic acid;
2-{1-[4-(trifluoromethoxy)phenyl]ethyl}-1-[(cis)-3,3,5-trimethylcyclohexyl]-1H-benzimidazole-5-carboxylic acid;
2-{(1R)-1-[4-(trifluoromethoxy)phenyl]ethyl}-1-[(1R,5R)-3,3,5-trimethylcyclohexyl]-1H-benzimidazole-5-carboxylic acid;
2-{(1S)-1-[4-(trifluoromethoxy)phenyl]ethyl}-1-[(1R,5R)-3,3,5-trimethylcyclohexyl]-1H-benzimidazole-5-carboxylic acid;
2-{(1R)-1-[4-(trifluoromethoxy)phenyl]ethyl}-1-[(1S,5S)-3,3,5-trimethylcyclohexyl]-1H-benzimidazole-5-carboxylic acid;
2-{(1S)-1-[4-(trifluoromethoxy)phenyl]ethyl}-1-[(1S,5S)-3,3,5-trimethylcyclohexyl]-1H-benzimidazole-5-carboxylic acid;
(±) 2-{2-[4-(trifluoromethoxy)phenyl]propan-2-yl}-1-[(cis)-3,3,5-trimethylcyclohexyl]-1H-benzimidazole-5-carboxylic acid;
2-{2-[4-(trifluoromethoxy)phenyl]propan-2-yl}-1-[(1R,5R)-3,3,5-trimethylcyclohexyl]-1H-benzimidazole-5-carboxylic acid;
2-{2-[4-(trifluoromethoxy)phenyl]propan-2-yl}-1-[(1S,5S)-3,3,5-trimethylcyclohexyl]-1H-benzimidazole-5-carboxylic acid;
(±) 2-[4-(propan-2-yloxy)benzyl]-1-[(cis)-3,3,5-trimethylcyclohexyl]-1H-benzimidazole-5-carboxylic acid;
2-[4-(propan-2-yloxy)benzyl]-1-[(1R,5R)-3,3,5-trimethylcyclohexyl]-1H-benzimidazole-5-carboxylic acid;
2-[4-(propan-2-yloxy)benzyl]-1-[(1S,5S)-3,3,5-trimethylcyclohexyl]-1H-benzimidazole-5-carboxylic acid;

(±) 2-[4-(propan-2-yl)benzyl]-1-[(cis)-3,3,5-trimethylcyclohexyl]-1H-benzimidazole-5-carboxylic acid;
2-[4-(propan-2-yl)benzyl]-1-[(1R,5R)-3,3,5-trimethylcyclohexyl]-1H-benzimidazole-5-carboxylic acid;
2-[4-(propan-2-yl)benzyl]-1-[(1S,5S)-3,3,5-trimethylcyclohexyl]-1H-benzimidazole-5-carboxylic acid;
(±) 2-[4-(trifluoromethyl)benzyl]-1-[(cis)-3,3,5-trimethylcyclohexyl]-1H-benzimidazole-5-carboxylic acid;
2-[4-(trifluoromethyl)benzyl]-1-[(1R,5R)-3,3,5-trimethylcyclohexyl]-1H-benzimidazole-5-carboxylic acid;
2-[4-(trifluoromethyl)benzyl]-1-[(1S,5S)-3,3,5-trimethylcyclohexyl]-1H-benzimidazole-5-carboxylic acid;
(±) 2-(4-fluorobenzyl)-1-[(cis)-3,3,5-trimethylcyclohexyl]-1H-benzimidazole-5-carboxylic acid;
2-(4-fluorobenzyl)-1-[(1R,5R)-3,3,5-trimethylcyclohexyl]-1H-benzimidazole-5-carboxylic acid;
2-(4-fluorobenzyl)-1-[(1S,5S)-3,3,5-trimethylcyclohexyl]-1H-benzimidazole-5-carboxylic acid;
(±) 2-(4-methylbenzyl)-1-[(cis)-3,3,5-trimethylcyclohexyl]-1H-benzimidazole-5-carboxylic acid;
2-(4-methylbenzyl)-1-[(1R,5R)-3,3,5-trimethylcyclohexyl]-1H-benzimidazole-5-carboxylic acid;
2-(4-methylbenzyl)-1-[(1S,5S)-3,3,5-trimethylcyclohexyl]-1H-benzimidazole-5-carboxylic acid;
(±) 2-(4-tert-butylbenzyl)-1-[(cis)-3,3,5-trimethylcyclohexyl]-1H-benzimidazole-5-carboxylic acid;
2-(4-tert-butylbenzyl)-1-[(1R,5R)-3,3,5-trimethylcyclohexyl]-1H-benzimidazole-5-carboxylic acid;
2-(4-tert-butylbenzyl)-1-[(1S,5S)-3,3,5-trimethylcyclohexyl]-1H-benzimidazole-5-carboxylic acid;
(±) 2-benzyl-1-[(cis)-3,3,5-trimethylcyclohexyl]-1H-benzimidazole-5-carboxylic acid;
2-benzyl-1-[(1R,5R)-3,3,5-trimethylcyclohexyl]-1H-benzimidazole-5-carboxylic acid;
2-benzyl-1-[(1S,5S)-3,3,5-trimethylcyclohexyl]-1H-benzimidazole-5-carboxylic acid;
(±) 2-[2-(trifluoromethoxy)benzyl]-1-[(cis)-3,3,5-trimethylcyclohexyl]-1H-benzimidazole-5-carboxylic acid;
2-[2-(trifluoromethoxy)benzyl]-1-[(1R,5R)-3,3,5-trimethylcyclohexyl]-1H-benzimidazole-5-carboxylic acid;
2-[2-(trifluoromethoxy)benzyl]-1-[(1S,5S)-3,3,5-trimethylcyclohexyl]-1H-benzimidazole-5-carboxylic acid;
(±) 2-[3-(trifluoromethoxy)benzyl]-1-[(cis)-3,3,5-trimethylcyclohexyl]-1H-benzimidazole-5-carboxylic acid;
2-[3-(trifluoromethoxy)benzyl]-1-[(1R,5R)-3,3,5-trimethylcyclohexyl]-1H-benzimidazole-5-carboxylic acid;
2-[3-(trifluoromethoxy)benzyl]-1-[(1S,5S)-3,3,5-trimethylcyclohexyl]-1H-benzimidazole-5-carboxylic acid;
(±) 2-[(4-methyl-2-phenyl-1,3-thiazol-5-yl)methyl]-1-[(cis)-3,3,5-trimethylcyclohexyl]-1H-benzimidazole-5-carboxylic acid;
2-[(4-methyl-2-phenyl-1,3-thiazol-5-yl)methyl]-1-[(1R,5R)-3,3,5-trimethylcyclohexyl]-1H-benzimidazole-5-carboxylic acid;
2-[(4-methyl-2-phenyl-1,3-thiazol-5-yl)methyl]-1-[(1S,5S)-3,3,5-trimethylcyclohexyl]-1H-benzimidazole-5-carboxylic acid;
(±) 2-[(5-fluoro-2-methyl-1H-indol-3-yl)methyl]-1-[(cis)-3,3,5-trimethylcyclohexyl]-1H-benzimidazole-5-carboxylic acid;
2-[(5-fluoro-2-methyl-1H-indol-3-yl)methyl]-1-[(1R,5R)-3,3,5-trimethylcyclohexyl]-1H-benzimidazole-5-carboxylic acid;
2-[(5-fluoro-2-methyl-1H-indol-3-yl)methyl]-1-[(1S,5S)-3,3,5-trimethylcyclohexyl]-1H-benzimidazole-5-carboxylic acid;
(±) 2-[(1-methyl-1H-indol-3-yl)methyl]-1-[(cis)-3,3,5-trimethylcyclohexyl]-1H-benzimidazole-5-carboxylic acid;
2-[(1-methyl-1H-indol-3-yl)methyl]-1-[(1R,5R)-3,3,5-trimethylcyclohexyl]-1H-benzimidazole-5-carboxylic acid;
2-[(1-methyl-1H-indol-3-yl)methyl]-1-[(1S,5S)-3,3,5-trimethylcyclohexyl]-1H-benzimidazole-5-carboxylic acid;
(±) 6-methyl-2-[4-(trifluoromethoxy)benzyl]-1-[(cis)-3,3,5-trimethylcyclohexyl]-1H-benzimidazole-5-carboxylic acid;
6-methyl-2-[4-(trifluoromethoxy)benzyl]-1-[(1R,5R)-3,3,5-trimethylcyclohexyl]-1H-benzimidazole-5-carboxylic acid;
6-methyl-2-[4-(trifluoromethoxy)benzyl]-1-[(1S,5S)-3,3,5-trimethylcyclohexyl]-1H-benzimidazole-5-carboxylic acid;
(±) 6-methoxy-2-[4-(trifluoromethoxy)benzyl]-1-[(cis)-3,3,5-trimethylcyclohexyl]-1H-benzimidazole-5-carboxylic acid;
6-methoxy-2-[4-(trifluoromethoxy)benzyl]-1-[(1R,5R)-3,3,5-trimethylcyclohexyl]-1H-benzimidazole-5-carboxylic acid;
6-methoxy-2-[4-(trifluoromethoxy)benzyl]-1-[(1S,5S)-3,3,5-trimethylcyclohexyl]-1H-benzimidazole-5-carboxylic acid;
(±) 6-(propan-2-yloxy)-2-[4-(trifluoromethoxy)benzyl]-1-[(cis)-3,3,5-trimethylcyclohexyl]-1H-benzimidazole-5-carboxylic acid;
6-(propan-2-yloxy)-2-[4-(trifluoromethoxy)benzyl]-1-[(1R,5R)-3,3,5-trimethylcyclohexyl]-1H-benzimidazole-5-carboxylic acid;
6-(propan-2-yloxy)-2-[4-(trifluoromethoxy)benzyl]-1-[(1S,5S)-3,3,5-trimethylcyclohexyl]-1H-benzimidazole-5-carboxylic acid;
(±) 6-(2,2,2-trifluoroethoxy)-2-[4-(trifluoromethoxy)benzyl]-1-[(cis)-3,3,5-trimethylcyclohexyl]-1H-benzimidazole-5-carboxylic acid;
6-(2,2,2-trifluoroethoxy)-2-[4-(trifluoromethoxy)benzyl]-1-[(1R,5R)-3,3,5-trimethylcyclohexyl]-1H-benzimidazole-5-carboxylic acid;
6-(2,2,2-trifluoroethoxy)-2-[4-(trifluoromethoxy)benzyl]-1-[(1S,5S)-3,3,5-trimethylcyclohexyl]-1H-benzimidazole-5-carboxylic acid;
4-fluoro-1-(3,3,5,5-tetramethylcyclohexyl)-2-[4-(trifluoromethoxy)benzyl]-1H-benzimidazole-5-carboxylic acid;
(±) 3-{6-methyl-2-[4-(trifluoromethoxy)benzyl]-1-[(cis)-3,3,5-trimethylcyclohexyl]-1H-benzimidazol-5-yl}propanoic acid;
3-{6-methyl-2-[4-(trifluoromethoxy)benzyl]-1-[(1R,5R)-3,3,5-trimethylcyclohexyl]-1H-benzimidazol-5-yl}propanoic acid;
3-{6-methyl-2-[4-(trifluoromethoxy)benzyl]-1-[(1,5)-3,3,5-trimethylcyclohexyl]-1H-benzimidazol-5-yl}propanoic acid;
(±) 3-{6-methoxy-2-[4-(trifluoromethoxy)benzyl]-1-[(cis)-3,3,5-trimethylcyclohexyl]-1H-benzimidazol-5-yl}propanoic acid;
3-{6-methoxy-2-[4-(trifluoromethoxy)benzyl]-1-[(1R,5R)-3,3,5-trimethylcyclohexyl]-1H-benzimidazol-5-yl}propanoic acid;
3-{6-methoxy-2-[4-(trifluoromethoxy)benzyl]-1-[(1S,5S)-3,3,5-trimethylcyclohexyl]-1H-benzimidazol-5-yl}propanoic acid;

methyl 3-{4-fluoro-1-(3,3,5,5-tetramethylcyclohexyl)-2-[4-(trifluoromethoxy)benzyl]-1H-benzimidazol-5-yl}propanoate; and 3-{4-fluoro-1-(3,3,5,5-tetramethylcyclohexyl)-2-[4-(trifluoromethoxy)benzyl]-1H-benzimidazol-5-yl}propanoic acid, or a stereoisomer, a tautomer, an N-oxide, a hydrate, a solvate, or a salt thereof, or a mixture of any of the foregoing.

7. A method of preparing the compound of formula (I) according to claim 1, comprising reacting an intermediate compound of formula (II):

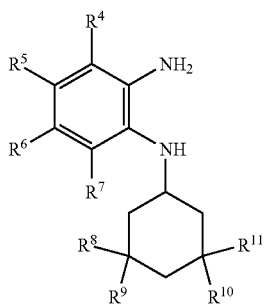
(II)

wherein $R^4$, $R^5$, $R^6$, $R^7$, $R^8$, $R^9$, $R^{10}$ and $R^{11}$ are as defined for the compound of formula (I) according to claim 1, with a compound of formula (III):

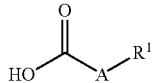
(III)

wherein $R^1$ and A are as defined as for the compound of formula (I) according to claim 1, to give the compound of formula (I):

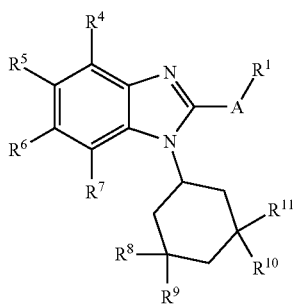
(I)

wherein $R^1$, $R^4$, $R^5$, $R^6$, $R^7$, $R^8$, $R^9$, $R^{10}$, $R^{11}$ and A are as defined for the compound of formula (I) according to claim 1.

8. A method of preparing the compound of formula (I) according to claim 1, comprising reacting an intermediate compound of formula (II):

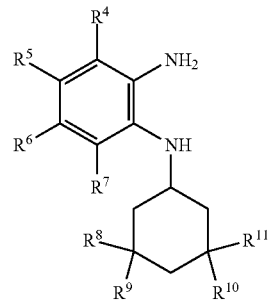
(II)

wherein $R^4$, $R^5$, $R^6$, $R^7$, $R^8$, $R^9$, $R^{10}$ and $R^{11}$ are as defined for the compound of formula (I) according to claim 1, with a compound of formula (IV):

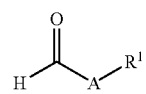
(IV)

wherein $R^1$ and A are as defined as for the compound of formula (I) according to claim 1, to give the compound of formula (I):

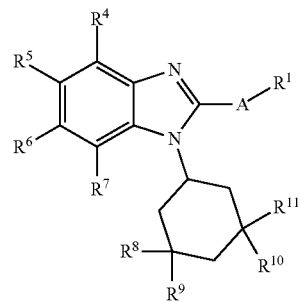
(I)

wherein $R^1$, $R^4$, $R^5$, $R^6$, $R^7$, $R^8$, $R^9$, $R^{10}$, $R^{11}$ and A are as defined for the compound of formula (I) according to claim 1.

9. A pharmaceutical composition comprising the compound of formula (I) according to claim 1, or a stereoisomer, a tautomer, an N-oxide, a hydrate, a solvate, or a salt thereof, or a mixture of any of the foregoing, and a pharmaceutically acceptable diluent or carrier.

10. A pharmaceutical combination comprising:
one or more first active ingredients selected from the compound of formula (I) according to claim 1, or a stereoisomer, a tautomer, an N-oxide, a hydrate, a solvate, or a salt thereof, or a mixture of any of the foregoing, and
one or more second active ingredients selected from chemotherapeutic anti-cancer agents.

11. A method for treatment of a disease, comprising administering to a patient in need thereof a therapeutically effective amount of the compound of formula (I) according to claim 1, or a stereoisomer, an N-oxide, a hydrate, a solvate, or a salt thereof, or a mixture of any of the foregoing, wherein said disease is leukaemia, myelodysplastic syndrome, malignant lymphoma, a head and neck tumour, a brain tumour, a tumour of the thorax, a non-small cell lung tumour, a small cell lung tumour, a gastrointestinal tumour, an endocrine tumour, a mammary tumour, a gynaecological tumour, a urological tumour, a renal tumour, a bladder tumour, a prostate tumour, a skin tumour, sarcoma, or metastases thereof.

12. The compound according to claim 1 or a salt thereof.

13. The compound according to claim 6 or a salt thereof.

14. The pharmaceutical composition according to claim 9, comprising the compound of formula (I) or a salt thereof.

15. The pharmaceutical combination according to claim 10, comprising the compound of formula (I) or a salt thereof.

* * * * *